(12) United States Patent
Hartwell et al.

(10) Patent No.: US 12,357,230 B2
(45) Date of Patent: *Jul. 15, 2025

(54) DRESSING SYSTEM WITH FOOT LOAD MONITORING

(71) Applicant: T.J.Smith and Nephew, Limited, Hull (GB)

(72) Inventors: Edward Yerbury Hartwell, Hull (GB); Allan Kenneth Frazer Grugeon Hunt, Beverley (GB); Felix Clarence Quintanar, Hull (GB)

(73) Assignee: T.J.Smith and Nephew, Limited, Hull (GB)

( * ) Notice: Subject to any disclaimer, the term of this patent is extended or adjusted under 35 U.S.C. 154(b) by 0 days.

This patent is subject to a terminal disclaimer.

(21) Appl. No.: 18/141,583

(22) Filed: May 1, 2023

(65) Prior Publication Data

US 2023/0337970 A1 Oct. 26, 2023

Related U.S. Application Data

(63) Continuation of application No. 16/971,175, filed as application No. PCT/EP2019/054091 on Feb. 19, 2019, now Pat. No. 11,638,554.

(30) Foreign Application Priority Data

Feb. 21, 2018 (GB) ........................................ 1802756
Feb. 21, 2018 (GB) ........................................ 1802759
(Continued)

(51) Int. Cl.
A61B 5/00 (2006.01)
A61B 5/11 (2006.01)
(Continued)

(52) U.S. Cl.
CPC ............ *A61B 5/4595* (2013.01); *A61B 5/002* (2013.01); *A61B 5/1123* (2013.01);
(Continued)

(58) Field of Classification Search
CPC ......... A61B 5/4595; A61B 5/002; A61B 5/11; A61B 5/1118; A61B 5/1123;
(Continued)

(56) References Cited

U.S. PATENT DOCUMENTS

| 3,974,491 A | 8/1976 | Sipe |
|---|---|---|
| 4,610,253 A | 9/1986 | Rosenberg |

(Continued)

FOREIGN PATENT DOCUMENTS

| CN | 105631195 B | 12/2017 |
|---|---|---|
| DE | 19612334 A1 | 1/1997 |

(Continued)

OTHER PUBLICATIONS

Abbott Diabetes Care Ltd., "FreeStyle Libre Flash Glucose Monitoring System—User's Manual," Mar. 2014, 124 pages.
(Continued)

*Primary Examiner* — Jennifer Robertson
*Assistant Examiner* — Nidhi N Patel
(74) *Attorney, Agent, or Firm* — Knobbe, Martens, Olson & Bear, LLP

(57) ABSTRACT

Embodiments of systems and methods for monitoring use of an orthopedic device are at least disclosed. In some embodiments, the system can include an orthopedic device, a housing, and a controller. The orthopedic device can provide support to a limb of an individual. The orthopedic device can include a magnet configured to generate a magnetic field. The housing can attach to the individual, and the housing can support a magnetometer configured to generate a signal responsive to the magnetic field. The controller can deter-
(Continued)

mine from the signal whether the individual is using the orthopedic device to provide support to the limb and accordingly output usage indications.

20 Claims, 35 Drawing Sheets

(30) Foreign Application Priority Data

Feb. 21, 2018 (GB) ...................................... 1802765
Feb. 21, 2018 (GB) ...................................... 1802770

(51) Int. Cl.
*A61F 13/05* (2024.01)
*A61F 13/06* (2006.01)
*A61M 1/00* (2006.01)

(52) U.S. Cl.
CPC ............ *A61B 5/6829* (2013.01); *A61B 5/742* (2013.01); *A61F 13/05* (2024.01); *A61F 13/064* (2013.01); *A61M 1/90* (2021.05); *A61B 2562/0219* (2013.01); *A61B 2562/0247* (2013.01); *A61M 2210/08* (2013.01)

(58) Field of Classification Search
CPC ..... A61B 5/6829; A61B 5/742; A61B 5/4538; A61B 5/4833; A61B 5/6828–6829; A61B 5/6835; A61B 2562/0219; A61B 2562/0247; A61F 13/00068; A61F 13/064–069; A61M 1/90; A61M 2210/08
See application file for complete search history.

(56) References Cited

U.S. PATENT DOCUMENTS

| | | | |
|---|---|---|---|
| 5,107,854 A | 4/1992 | Knotts et al. | |
| 5,253,654 A | 10/1993 | Thomas et al. | |
| 5,642,096 A | 6/1997 | Leyerer et al. | |
| 5,875,571 A | 3/1999 | Huang | |
| 5,879,292 A | 3/1999 | Sternberg et al. | |
| 6,031,463 A | 2/2000 | Bechmann | |
| 6,282,448 B1 | 8/2001 | Katz et al. | |
| 6,287,253 B1 | 9/2001 | Ortega et al. | |
| 6,571,193 B1 | 5/2003 | Unuma et al. | |
| 7,214,202 B1 | 5/2007 | Vogel et al. | |
| 7,998,092 B2 | 8/2011 | Avni et al. | |
| 8,111,165 B2 | 2/2012 | Ortega et al. | |
| 8,280,682 B2 | 10/2012 | Vock et al. | |
| 8,388,553 B2 | 3/2013 | James et al. | |
| 8,753,275 B2 | 6/2014 | Najafi et al. | |
| 8,925,392 B2 | 1/2015 | Esposito et al. | |
| 8,947,237 B2 | 2/2015 | Margon et al. | |
| 9,220,455 B2 | 12/2015 | Sarrafzadeh et al. | |
| 9,427,179 B2 | 8/2016 | Mestrovic et al. | |
| 9,439,599 B2 | 9/2016 | Thompson et al. | |
| 9,629,585 B2 | 4/2017 | Das et al. | |
| 9,861,550 B2 | 1/2018 | Ribble et al. | |
| 9,907,103 B2 | 2/2018 | Chen et al. | |
| 10,019,555 B2 | 7/2018 | Manice et al. | |
| 10,085,675 B2 | 10/2018 | Nagasaki et al. | |
| 10,166,164 B2 | 1/2019 | Johnson et al. | |
| 10,274,305 B2 | 4/2019 | Huang et al. | |
| 10,335,636 B2 | 7/2019 | Holma et al. | |
| 11,375,944 B2 | 7/2022 | Gruben et al. | |
| 11,638,554 B2 * | 5/2023 | Hartwell ................ | A61B 5/742 |
| | | | 600/595 |
| 2003/0088294 A1 | 5/2003 | Gesotti | |
| 2005/0099294 A1 | 5/2005 | Bogner et al. | |
| 2005/0165284 A1 | 7/2005 | Gefen | |
| 2006/0149171 A1 * | 7/2006 | Vogel .................... | A61F 13/069 |
| | | | 601/151 |
| 2007/0173903 A1 | 7/2007 | Goren et al. | |
| 2008/0216593 A1 | 9/2008 | Jacobsen et al. | |
| 2008/0287832 A1 | 11/2008 | Collins et al. | |
| 2009/0069727 A1 | 3/2009 | Neustaedter et al. | |
| 2009/0070939 A1 | 3/2009 | Hann | |
| 2009/0183390 A1 * | 7/2009 | Miller .................... | A43D 1/022 |
| | | | 36/43 |
| 2009/0209830 A1 | 8/2009 | Nagle et al. | |
| 2009/0234249 A1 | 9/2009 | Randolph | |
| 2009/0234262 A1 | 9/2009 | Reid, Jr. et al. | |
| 2009/0292194 A1 | 11/2009 | Libbus et al. | |
| 2010/0056873 A1 | 3/2010 | Allen et al. | |
| 2010/0162832 A1 | 7/2010 | Brauers | |
| 2010/0198022 A1 | 8/2010 | Vuillerme et al. | |
| 2010/0225476 A1 | 9/2010 | Klose | |
| 2010/0268111 A1 | 10/2010 | Drinan et al. | |
| 2010/0298742 A1 | 11/2010 | Perlman et al. | |
| 2010/0324455 A1 | 12/2010 | Rangel et al. | |
| 2011/0054359 A1 | 3/2011 | Sazonov et al. | |
| 2011/0130697 A1 | 6/2011 | Nagle et al. | |
| 2011/0214501 A1 | 9/2011 | Ross et al. | |
| 2011/0263950 A1 | 10/2011 | Larson et al. | |
| 2012/0010535 A1 | 1/2012 | Kubiak et al. | |
| 2012/0109013 A1 | 5/2012 | Everett et al. | |
| 2012/0136325 A1 * | 5/2012 | Allen .................... | A61M 1/75 |
| | | | 604/319 |
| 2012/0185267 A1 | 7/2012 | Kamen et al. | |
| 2012/0238914 A1 | 9/2012 | Goldfield et al. | |
| 2013/0023720 A1 | 1/2013 | Solomon et al. | |
| 2013/0167848 A1 | 7/2013 | Frassica et al. | |
| 2013/0213145 A1 | 8/2013 | Owings et al. | |
| 2013/0282324 A1 | 10/2013 | Carter et al. | |
| 2013/0317753 A1 | 11/2013 | Kamen et al. | |
| 2014/0089673 A1 | 3/2014 | Luna | |
| 2014/0135657 A1 | 5/2014 | Wu et al. | |
| 2014/0188499 A1 | 7/2014 | Bell et al. | |
| 2014/0200486 A1 | 7/2014 | Bechtel et al. | |
| 2014/0203797 A1 | 7/2014 | Stivoric et al. | |
| 2014/0221787 A1 | 8/2014 | Teller et al. | |
| 2014/0235166 A1 | 8/2014 | Molettiere et al. | |
| 2014/0303460 A1 | 10/2014 | Corley et al. | |
| 2014/0350435 A1 | 11/2014 | Lam | |
| 2014/0378786 A1 | 12/2014 | Hong et al. | |
| 2015/0125839 A1 | 5/2015 | Tillges et al. | |
| 2015/0182843 A1 | 7/2015 | Esposito et al. | |
| 2016/0092651 A1 | 3/2016 | Austin et al. | |
| 2016/0120433 A1 | 5/2016 | Hughes et al. | |
| 2016/0135731 A1 | 5/2016 | Drennan | |
| 2016/0213924 A1 | 7/2016 | Coleman et al. | |
| 2016/0228050 A1 | 8/2016 | Sugla et al. | |
| 2016/0256080 A1 | 9/2016 | Shen et al. | |
| 2016/0275776 A1 | 9/2016 | Shen et al. | |
| 2016/0296144 A1 | 10/2016 | Gaddam et al. | |
| 2016/0317083 A1 | 11/2016 | DeLuke et al. | |
| 2016/0317084 A1 | 11/2016 | DeLuke et al. | |
| 2016/0331322 A1 | 11/2016 | Son et al. | |
| 2016/0367192 A1 | 12/2016 | Iyengar et al. | |
| 2017/0011210 A1 | 1/2017 | Cheong et al. | |
| 2017/0027498 A1 | 2/2017 | Larson et al. | |
| 2017/0027529 A1 | 2/2017 | Frieder et al. | |
| 2017/0055851 A1 | 3/2017 | Al-Ali | |
| 2017/0056724 A1 | 3/2017 | Baker | |
| 2017/0160400 A1 | 6/2017 | Larbi | |
| 2017/0225033 A1 | 8/2017 | Czaja | |
| 2017/0231015 A1 | 8/2017 | Jang et al. | |
| 2017/0281073 A1 | 10/2017 | Drennan et al. | |
| 2017/0312165 A1 | 11/2017 | Johnson et al. | |
| 2017/0347899 A1 | 12/2017 | Bhushan et al. | |
| 2017/0367644 A1 | 12/2017 | Sharman et al. | |
| 2018/0000407 A1 | 1/2018 | Johnson et al. | |
| 2018/0020931 A1 | 1/2018 | Shusterman | |
| 2018/0025146 A1 | 1/2018 | Vasyltsov et al. | |
| 2018/0074547 A1 | 3/2018 | Smadi et al. | |
| 2018/0132287 A1 | 5/2018 | Cheng et al. | |
| 2018/0250452 A1 * | 9/2018 | Locke .................... | A61M 1/96 |
| 2018/0271409 A1 | 9/2018 | Gong et al. | |
| 2018/0360157 A1 | 12/2018 | Jeong et al. | |
| 2019/0082771 A1 | 3/2019 | Shin et al. | |

(56) References Cited

U.S. PATENT DOCUMENTS

| | | | |
|---|---|---|---|
| 2019/0192744 A1 | 6/2019 | Greener et al. |
| 2021/0379255 A2 | 12/2021 | Weston |
| 2023/0157897 A1 | 5/2023 | Engel et al. |

FOREIGN PATENT DOCUMENTS

| | | |
|---|---|---|
| DE | 102013013013 A1 | 2/2015 |
| DE | 102014222955 A1 | 5/2016 |
| EP | 2675315 B1 | 5/2020 |
| JP | 2005245709 A | 9/2005 |
| JP | 2014046151 A | 3/2014 |
| WO | WO-2005121729 A1 | 12/2005 |
| WO | WO-2011113070 A1 | 9/2011 |
| WO | WO-2013064852 A1 | 5/2013 |
| WO | WO-2014178755 A1 | 11/2014 |
| WO | WO-2016018448 A1 | 2/2016 |
| WO | WO-2016109744 A1 | 7/2016 |
| WO | WO-2016154230 A1 | 9/2016 |
| WO | WO-2016176544 A1 | 11/2016 |
| WO | WO-2016180073 A1 | 11/2016 |
| WO | WO-2016186904 A1 | 11/2016 |
| WO | WO-2017048979 A1 | 3/2017 |
| WO | WO-2017205728 A1 | 11/2017 |
| WO | WO-2017214188 A1 | 12/2017 |
| WO | WO-2018096390 A1 | 5/2018 |
| WO | WO-2018144946 A1 | 8/2018 |
| WO | WO-2018162736 A1 | 9/2018 |
| WO | WO-2019042790 A1 | 3/2019 |
| WO | WO-2019096828 A1 | 5/2019 |
| WO | WO-2019162272 A1 | 8/2019 |
| WO | WO-2019234011 A1 | 12/2019 |
| WO | WO-2019238927 A1 | 12/2019 |
| WO | WO-2019243171 A1 | 12/2019 |
| WO | WO-2020159677 A1 | 8/2020 |

OTHER PUBLICATIONS

Amjadi M., et al., "Ultra-Stretchable and Skin-Mountable Strain Sensors Using Carbon Nanotubes-Ecoflex Nanocomposites," Nanotechnology, Institute of Physics Publishing, vol. 26, No. 37, Aug. 25, 2015, 11 pages.

Centauri Medical, Inc., "DynaSense—Instructions for Use," Document No. 1312AJ (User Manual), Jul. 2013, 54 pages.

Crews R., et al., "Role and Determinants of Adherence to Offloading in Diabetic Foot Ulcer Healing: A Prospective Investigation," Diabetes Care, vol. 39, Aug. 2016, pp. 1371-1377 (7 pages).

Crews R. T., et al., "A Method for Assessing Off-loading Compliance," Journal of the American Podiatric Medical Association, vol. 99, No. 2, Mar./Apr. 2009, 6 pages.

Fitbit, "Introducing Fitbit Coach," YouTube, retrieved from https://www.youtube.com/watch?v=QDYxWeQMrAw , Oct. 24, 2017, 1 page.

Hanft J., et al., "A Guide to Preventative Offloading of Diabetic Foot Ulcers," Podiatry Today, Nov. 2011, retrieved from www.podiatrytoday.com/guide-preventative-offloading-diabetic-foot-ulcers , 8 pages.

International Preliminary Report on Patentability for Application No. PCT/EP2019/054091, mailed on Sep. 3, 2020, 16 pages.

International Search Report and Written Opinion for Application No. PCT/EP2019/054091, mailed on Jun. 12, 2019, 20 pages.

Invitation to Pay Additional Fees and Partial Search Report for Application No. PCT/EP2019/054091, mailed on Apr. 17, 2019, 21 pages.

Kosecki D., "9 Things You Need to Know About Your New Fitbit Coach Subscription," Fitbit, Dec. 22, 2017, retrieved from https://blog.fitbit.com/new-fitbit-coach/ , 12 pages.

Muscillo R., et al., "An Adaptive Kalman-Based Bayes Estimation Technique to Classify Locomotor Activities in Young and Elderly Adults Through Accelerometers," Medical Engineering & Physics, Butterworth-Heinemann, GB, vol. 32, No. 8, Oct. 1, 2010 (Oct. 1, 2010), pp. 849-859, XP027267622, ISSN:1350-4533 [retrieved on Jun. 23, 2010] the whole document.

Nakamoto., H., et al., "Stretchable Strain Sensor with Anisotropy and Application for Joint Angle Measurement," IEEE Sensors Journal, vol. 16, No. 10, May 2016, pp. 3572-3579.

Raviglione A., et al., "Real-Time Smart Textile-Based System to Monitor Pressure Offloading of Diabetic Foot Ulcers," Journal of Diabetes Science and Technology, vol. 11, Sep. 2017, 5 pages.

Smith and Nephew Medical Ltd., "SANDY 2012980—Healthcare Professional User Manual," Jul. 2018, retrieved from https://apps.fcc.gov/oetcf/eas/reports/ViewExhibitReport.cfm?mode=Exhibits&calledFromFrame=N&application_id=f%2FbhDROyt nS96PwjOmDTNA%3D%3D&fcc_id=2AEAJ-2012980 , retrieved on Aug. 22, 2018, 8 pages.

Tairych A., et al., "Distributed Sensing: Multiple Capacitive Stretch Sensors on a Single Channel," Proceedings of SPIE, vol. 10163, Apr. 17, 2017, pp. 1016306-1-1016306-10.

Votzke C., et al., "Highly-Stretchable Biomechanical Strain Sensor Using Printed Liquid Metal Paste," IEEE Biomedical Circuits and Systems Conference (BIOCAS), Oct. 17, 2018, XP033483141, 4 pages.

\* cited by examiner

DRESSING SYSTEM WITH FOOT LOAD MONITORING

CROSS-REFERENCE TO RELATED APPLICATIONS

This application is a continuation of U.S. application Ser. No. 16/971,175, filed Aug. 19, 2020, which is a U.S. national stage application of International Patent Application No. PCT/EP2019/054091, filed Feb. 19, 2019, which claims priority to U.K. Provisional Application Nos. 1802770.6, 1802756.5, 1802759.9, and 1802765.6, filed on Feb. 21, 2018; the disclosures of which are hereby incorporated by reference in their entirety.

BACKGROUND

Field

Embodiments of the present disclosure relate to apparatuses, systems, and methods for the monitoring of body loading and body position for treatment of pressure ulcers.

Description of the Related Art

Pressure ulcers, which are also known as pressure sores, bedsores, or decubitus ulcers, are injuries to skin and underlying tissue resulting from prolonged pressure on the skin, soft tissue, muscle, or bone above capillary filling pressure (approximately 32 mmHg). Pressure ulcers may typically develop on skin that covers bony areas, such as heels, ankles, hips, shoulder blades, spine, elbows, back of the head, and tailbone as illustrated in FIG. 1. Persons whose mobility is limited due to age or medical conditions are at an increased risk of developing pressure ulcers because of their inability to change positions while sitting or lying down. Management and treatment of pressure ulcers include repositioning of the injured limb or body part and using support surfaces, such as a mattress, cushion, or the like.

One type of pressure ulcer that develops on a foot is known as a diabetic foot ulcer (DFU), which tends to occur with higher frequency and intensity in the diabetic population. Management and treatment of diabetic foot ulcers requires offloading the wound by using cushioned footwear, such as a support boot, cast, shoe, etc. While offloading can be effective, because many offloading devices are removable, it has been found that patient non-compliance with the offloading devices plays a large role in the delayed healing of diabetic foot ulcers.

However, prior art approaches and systems provide no or little information regarding patients' lifestyle and non-compliance or compliance with the offloading devices and support surfaces. Gaining insight into patients' lifestyle can be important for prevention and healing of pressure ulcers. However, because of these limitations, prevention and healing of patients' pressure ulcers using prior art approaches and systems may be delayed or, worse yet, the condition could worsen leading to prolonged discomfort, hospitalization, or even surgery.

SUMMARY

In some embodiments, an apparatus for monitoring load bearing of a foot is disclosed. The apparatus can include an elongate conduit, a pressure sensor, and a controller. The elongate conduit can include a conduit head configured to attach to a foot of an individual. The elongate conduit can have an internal volume that retains a gas or a liquid within the internal volume, and the elongate conduit can include a collapsible portion. The pressure sensor can measure a pressure within the internal volume. The controller can: determine, from a change in the pressure over a period of time, that the foot has supported a threshold amount of weight within the period of time, and output for presentation an indication in response to determining that the foot has supported the threshold amount of weight within the period of time.

The apparatus of the preceding paragraph can include one or more of the following features: The elongate conduit can include a reinforcement element configured to prevent collapse of a non-collapsible portion of the elongate conduit and not the collapsible portion or cause the collapsible portion to return to a pre-load state or shape after removal of loading. A section of the elongate conduit can non-extensible (which can facilitate the predictable transmission of pressure within the elongate conduit). The non-collapsible portion can be larger than the collapsible portion. The section of the elongate conduit that may be non-extensible can be part of the non-collapsible portion. The second portion can include an inner volume of the conduit head. The reinforcement element can include foam. The elongate conduit can include a first channel and a second channel, the first channel ending in a first channel head and the second channel ending in a second channel head, the first channel head and the second channel head forming at least part of the conduit head, the first channel head being configured to be mounted to a first part of the foot and the second channel head being configured to be mounted to a second part of the foot different from the first part. The pressure sensor can measure the pressure in the first channel separately from the pressure in the second channel. The controller can (i) determine, from a change in the pressure in the first channel over a first time duration, that the first part of the foot has supported a first amount of weight within the first time duration, and (ii) determine, from a change in the pressure in the second channel over a second time duration, that the second part of the foot has supported a second amount of weight within the second time duration. The controller can determine a weight distribution on the foot from a change in the pressure in the first channel and the second channel over the period of time. The first channel head and the second channel head can be mounted to opposite sides of the base of the foot. The first channel can have a different diameter than the second channel. The elongate conduit can include a third channel, the third channel ending in a third channel head, the third channel head being configured to be mounted to a different part of the base of the foot than the first channel head and the second channel head. The first channel head can be mounted to a ball of the foot, the second channel head can be mounted to an outer surface of the foot, and the third channel head can be mounted to a heel of the foot. The pressure sensor can measure the pressure at an opposite end of the elongate conduit from the conduit head. The apparatus can further include a housing configured to support the pressure sensor and the controller. The housing can be a worn on a hip or a leg of the individual. The elongate conduit can include one or more layers. The one or more layers can include one or more sheets. The one or more layers can include a plurality of flat surfaces. The elongate conduit can include a flat tube. The apparatus can further include a user interface configured to present the indication. The user interface can audibly present the indication. The user interface can visually present the indication. The apparatus can further include a transmitter configured to wirelessly transmit the indication. The internal volume can be at least partially filled with a liquid. The internal volume can be at least partially filled with air. The internal volume can be at least partially filled with a gas other than air. A portion of the conduit head can be coated with an adhesive to assist with attachment of the elongate conduit to the foot. The conduit head can include foam. The elongate conduit can extend around and along a leg of the individual. The elongate conduit can include a tube having a diameter between 10 mm and 100 mm. The period of time can be at least one second. The pressure can be less than atmospheric pressure when the conduit head is unloaded. The pressure can be greater than atmospheric pressure when the conduit head is loaded with the threshold amount of weight. The elongate conduit can be sealed off from an environment external to the elongate conduit. The elongate conduit can include a leak path, such as a controlled leak path, configured to communicate the gas from the internal volume to an environment external to the elongate conduit. The leak path can include a hole or a valve, such as a check valve.

A method of manufacturing or operating the apparatus of preceding two paragraphs is additionally disclosed.

In some embodiments, an apparatus for monitoring load bearing of a body part of an individual is disclosed. The apparatus can include an elongate conduit, a pressure sensor, and a controller. The elongate conduit can include a conduit head configured to attach to a body part of an individual, the elongate conduit being collapsible and having an internal volume, the internal volume being configured to retain a gas or a liquid within the internal volume. The pressure sensor can measure a pressure within the internal volume. The controller can: determine, from a change in the pressure over a period of time, that the body part is supporting a threshold amount of weight within the period of time, and output for presentation an indication in response to determining that the body part is supporting the threshold amount of weight within the period of time. The body part can be a foot, a back, a hip, or a thigh. A method of manufacturing or operating the apparatus of this paragraph is also disclosed.

In some embodiments, a system for monitoring load bearing is disclosed. The system can include a housing and a controller. The housing can attach to a leg of an individual below a knee of the individual and support a motion sensor. The motion sensor can generate a signal responsive to motion of the leg during a time period. The controller can: calculate a frequency transform of the signal to obtain a spectral distribution of the signal, determine an activity classification from the spectral distribution, the activity classification being indicative of a type of activity engaged in by the individual while wearing the motion sensor during the time period, and output for presentation an indication of the activity classification.

The system of the preceding paragraph can include one or more of the following features: The activity classification can be one of driving, sitting, or walking. The controller can determine the activity classification from a comparison of (i) a first amplitude of the spectral distribution over a first frequency range and (ii) a second amplitude of the spectral distribution over a second frequency range different from the first frequency range. The controller can determine the activity classification is walking rather than sitting from the comparison. The controller can determine the activity classification is sitting rather than walking from the comparison. The comparison can be a ratio. The controller can determine the activity classification is sitting when the ratio is within a first range of values, and the controller is configured to determine the activity classification is walking when the ratio is within a second range of values different from the first range of values. The housing can be attached to a top of a foot of the leg. The housing can be attached beneath and proximate to the knee. The controller can determine a position of the leg during the time period from the signal. The controller can determine the activity classification further from the position. The controller can determine a pressure on a foot of the leg from a magnitude of the signal. The controller can determine the pressure on the foot from an absolute magnitude of the signal in a plurality of axes. The system can further include a pressure sensor configured to be positioned beneath a foot of the leg, and the controller can determine the activity classification further from an output of the pressure sensor. The system can further include a textile foot cover configured to support the housing and the pressure sensor. The system can further include an absolute pressure sensor configured to detect a change in altitude of the leg, and the controller can determine the activity classification further from an output of the absolute pressure sensor. The system can further include a user interface configured to visually or audibly present the indication of the activity classification. The controller can determine the activity classification further from a magnitude of the signal. The controller can determine the activity classification further from an angular response of the leg. The frequency transform can include a fast Fourier transform. The motion sensor can include an accelerometer. The housing can support the controller.

A method of manufacturing or operating the system of preceding two paragraphs is additionally disclosed.

In some embodiments, a system for monitoring load bearing is disclosed. The system can include a housing and a controller. The housing can attach to a leg of an individual below a knee of the individual and support a motion sensor. The motion sensor can generate a signal responsive to motion of the leg during a first time period and a second time period. The controller can: determine that the leg is supporting a weight during the first time period based at least on motion during the first time period reflecting a muscle tremor by the leg that occurs when the leg is not supporting at least a baseline amount of weight, determine that the leg is not supporting the weight during the second time period based at least on motion during the second time period not reflecting the muscle tremor by the leg that occurs when the leg is not supporting at least the baseline amount of weight, and responsive to determining that the leg is not supporting the weight during the second time period, output for presentation an indication denoting to move the foot.

The system of the preceding paragraph can include one or more of the following features: The controller can, prior to determining that the leg is supporting the weight during the first time period and not supporting the weight during the second time period, profile the muscle tremor by the leg that occurs when the leg is not supporting at least the baseline amount of weight. The controller can determine a degree to which motion during the first time period reflects the muscle tremor by the leg that occurs when the leg is not supporting at least the baseline amount of weight. The controller can determine a value from the degree, the value being indicative of a magnitude of the weight supported by the leg during the first time period. The controller can output the value for presentation. The controller can filter a vehicle motion from the signal. The vehicle motion can include a car motion, a lorry motion, an airplane motion, or a train motion. The motion sensor can be an accelerometer.

A method of manufacturing or operating the system of preceding two paragraphs is additionally disclosed.

In some embodiments, a system for monitoring load bearing of a foot is disclosed. The system can include a negative pressure source, a pressure sensor, a motion sensor, and a controller. The negative pressure source can provide negative pressure via a fluid flow path under a dressing, the dressing being positioned over at least a portion of the foot. The pressure sensor can monitor pressure in the fluid flow path. The motion sensor can monitor motion of the foot. The controller can: determine, from a first change in the pressure in the fluid flow path, that the foot has been loaded to support a threshold amount of weight; determine, from (i) the first change in the pressure or a second change in the pressure subsequent to the first change in the pressure and (ii) a change in the motion, a duration of time over which the foot is loaded; and output for presentation the duration of time over which the foot is loaded.

The system of the preceding paragraph can include one or more of the following features: The negative pressure source can maintain substantially a target negative pressure under the dressing, and the controller can determine that the foot has been loaded to support the threshold amount of weight from determining that substantially the target negative pressure has been reestablished under the dressing in response to the loading of the foot. Loading of the foot can cause decrease in negative pressure under the dressing, and the negative pressure source can counteract the decrease in negative pressure by reestablishing substantially the target negative pressure under the dressing. The controller can further, subsequent to determining that the foot has been loaded, determine, from the second change in the pressure in the fluid flow path, that the foot has been unloaded. Unloading of the foot can cause increase in the negative pressure under the dressing. The controller can further classify, from the at least one change in the motion, foot activity over the time duration; and output for presentation the activity classification. The activity classification can include one or more of standing, walking, jumping, running, or climbing stairs. The motion sensor can be an accelerometer. The accelerometer can measure one or more changes in position of the foot relative to a support surface. The controller can classify the activity as standing in response to determining substantially no changes in a position of the foot relative to a support surface subsequent to determining that the foot has been loaded. The controller can classify the activity as walking, jumping, running, or climbing stairs in response to determining that a position of the foot relative to a support surface periodically exceeds a walking, jumping, running, or climbing stairs position threshold over the time duration. The controller can classify the activity as walking, jumping, running, or climbing stairs further in response to determining that monitored pressure periodically exceeds a walking, jumping, running, or climbing stairs pressure threshold over the time duration. The walking pressure threshold can be smaller than the jumping, running, or climbing stairs pressure thresholds. The pressure sensor can be positioned in the fluid flow path outside the foot. The pressure sensor can be positioned under the dressing. The motion sensor can be positioned outside the foot. The motion sensor can be positioned under the dressing. The controller can wirelessly output for presentation the duration of time over which the foot is loaded. The controller can further determine, from the first change in the pressure in the fluid flow path and the change in the motion, that the foot has been loaded to support the threshold amount of weight. The controller can further use the change in the motion to distinguish a decrease in negative pressure under the dressing associated with loading of the foot from a decrease in negative pressure under the dressing associated with a leak in the fluid flow path. The change in the motion can be caused by the loading of the foot.

A method of manufacturing or operating the system of preceding two paragraphs is additionally disclosed.

In some embodiments, a system for monitoring use of an orthopedic device is disclosed. The system can include an orthopedic device, a housing, and a controller. The orthopedic device can provide support to a limb of an individual and can include a magnet configured to generate a magnetic field. The housing can be attached to the individual and support a magnetometer configured to generate a signal responsive to the magnetic field. The controller can: determine from the signal that the individual is using the orthopedic device to provide support to the limb during a first time period; in response to determining that the individual is using the orthopedic device during the first time period, output a first indication; determine from the signal that the individual is not using the orthopedic device to provide support to the limb during a second time period; and in response to determining that the individual is not using the orthopedic device during the second time period, output a second indication.

The system of the preceding paragraph can include one or more of the following features: The controller can determine from a first change in a magnitude of the signal during the first time period that the individual is using the orthopedic device to provide support to the limb during the first time period, and the controller can determine from a second change in a magnitude of the signal during the second time period that the individual is not using the orthopedic device to provide support to the limb during the second time period. The first change in the magnitude can be greater than the second change in the magnitude (such as if the magnitude is generated by compression of an element) or less than the second magnitude (such as if the magnitude is generated by a distance between the magnet and the magnetometer). The controller can determine from a first periodicity of the signal during the first time period that the individual is using the orthopedic device to provide support to the limb during the first time period, and the controller can determine from a second periodicity of the signal during the second time period that the individual is not using the orthopedic device to provide support to the limb during the second time period. The first periodicity can be greater or less than the second periodicity (for instance, a periodicity matching a leg motion periodicity during walking can correspond to use while a periodicity below or above a leg motion periodicity during walking can correspond to nonuse of the orthopedic device). The controller can determine from the signal that the orthopedic device is not properly fitted to provide support to the limb during the first time period (for instance, an offset behavior may be observed if the orthopedic device is loose—the orthopedic device can hit the ground first and thus may be closer to the magnetometer, then the limb can hit the ground and the signal may remain static for a period of time, next the limb can lift first, and subsequently followed by lifting of the orthopedic device); and in response to determining that the orthopedic device is not properly fitted to provide support to the limb during the first time period, output a third indication. The controller can determine from a directionality of a magnetic field of the signal that the orthopedic device is not properly fitted to provide support to the limb during the first time period. The magnet can include a permanent magnet. The limb can be a leg. The orthopedic device can offload weight placed on the limb. The magnet can have a field strength greater than 100

µT at a distance of 50 cm from the magnet. The controller can determine an orientation of the magnetometer with respect to a magnetic north of Earth. The orthopedic device can include a first accelerometer configured to generate first motion data, and the housing can support a second accelerometer configured to generate second motion data, the controller being configured to determine further from a comparison of the first motion data and the second motion data that the individual is using the orthopedic device to provide support to the limb during the first time period. The controller can determine from the comparison that the orthopedic device is not properly fitted to provide support to the limb during the first time period; and in response to determining that the orthopedic device is not properly fitted to provide support to the limb during the first time period, output a third indication. The orthopedic device can include a boot or cast. The orthopedic device can include a pressure sensor configured to generate pressure data, and the controller can determine further from the pressure data that the individual is using the orthopedic device to provide support to the limb during the first time period. The orthopedic device can include an optical switch configured to generate optical data, and the controller can determine further from the optical data that the individual is using the orthopedic device to provide support to the limb during the first time period. The orthopedic device can include a detector configured to generate electromagnetic radiation data responsive to detected electromagnetic radiation, and the controller can determine further from a signal strength of the electromagnetic radiation data that the individual is using the orthopedic device to provide support to the limb during the first time period.

A method of manufacturing or operating the system of preceding two paragraphs is additionally disclosed. Moreover, although the system of the preceding two paragraphs may be described with the orthopedic device including the magnet and the housing supporting the magnetometer, the orthopedic device can instead include or support the magnetometer and the orthopedic device can include the magnet.

In some embodiments, a method for monitoring use of an orthopedic device is disclosed. The method can include: generating a signal responsive to a magnetic field with a magnetometer that is supported by a housing attached to an individual, the magnetic field being generated by a magnet attached to an orthopedic device that is configured to support a limb of the individual; determining from the signal that the individual is using the orthopedic device to provide support to the limb during a first time period; in response to determining that the individual is using the orthopedic device during the first time period, outputting a first indication; determining from the signal that the individual is not using the orthopedic device to provide support to the limb during a second time period; and in response to determining that the individual is not using the orthopedic device during the second time period, outputting a second indication.

The method of the preceding paragraph can include one or more of the following features: A first change in a magnitude of the signal during the first time period can be at least used to determine that the individual is using the orthopedic device to provide support to the limb during the first time period, and a second change in a magnitude of the signal during the second time period can be at least used to that the individual is not using the orthopedic device to provide support to the limb during the second time period. The first magnitude can be greater or less than the second magnitude. A first periodicity of the signal during the first time period can be at least used to determine that the individual is using the orthopedic device to provide support to the limb during the first time period, and a second periodicity of the signal during the second time period can be at least used to that the individual is not using the orthopedic device to provide support to the limb during the second time period. The first periodicity can be greater or less than the second periodicity. The method can further include: determining from the signal that the orthopedic device is not properly fitted to provide support to the limb during the first time period; and in response to determining that the orthopedic device is not properly fitted to provide support to the limb during the first time period, outputting a third indication. A field directionality of the signal can be at least used to determine that the orthopedic device is not properly fitted to provide support to the limb during the first time period.

BRIEF DESCRIPTION OF THE DRAWINGS

Embodiments of the present disclosure will now be described hereinafter, by way of example only, with reference to the accompanying drawings in which.

DETAILED DESCRIPTION

Introduction to Wound Monitoring and Therapy

Figure 1:
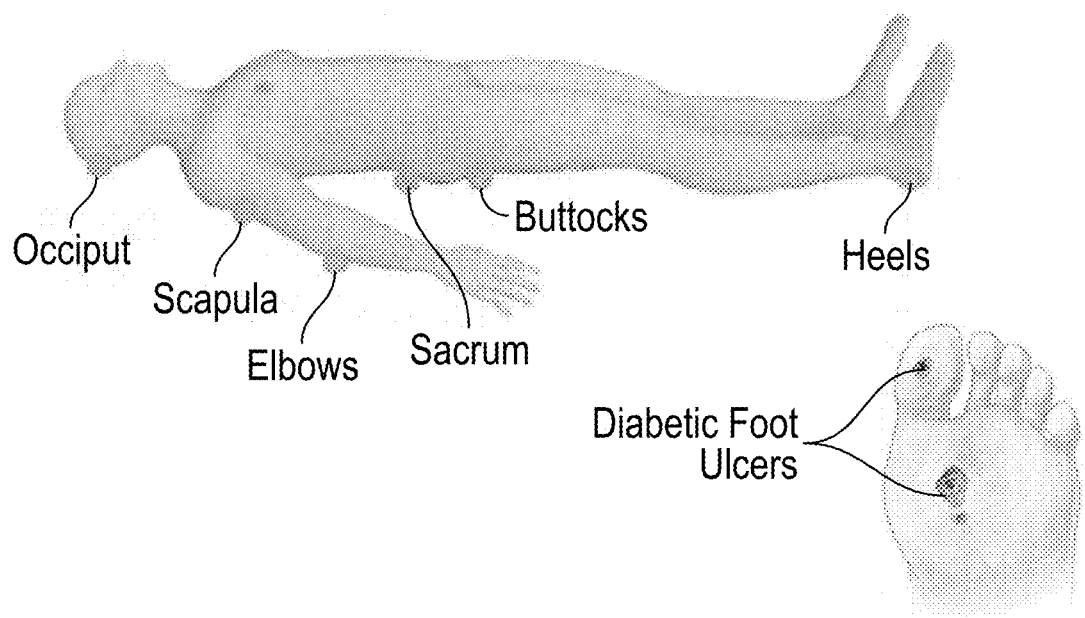
FIG. 1 illustrates pressure ulcers including to diabetic foot ulcers according to the prior art.

Embodiments disclosed herein relate to apparatuses, systems, and methods for the monitoring of body loading and body position for treatment of pressure ulcers. Loading can refer to transferring or placing at least a threshold amount of force on a body part. Placing such threshold amount of force on the body part causes the body part to support weight. For example, loading of a foot can refer to transferring or placing at least a portion of the body weight (or body weight in combination with external weight) on the foot such that the foot is supporting at least such portion of the body weight. At least such portion of the body weight can serve as a threshold for determining that the foot has been loaded.

Some of the disclosed implementations utilize a dressing (also sometimes referred to as wound dressing) alone or in combination with negative or reduced pressure. The apparatuses and components including an overlay and packing materials or internal layers, if any, are sometimes collectively referred to herein as dressings.

Some embodiments disclosed herein relate to wound monitoring or therapy for a human or animal body. Therefore, any reference to a wound herein can refer to a wound on a human or animal body, and any reference to a body herein can refer to a human or animal body. The disclosed technology embodiments may relate to preventing or minimizing damage to physiological tissue or living tissue, or to the treatment of damaged tissue (for example, a wound as described herein).

As used herein the expression "wound" may include an injury to living tissue may be caused by a cut, blow, or other impact, typically one in which the skin is cut or broken. A wound may be a chronic or acute injury. Acute wounds occur as a result of surgery or trauma. They move through the stages of healing within a predicted timeframe. Chronic wounds typically begin as acute wounds. The acute wound can become a chronic wound when it does not follow the healing stages resulting in a lengthened recovery. It is believed that the transition from acute to chronic wound can be due to a patient being immuno-compromised.

Chronic wounds may include for example: venous ulcers (such as those that occur in the legs), which account for the majority of chronic wounds and mostly affect the elderly, diabetic ulcers (for example, foot or ankle ulcers), peripheral arterial disease, pressure ulcers, or epidermolysis bullosa (EB).

Examples of other wounds include, but are not limited to, abdominal wounds or other large or incisional wounds (either as a result of surgery, trauma, sterniotomies, fasciotomies, or other conditions), dehisced wounds, acute wounds, chronic wounds, subacute and dehisced wounds, traumatic wounds (such as from orthopaedic trauma), flaps and skin grafts, lacerations, abrasions, contusions, burns, diabetic ulcers, pressure ulcers, stoma, surgical wounds, trauma and venous ulcers, broken bones or the like.

Wounds may also include a deep tissue injury. Deep tissue injury is a term proposed by the National Pressure Ulcer Advisory Panel (NPUAP) to describe a unique form of pressure ulcers. These ulcers have been described by clinicians for many years with terms such as purple pressure ulcers, ulcers that are likely to deteriorate and bruises on bony prominences.

Wound may also include tissue at risk of becoming a wound as discussed herein. For example, tissue at risk may include tissue over a bony protuberance (at risk of deep tissue injury/insult) or pre-surgical tissue (for example, knee tissue) that may has the potential to be cut (for example, for joint replacement/surgical alteration/reconstruction).

Some embodiments relate to methods of monitoring or treating a wound with the technology disclosed herein in conjunction with one or more of the following: advanced footwear, turning a patient, offloading (such as, offloading diabetic foot ulcers), treatment of infection, systemix, antimicrobial, antibiotics, surgery, removal of tissue, affecting blood flow, physiotherapy, exercise, bathing, nutrition, hydration, nerve stimulation, ultrasound, electrostimulation, oxygen therapy, microwave therapy, active agents ozone, antibiotics, antimicrobials, or the like.

Alternatively or additionally, a wound may be treated using topical negative pressure or traditional advanced wound care, which is not aided by the using of applied negative pressure (may also be referred to as non-negative pressure therapy).

Advanced wound care may include use of an absorbent dressing, an occlusive dressing, use of an antimicrobial or debriding agents in a wound dressing or adjunct, a pad (for example, a cushioning or compressive therapy, such as stockings or bandages), or the like.

In some embodiments, treatment of such wounds can be performed using traditional wound care, wherein a dressing can be applied to the wound to facilitate and promote healing of the wound.

Some embodiments relate to methods of manufacturing a wound dressing including providing a wound dressing as disclosed herein.

The wound dressings that may be utilized in conjunction with the disclosed technology include any known dressing in the art. The technology is applicable to negative pressure therapy treatment as well as non-negative pressure therapy treatment.

In some embodiments, a wound dressing includes one or more absorbent layer(s). The absorbent layer may be a foam or a superabsorbent.

In some embodiments, wound dressings may include a dressing layer including a polysaccharide or modified polysaccharide, a polyvinylpyrrolidone, a polyvinyl alcohol, a polyvinyl ether, a polyurethane, a polyacrylate, a polyacrylamide, collagen, or gelatin or mixtures thereof. Dressing layers including the polymers listed are known in the art as being useful for forming a wound dressing layer for either negative pressure therapy or non-negative pressure therapy.

In some embodiments, a wound dressing also includes a top or cover layer.

The thickness of the wound dressing disclosed herein may be between 1 to 20, or 2 to 10, or 3 to 7 mm.

In some embodiments, the disclosed technology may be used in conjunction with a non-negative pressure dressing. A non-negative pressure wound dressing suitable for providing protection at a wound site may include: an absorbent layer for absorbing wound exudate and an obscuring element for at least partially obscuring a view of wound exudate absorbed by the absorbent layer in use. The obscuring element may be partially translucent. The obscuring element may be a masking layer.

Wound Dressing for Use with Wound Therapy

Treatment of such wounds can be performed using reduced or negative pressure wound therapy, wherein pressure can be applied to the wound to facilitate and promote healing of the wound. It will also be appreciated that the wound dressing and methods as disclosed herein may be applied to other parts of the body, and are not necessarily limited to treatment of wounds.

It will be understood that embodiments of the present disclosure are generally applicable to use in topical negative pressure ("TNP") therapy systems. Briefly, negative pressure wound therapy assists in the closure and healing of many forms of "hard to heal" wounds by reducing tissue oedema; encouraging blood flow and granular tissue formation; removing excess exudate and may reduce bacterial load (and thus infection risk). In addition, the therapy allows for less disturbance of a wound leading to more rapid healing. TNP therapy systems may also assist on the healing of surgically closed wounds by removing fluid and by helping to stabilize the tissue in the apposed position of closure. A further beneficial use of TNP therapy can be found in grafts and flaps where removal of excess fluid is important and close proximity of the graft to tissue is required in order to ensure tissue viability.

Negative pressure therapy can be used for the treatment of open or chronic wounds that are too large to spontaneously close or otherwise fail to heal by means of applying negative pressure to the site of the wound. Topical negative pressure (TNP) therapy or negative pressure wound therapy ("NPWT") involves placing a cover that is impermeable or semi-permeable to fluids over the wound, using various means to seal the cover to the tissue of the patient surrounding the wound, and connecting a source of negative pressure (such as a vacuum pump) to the cover in a manner so that negative pressure is created and maintained under the cover. It is believed that such negative pressures promote wound healing by facilitating the formation of granulation tissue at the wound site and assisting the body's normal inflammatory process while simultaneously removing excess fluid, which may contain adverse cytokines or bacteria.

As is used herein, reduced or negative pressure levels, such as $-X$ mmHg, represent pressure levels relative to normal ambient atmospheric pressure, which can correspond to 760 mmHg (or 1 atm, 29.93 inHg, 101.325 kPa, 14.696 psi, etc.). Accordingly, a negative pressure value of $-X$ mmHg reflects absolute pressure that is X mmHg below 760 mmHg or, in other words, an absolute pressure of (760-X) mmHg. In addition, negative pressure that is "less" or "smaller" than X mmHg corresponds to pressure that is closer to atmospheric pressure (such as, $-40$ mmHg is less than $-60$ mmHg). Negative pressure that is "more" or "greater" than $-X$ mmHg corresponds to pressure that is further from atmospheric pressure (such as, $-80$ mmHg is more than $-60$ mmHg). In some embodiments, local ambient atmospheric pressure is used as a reference point, and such local atmospheric pressure may not necessarily be, for example, 760 mmHg.

Negative Pressure Wound Therapy System

Figure 2:
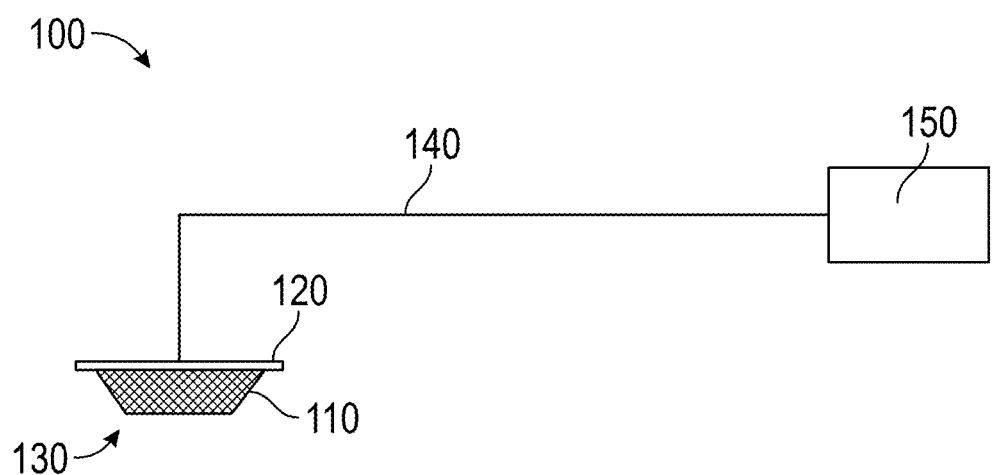
FIG. 2 illustrates a negative pressure wound therapy system according to some embodiments.

FIG. 2 illustrates an embodiment of a negative pressure wound therapy system 100 including a wound filler 130 placed inside a wound cavity 110, the wound cavity sealed by a wound cover 120. The wound filler 130 in combination with the wound cover 120 can be referred to as wound dressing. A single or multi lumen tube or conduit 140 is connected the wound cover 120 with a pump assembly 150 configured to supply reduced pressure. The wound cover 120 can be in fluidic communication with the wound cavity 110. In any of the system embodiments disclosed herein, as in the embodiment illustrated in FIG. 2, the pump assembly can be a canisterless pump assembly (meaning that exudate is collected in the wound dressing is transferred via conduit 140 for collection to another location). However, any of the pump assembly embodiments disclosed herein can be configured to include or support a canister. Additionally, in any of the system embodiments disclosed herein, any of the pump assembly embodiments can be mounted to or supported by the dressing, or adjacent to the dressing. The wound filler 130 can be any suitable type, such as hydrophilic or hydrophobic foam, gauze, inflatable bag, and so on. The wound filler 130 can be conformable to the wound cavity 110 such that it substantially fills the cavity at atmospheric pressure, and also may have a substantially reduced compressed volume when under negative pressure. The wound cover 120 can provide a substantially fluid impermeable seal over the wound cavity 110. In some embodiments, the wound cover 120 has a top side and a bottom side, and the bottom side adhesively (or in any other suitable manner) seals with wound cavity 110. The conduit 140 or any other conduit disclosed herein can be formed from polyurethane, PVC, nylon, polyethylene, silicone, or any other suitable material.

Some embodiments of the wound cover 120 can have a port (not shown) configured to receive an end of the conduit 140. In some embodiments, the conduit 140 can otherwise pass through or under the wound cover 120 to supply reduced pressure to the wound cavity 110 so as to maintain a desired level of reduced pressure in the wound cavity. The conduit 140 can be any suitable article configured to provide at least a substantially sealed fluid flow pathway between the pump assembly 150 and the wound cover 120, so as to supply the reduced pressure provided by the pump assembly 150 to wound cavity 110.

The wound cover 120 and the wound filler 130 can be provided as a single article or an integrated single unit. In some embodiments, no wound filler is provided and the wound cover by itself may be considered the wound dressing. The wound dressing may then be connected, via the conduit 140, to a source of negative pressure, such as the pump assembly 150. In some embodiments, though not required, the pump assembly 150 can be miniaturized and portable, although larger conventional pumps such can also be used.

The wound cover 120 can be located over a wound site to be treated. The wound cover 120 can form a substantially sealed cavity or enclosure over the wound site. In some embodiments, the wound cover 120 can be configured to have a film having a high water vapour permeability to enable the evaporation of surplus fluid, and can have a superabsorbing material contained therein to safely absorb wound exudate. It will be appreciated that throughout this specification reference is made to a wound. In this sense it is to be understood that the term wound is to be broadly construed and encompasses open and closed wounds in which skin is torn, cut or punctured or where trauma causes a contusion, or any other surficial or other conditions or imperfections on the skin of a patient or otherwise that benefit from reduced pressure treatment. A wound is thus broadly defined as any damaged region of tissue where fluid may or may not be produced. In some embodiments, the components of the TNP system described herein can be particularly suited for incisional wounds that exude a small amount of wound exudate.

Some embodiments of the system are designed to operate without the use of an exudate canister. Some embodiments can be configured to support an exudate canister. In some embodiments, configuring the pump assembly 150 and conduit 140 so that the conduit 140 can be quickly and easily removed from the pump assembly 150 can facilitate or improve the process of dressing or pump changes, if necessary. Any of the pump embodiments disclosed herein can be configured to have any suitable connection between the tubing and the pump.

In some embodiments, the pump assembly 150 can be configured to deliver negative pressure at a desired or target negative pressure setpoint or range as described herein.

In some embodiments, the pump assembly 150 is configured to provide continuous or intermittent negative pressure therapy. Continuous therapy can be delivered at above −25 mmHg, −25 mmHg, −40 mmHg, −50 mmHg, −60 mmHg, −70 mmHg, −80 mmHg, −90 mmHg, −100 mmHg, −120 mmHg, −140 mmHg, −160 mmHg, −180 mmHg, −200 mmHg, or below −200 mmHg. Intermittent therapy can be delivered between low and high negative pressure set points. Low set point can be set at above 0 mmHg, 0 mmHg, −25 mmHg, −40 mmHg, −50 mmHg, −60 mmHg, −70 mmHg, −80 mmHg, −90 mmHg, −100 mmHg, −120 mmHg, −140 mmHg, −160 mmHg, −180 mmHg, or below −180 mmHg. High set point can be set at above −25 mmHg, −40 mmHg, −50 mmHg, −60 mmHg, −70 mmHg, −80 mmHg, −90 mmHg, −100 mmHg, −120 mmHg, −140 mmHg, −160 mmHg, −180 mmHg, −200 mmHg, or below −200 mmHg. During intermittent therapy, negative pressure at low set point can be delivered for a first time duration, and upon expiration of the first time duration, negative pressure at high set point can be delivered for a second time duration. Upon expiration of the second time duration, negative pressure at low set point can be delivered. The first and second time durations can be same or different values. The first and second durations can be selected from the following range: less than 2 minutes, 2 minutes, 3 minutes, 4 minutes, 6 minutes, 8 minutes, 10 minutes, or greater than 10 minutes. In some embodiments, switching between low and high set points and vice versa can be performed according to a step waveform, square waveform, sinusoidal waveform, and the like.

In operation, the wound filler 130 is inserted into the wound cavity 110 and wound cover 120 is placed so as to seal the wound cavity 110. The pump assembly 150 provides a source of a negative pressure to the wound cover 120, which is transmitted to the wound cavity 110 via the wound filler 130. Fluid (for example, wound exudate) is drawn through the conduit 140, and can be stored in a canister. In some embodiments, fluid is absorbed by the wound filler 130 or one or more absorbent layers (not shown).

Wound dressings that may be utilized with the pump assembly and other embodiments of the present application include any of the dressings described herein, such as RENASYS-F, RENASYS-G, RENASYS-AB, and RENASYS-F/AB, and PICO dressings available from Smith & Nephew. Further description of such wound dressings and other components of a negative pressure wound therapy system that may be used with the pump assembly and other embodiments of the present application are found in U.S. Patent Publication Nos. 2012/0116334, 2011/0213287, 2011/0282309, 2012/0136325, 2013/0110058, which are incorporated by reference in their entireties. In other embodiments, other suitable wound dressings can be utilized.

Figure 3A:
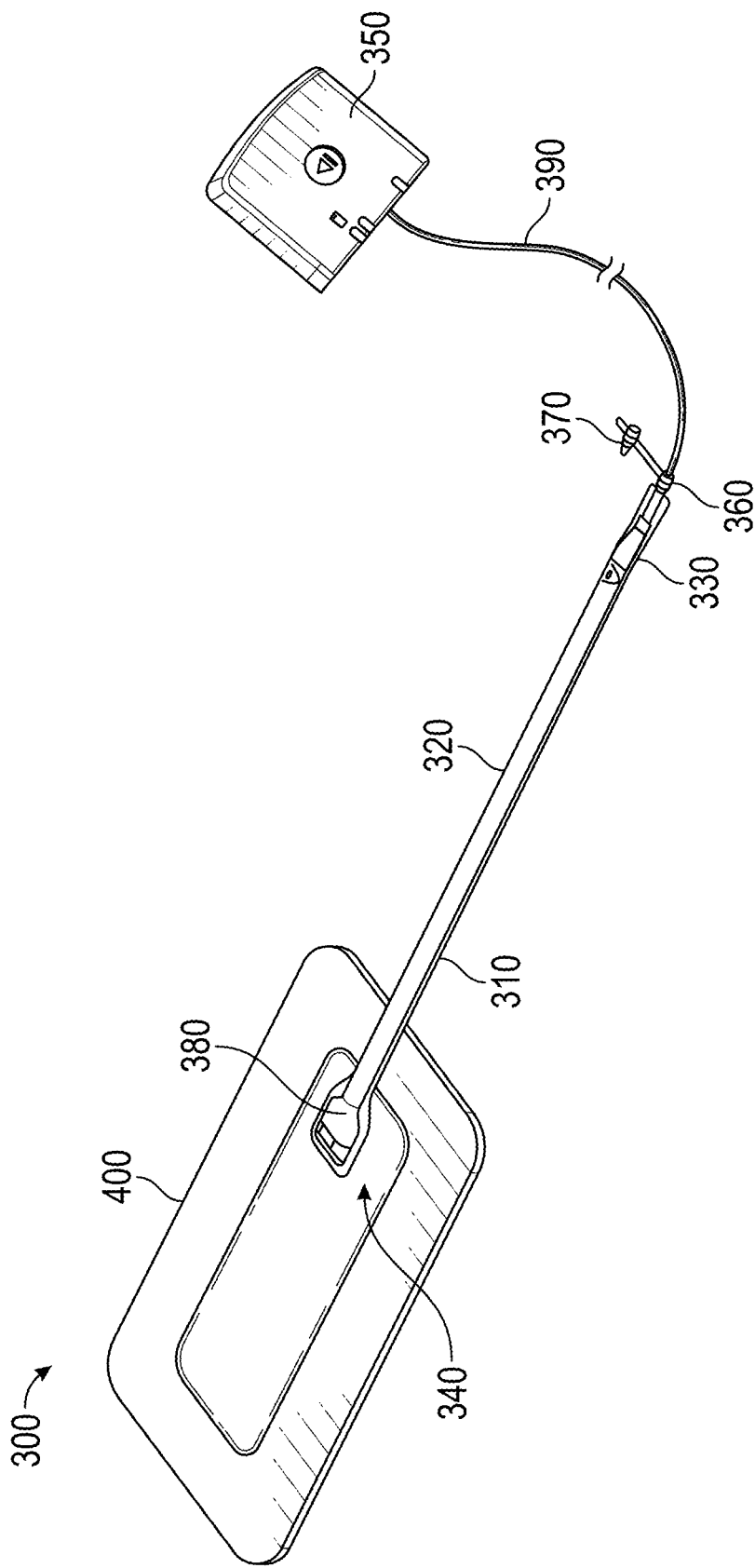
FIGS. 3A and 3B illustrate negative pressure wound therapy system according to some embodiments.
Figure 3B:
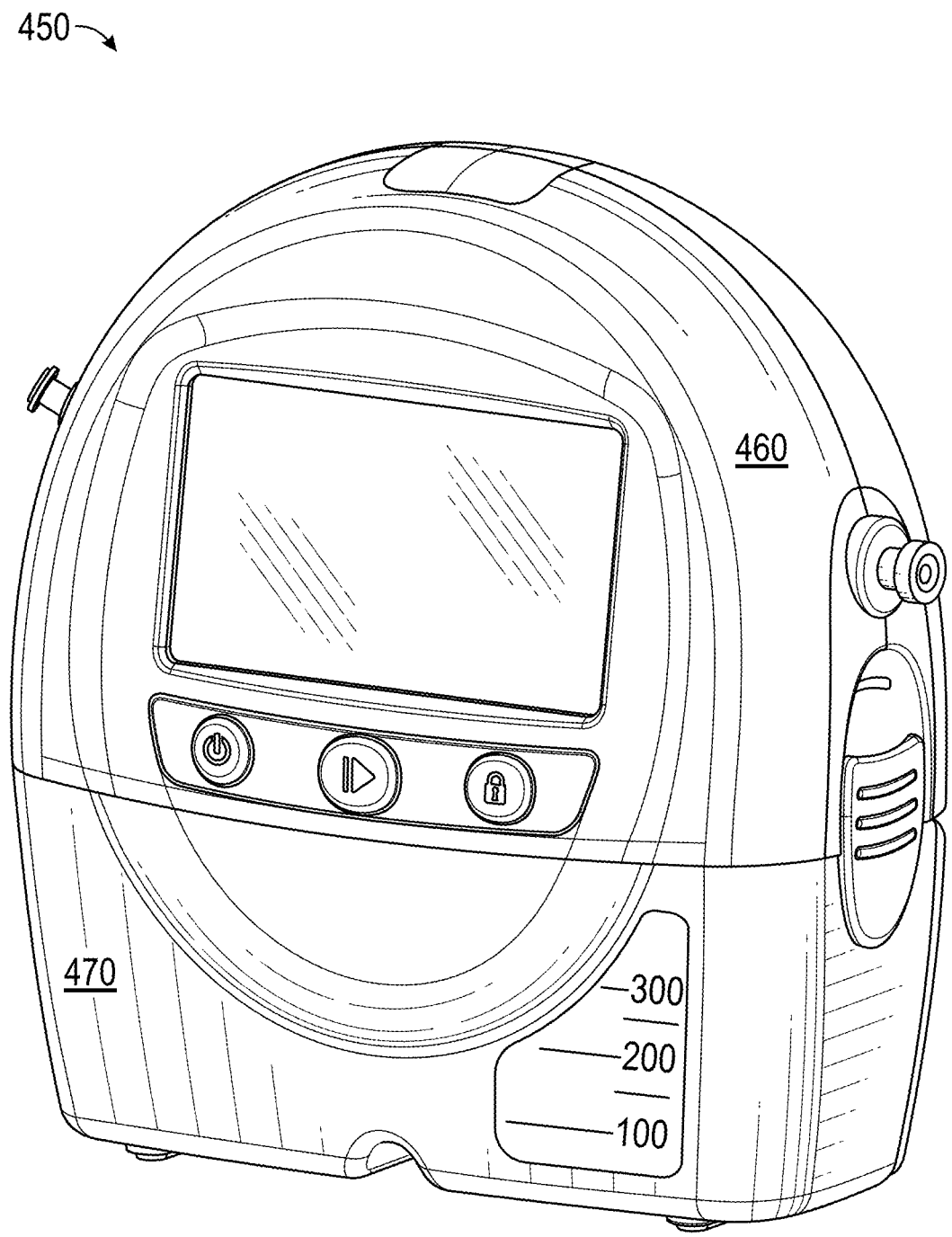

FIGS. 3A-3B illustrate negative pressure wound therapy system according to some embodiments. With reference to FIG. 3A, the system 300 illustrates a dressing 400, such as a wound dressing, in conjunction with a fluidic connector 310. The illustrated fluidic connector can correspond to SOFT PORT connector available from Smith & Nephew. In some cases, a different connector can be used in the system 300.

The illustrated fluidic connector 310 can include an elongate conduit, more preferably a bridge 320 having a proximal end 330 and a distal end 340, and an applicator 380 at the distal end 340 of the bridge 320. An optional coupling 360 is preferably disposed at the proximal end 330 of the bridge 320. A cap 370 may be provided with the system (and can in some cases, as illustrated, be attached to the coupling 360). The cap 370 can be useful in preventing fluids from leaking out of the proximal end 330.

The system 300 can include a negative pressure source, such as a pump or negative pressure source 350 capable of supplying negative pressure. The negative pressure source can include a canister (as illustrated in FIG. 3B) or other container for the storage of wound exudates and other fluids that may be removed from the wound. A canister or container may also be provided separate from the negative pressure source. In some embodiments, such as illustrated in FIG. 3A, the negative pressure source 350 can be a canisterless pump, such as the PICO pump available from Smith & Nephew. The dressing 400 can be an absorbent dressing, such as the PICO dressing available from Smith & Nephew. The negative pressure source 350 can be connected to the coupling 360 via a tube 390, or the negative pressure source 350 can be connected directly to the coupling 360 or directly to the bridge 320.

In use, the dressing 400 is placed over a suitably-prepared wound, which may in some cases be filled with a wound packing material such as foam or gauze. The applicator 380 of the fluidic connector 310 has a sealing surface that is placed over an aperture in the dressing 400 and is sealed to the top surface of the dressing 400. Either before, during, or after connection of the fluidic connector 310 to the dressing 400, the negative pressure source 350 is connected via the tube 390 to the coupling 360, or is connected directly to the coupling 360 or to the bridge 320. The negative pressure source 350 is then activated, thereby supplying negative pressure to the wound. Application of negative pressure may be applied until a desired level of healing of the wound is achieved.

FIG. 3B illustrates a negative pressure source 450 that includes a device unit 460 and canister 470. The device unit includes a negative pressure source, electronics, user interface, and the like. The illustrated negative pressure source 450 can be a RENASYS TOUCH or RENAYS CONNECT pump available from Smith & Nephew. The negative pressure source 450 can be used in the system 300 in place of the pump assembly 150. The negative pressure source 450 (or 150) can be used with the dressing 400 or another suitable dressing, such as Renasys-F foam dressing or Renasys-G gauze dressing available from Smith & Nephew.

Load Monitoring System

Figure 4:
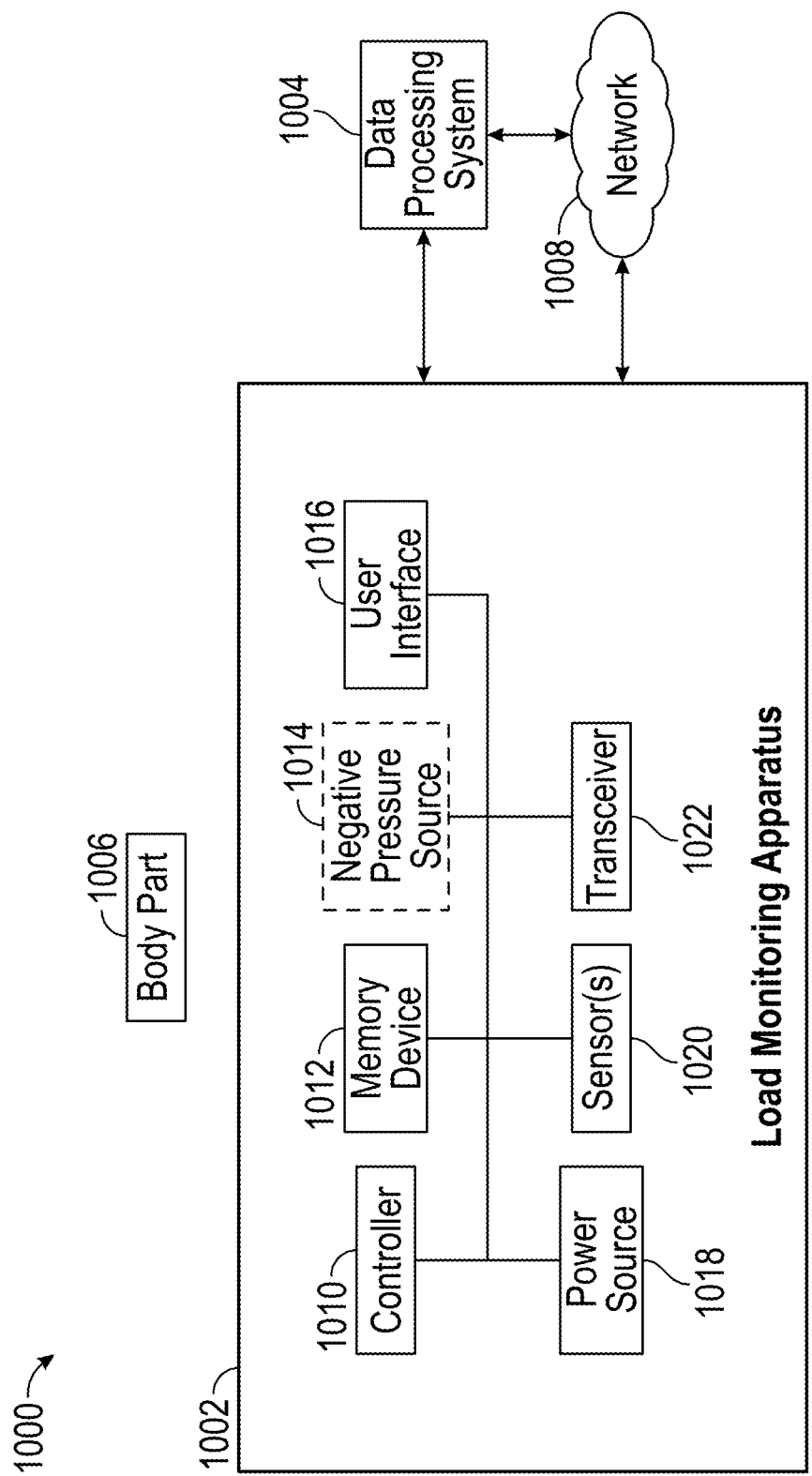
FIG. 4 illustrates a monitoring system that includes a load monitoring apparatus and a data processing system according to some embodiments.

FIG. 4 illustrates a monitoring system 1000 that includes a load monitoring apparatus 1002 and a data processing system 1004. The load monitoring apparatus 1002 can be used to monitor loading or positioning of a body part 1006, such as a foot of a patient of a body. The load monitoring apparatus 1002 can include a controller 1010, a memory device 1012, a user interface 1016, a power source 1018, one or more sensors 1020, and a transceiver 1022 that are configured to communicate with one another. The power source 1018 can provide power to one or more components of the load monitoring apparatus 1002.

The load monitoring apparatus 1002 can be attached to the body using a strap, adhesive, or other coupling mechanism and may be worn on or supported by the body. In some embodiments, the load monitoring apparatus 1002 can be used in combination with negative pressure wound therapy and may further include a negative pressure source 1014.

The controller 1010 can control operations of one or more other components of the load monitoring apparatus 1002 according at least to instructions stored in the memory device 1012. The controller 1010 can, for instance, control monitoring of loading of the body part 1006 with a weight of the body or positioning of the body part 1006. In some embodiments, the controller 1010 can control operations of the negative pressure source and supply of negative pressure with the negative pressure source 1014. The negative pressure source 1014 can include a pump, such as, without limitation, a rotary diaphragm pump or other diaphragm pump, a piezoelectric pump, a peristaltic pump, a piston pump, a rotary vane pump, a liquid ring pump, a scroll pump, a diaphragm pump operated by a piezoelectric transducer, or any other suitable pump or micropump or any combinations of the foregoing.

The user interface 1016 can include one or more elements that receive user inputs or provide user outputs to the patient or a caregiver. The one or more elements that receive user inputs can include buttons, switches, dials, touch screens, or the like. The user interface 1016 can, for example, communicate information about loading or positioning of the body part 1006, such as a suggested action to prevent formation of a pressure ulcer on the body part 1006 or mitigate damage to an existing pressure ulcer on the body part 1006. The user interface 1016 may moreover receive information including settings for monitoring the body part 1006 or characteristics associated with the body part 1006 usable to enhance monitoring or treatment of the body part 1006.

The one or more sensors 1020 can be used to monitor loading or positioning of the body part 1006, healing of the body part 1006, delivery of therapy to the body part 1006 or another part of the patient, or compliant use of an orthopedic device that assists with preventing or healing a wound like a pressure ulcer on the body part 1006 or offloading weight from the body part 1006. The one or more sensors 1020 can include one or more accelerometers, gyroscopes, magnetometers, pressure sensors, optical sensors, membrane switches, dome switches, scissor switches, capacitive switches, mechanical switches, buckling spring mechanisms, Hall effect sensors, optical switches (light eclipsed by contact of the sole of a foot with a floor, with potentially a vicinal light emitting diode being incorporated for low level lighting conditions), among other types of sensors. The one or more sensors 1020 can be positioned proximate to the body part 1006 or may be remote from the body part 1006 yet usable to monitor characteristics of the body part 1006, another part of the patient, or another device.

In certain implementations, the one or more sensors 1020 can include a pressure sensor that monitors pressure in an enclosed space or volume. The pressure sensor can, for instance, monitor pressure underneath a dressing. The dressing can be used for provision of negative pressure wound therapy for the body part 1006, and the pressure sensor can monitor pressure in a fluid flow path connecting the negative pressure source 1014 and the dressing. The pressure in the fluid flow path may be indicative of pressure in the volume enclosed by the dressing. The dressing can be used to create a sealed environment without provision of negative pressure. Any of negative pressure or non-negative pressure dressings described herein can be used.

The one or more sensors 1020 can additionally or alternatively include a pressure sensor that monitors ambient pressure or pressure external to the loading monitoring apparatus 1002 in some implementations. The pressure sensor in such embodiments can be an absolute pressure sensor. The one or more sensors 1020 can communicate data wirelessly or over one or more wires.

The transceiver 1022 can be used to communicate with the data processing system 1004, such as directly or via a network 1008. The transceiver 1022 can, for example, transmit device usage data like alarms, monitored loading or positioning, or changes to a monitoring or therapy program performed by the load monitoring apparatus 1002 to the data processing system 1004. The network 1008 can be a communication network, such as a wireless communications network like a cellular communications network. The memory device 1012 can be used to store the device usage data that may be transmitted by the transceiver 1022. The data processing system 1004 can, in some implementations, analyze load data received from the transceiver 1022 to monitor loading or positioning of the body part 1006, healing of the body part 1006, delivery of therapy to the body part 1006 or another part of the patient, or compliant use of an orthopedic device.

In some embodiments, multiple body parts can be monitored by the load monitoring apparatus 1002. In such cases, multiple sensors 1020 can be used for monitoring the body parts.

Pneumatic Pressure Load Monitoring

Figure 5:
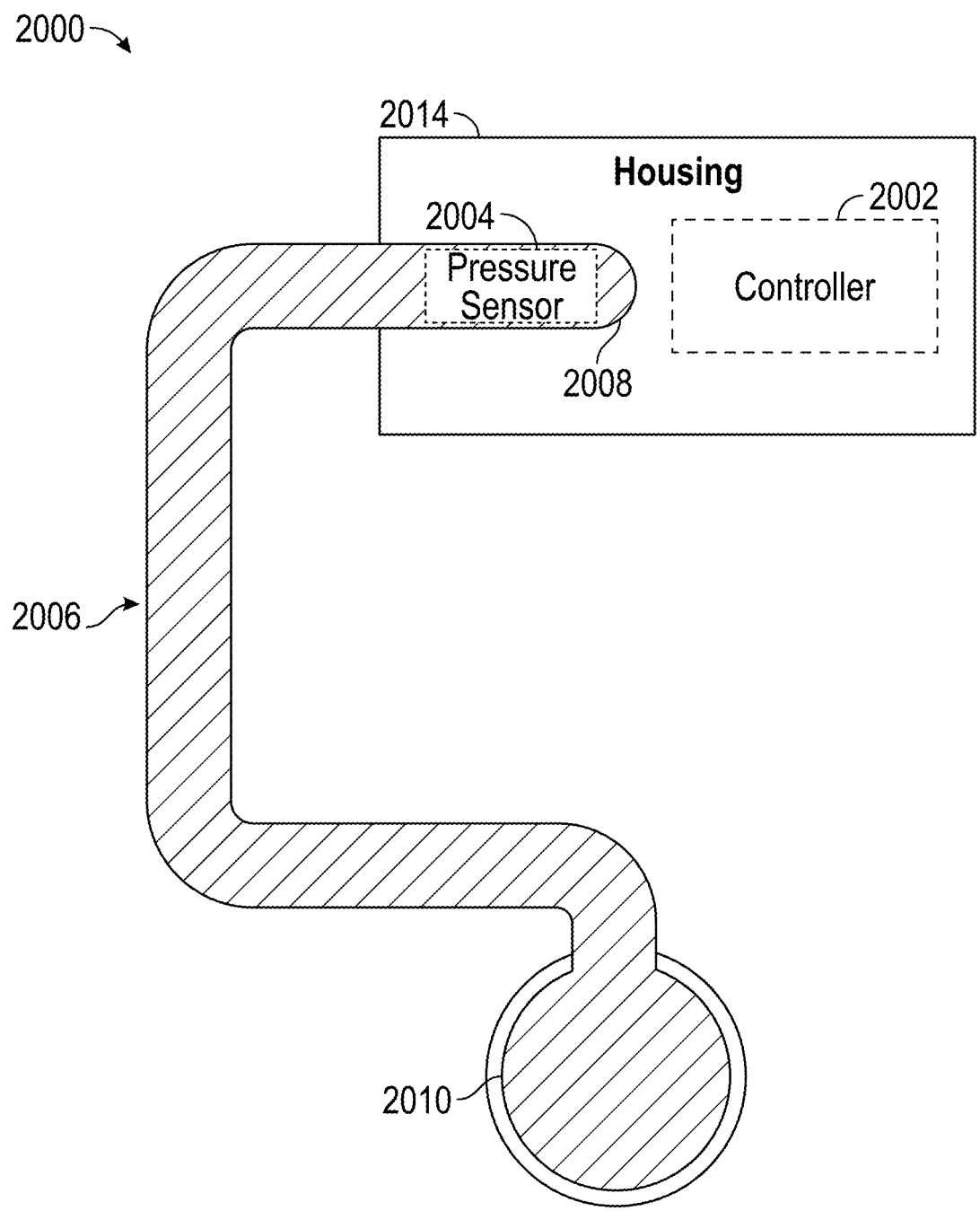
FIGS. 5, 6, 7A, and 7B illustrate load monitoring apparatuses according to some embodiments.

FIG. 5 illustrates an embodiment of a load monitoring apparatus 2000 that includes an elongate conduit 2006 having an enlarged distal end or conduit head 2010. The elongate conduit 2006 can be SOFT PORT as described herein. The load monitoring apparatus 2000 further includes a pressure sensor 2004 configured to measure a pressure within the elongate conduit 2006, as well as a controller 2002 configured to process sensor data from the pressure sensor 2004. As illustrated, the load monitoring apparatus 2000 can also include a housing 2014 that houses the controller 2002, the pressure sensor 2004, and a portion of the elongate conduit 2006. The load monitoring apparatus 2000 can be an implementation of the load monitoring apparatus 1002 of FIG. 4.

The elongate conduit 2006 can form an enclosure configured to confine and retain a gas or liquid. For example, the elongate conduit 2006 can serve as a reservoir for confining gas or liquid within an internal volume. For example, the elongate conduit 2006 can be at least partially filled with liquid or at least partially filled with gas (such as air). The elongate conduit 2006 can be liquid or gas impermeable such that the elongate conduit 2006 seals the internal volume from an external environment and retains the liquid or gas within the internal volume. The elongate conduit 2006 can take many forms, including, but not limited to a combination of one or more of a bladder, a pneumatic chamber, a length of tubing, or other air- or liquid-tight apparatus.

In some cases, the elongate conduit 2006 can include a flat tube or includes one or more layers that can form the internal volume. The one or more layers can include one or more sheets or multiple flat surfaces. For example, the elongate conduit 2006 can include a top or cover layer and a backing layer. These two layers can be joined or sealed together so as to define an interior space or chamber. This interior space or chamber may include additional structures that may be further adapted store fluids. For example, the top layer and backing layer can be liquid or gas impermeable. This impermeability can extend across the entirety of the elongate conduit 2006 to allow the elongate conduit 2006 to store fluids without any leaks. In another example, the top layer or backing layer can be gas permeable.

At least a portion of the elongate conduit 2006 can be collapsible, flexible, bendable, pliable, or the like, such that at least a portion can be compressed. For example, the elongate conduit 2006 can include an enlarged distal end or conduit head 2008 that is configured to attach to an individual, such as the bottom of an individual's foot or a position on an individual's back. In some cases, the enlarged distal and has a round or circular shape. When the head is loaded with a threshold amount of weight (for example, the individual stands), the conduit head 2008 can compress, thereby increasing a pressure within the internal volume.

In contrast, at least a portion of the elongate conduit 2006 can include a reinforcement element configured to prevent collapse (for example, compression). For example, to obtain accurate measurements, it can be desirable to prevent the central portion of the elongate conduit 2006 from compressing. That is because that system assumes that added pressure into the internal volume comes as a result of compression of the conduit head 2008. If the central portion of the elongate conduit 2006 were compressed (for example, by clothing, a bed, etc.), the system may erroneously determine that the conduit head was compressed, and thus, the individual may be moving as desired. Accordingly, in some cases, the portions of the elongate conduit 2006 other than the conduit head can be reinforced to prevent erroneous pressure readings. Moreover, at least a portion of the elongate conduit 2006 can include a reinforcement element configured to cause that portion to return to a pre-load state or shape after removal of loading.

In some embodiments, the elongate conduit 2006 is pressurized or depressurized. For example, when unloaded (for example, not compressed), the internal volume of the elongate conduit 2006 can be pressurized to be greater than atmospheric pressure (for example, about 101,795 Pa). In other embodiments, when unloaded, the internal volume of the elongate conduit 2006 can be approximately at atmospheric pressure. Accordingly, when loaded, the pressure of the internal volume can increase above atmospheric pressure. Still, in other embodiments, when unloaded, the internal volume of the elongate conduit 2006 can be depressurized to be less than atmospheric pressure (for example, 50,000 Pa). Accordingly, when loaded, the pressure of the internal volume can increase (for example, to another pressure below atmospheric pressure, to approximately atmospheric pressure, or above atmospheric pressure).

The pressure sensor 2004 can be configured to measure the pressure within the internal volume of the elongate conduit 2006. For example, the pressure sensor can measure the pressure at one or more locations along the elongate conduit 2006, such as near the conduit head 2010, near a central portion of the elongate conduit 2006, or at the conduit head 2008 at an opposite end of the elongate conduit 2006 from the conduit head 2010.

The controller 2002 can process sensor data from the pressure sensor 2004 to determine information regarding movement of the individual. For example, as described in more detail herein, the controller 2002 can receive pressure data over a period of time. Based at least in part on a change (or no change or degree of change) in the pressure over the period of time, the controller 2002 can determine whether the conduit head 2010 of the elongate conduit 2006 has been loaded within the period of time. From this, the controller 2002 can determine an activity classification for movement of an individual. For example, if the conduit head 2010 is positioned on the individual foot, changes in pressure over time may indicate that the individual was standing, walking, running, or otherwise moving his foot to apply a threshold amount of weight. In some cases, based on the pressure data, the controller 2002 can output for presentation an indication denoting movement (or lack thereof) of the foot.

In some embodiments, rather than comprising an air- or liquid-tight enclosure, the elongate conduit 2006 may provide for a gas (or liquid) leak, such as a relatively low pressure leak. This may be referred to as a "leaky" elongate conduit. Accordingly, in contrast to the pressurized or depressurized "sealed" elongate conduit, when the elongate conduit is unloaded (for example, for a threshold period of time), the pressure of the internal volume may normalize to atmospheric pressure. When loaded, the pressure of the internal volume can initially increase above atmospheric pressure. However, because of the leak, even if loading is maintained, the pressure of the internal volume will slowly return to atmospheric pressure (for example, as the fluid leaks out of the enclosure). Furthermore, when the load is removed, the pressure of the internal volume is reduced to a pressure below atmospheric pressure. However, because of the leak, even if unloading is maintained, the pressure of the internal volume will slowly return to atmospheric pressure (for example, as the fluid leaks in to the enclosure). The "leaky" elongate conduit may be desirable, in some instances, because the leak may prevent the elongate conduit from inflating when the elongate conduit moves from one altitude to a higher altitude. The "leaky" elongate conduit however may, in some instances, create a system that is less sensitive or less able to detect static loads than the elongate conduit without a leak.

Figure 6:
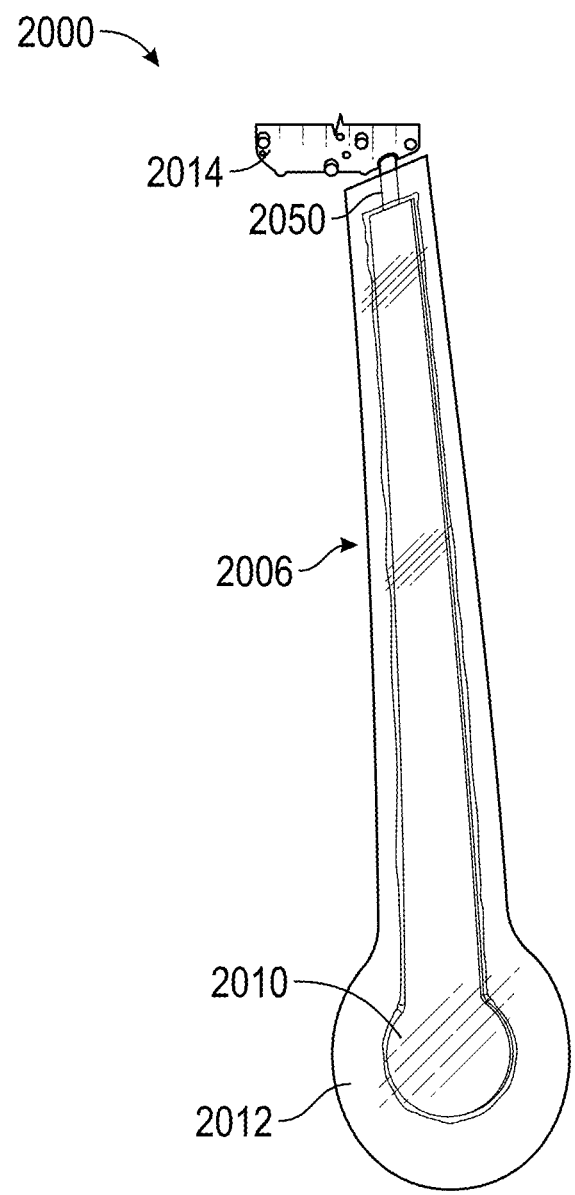

FIG. 6 illustrates an example implementation of the load monitoring apparatus 2000 that includes the elongate conduit 2006 attached to the housing 2014. The elongate conduit 2006 includes an enlarged distal end or conduit head 2008, and further includes an adhesive layer 2012.

As illustrated in FIG. 6, at least some portions of the elongate conduit 2006 can include a lower or upper adhesive layer 2012 that may be helpful to adhere the elongate conduit 2006 to the skin or clothing of the individual. For example, a lower adhesive layer may be provided on the lower surface of the elongate conduit 2006 or an upper adhesive layer 2012 may be provided on the upper surface of the elongate conduit 2006. As illustrated, the adhesive layer 2012 may define a larger perimeter than that of the other layers of the elongate conduit 2006, such that the adhesive layer 2012 extends over an edge of the other layers to adhere to the individual's skin of clothing. The adhesive may be a silicone, hot melt, hydrocolloid or acrylic based adhesive or other such adhesives and may be formed on both sides or optionally on a selected one or none of the sides of the elongate conduit 2006. Furthermore, the adhesive may be an adhesive coating.

In some cases, the elongate conduit 2006 can include an adhesive on some but not all portions of the elongate conduit 2006. For example, the enlarged distal and or conduit head 2008 may include an adhesive layer, but the central and proximal portions of the elongate conduit 2006 may not include an adhesive layer. This may advantageously allow a user to position the conduit head 2008 in the appropriate location (for example, attach the conduit head 2008 to the user's foot), while also maintaining flexibility as to the location of the central portion of the elongate conduit 2006.

As illustrated in FIG. 6, at least a portion of the elongate conduit 2006 can include a tubing 2050. For example, the tubing 2050 may be coupled to the housing 2014 and may also be coupled to a fluidic connector that is coupled to the conduit head 2010. In some configurations, the tubing can have a diameter between 10 mm and 100 mm. The tubing 2050 may help maintain the integrity of the elongate conduit 2006 while also helping to create fluid tight seal of the internal volume. In addition to its added integrity, the tubing can be substantially flexible so as to not be rigid when worn by an individual. The tubing or other portion of the elongate conduit 2006 disclosed herein can be formed from polyurethane, PVC, nylon, polyethylene, silicone, or any other suitable material.

Figure 7A:
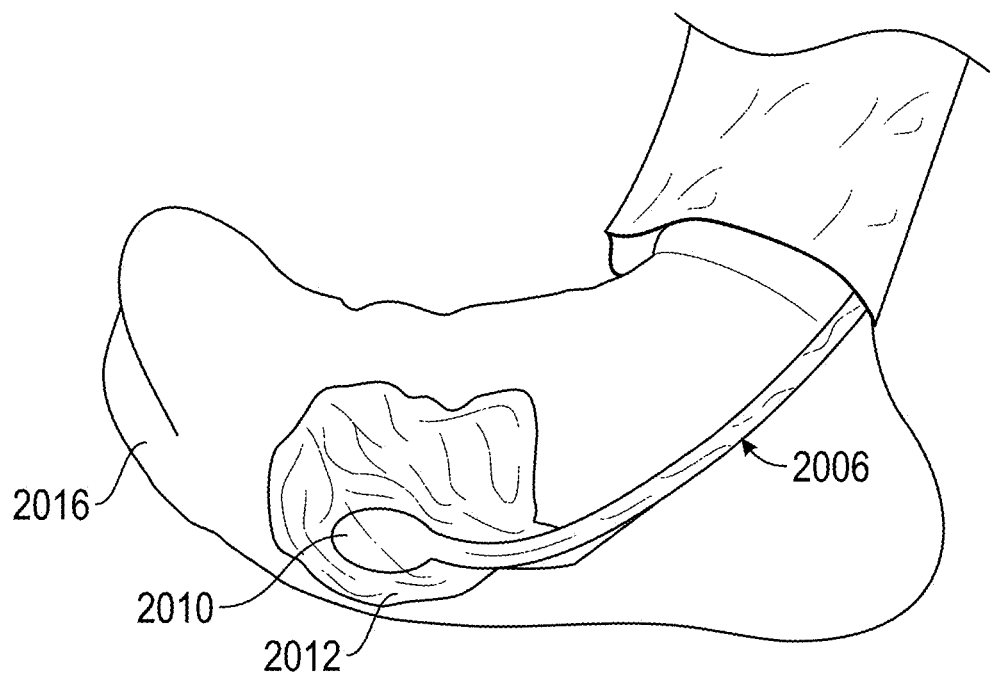
Figure 7B:
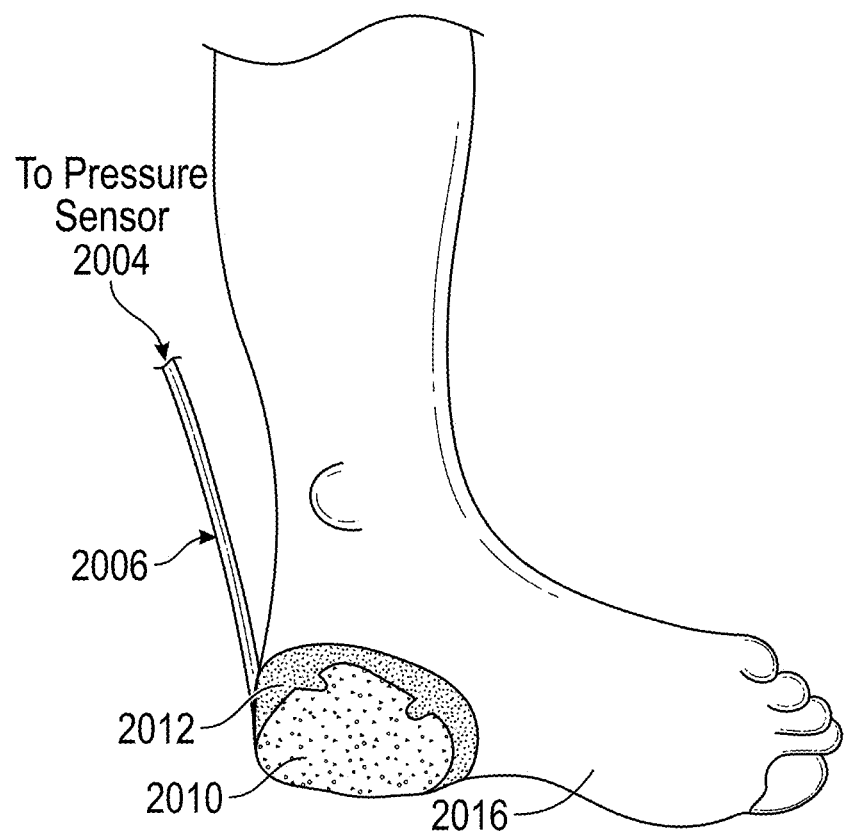

FIGS. 7A and 7B illustrate example implementations of the load monitoring apparatus 2000. For example, FIG. 7A illustrates an example of the load monitoring apparatus 2000 in which a conduit head 2010 of an elongate conduit 2006 is attached to a ball of an individual's foot 2016, while FIG. 7B illustrates an example of the load monitoring apparatus 2000 in which a conduit head 2010 of an elongate conduit 2006 is attached to a heel of the individual's foot 2016.

The load monitoring apparatus 2000 can monitor, track, or report movement by the individual. For example, because (in both FIGS. 7A and 7B) the conduit head 2010 is positioned on the bottom of the individual's foot, the pressure of the elongate conduit 2006 will change when the individual loads his or her foot, such as by standing or walking. That is because when the individual stands, the conduit head 2010 will be positioned between the individual's foot and the walking surface and will be compressed by the individual's weight. Accordingly, by monitoring pressure changes in the elongate conduit 2006, the load monitoring apparatus can determine that an individual is moving, and, in some cases, can determine how an individual is moving (for example, laying, standing, walking, running, etc.).

Although FIGS. 7A and 7B illustrate the conduit head 2010 attached to the individual's foot, the conduit head 2010 can be attached to one or more other locations on the individual's body to determine other movement characteristics. For example, a conduit head 2010 can be attached to the individual's back (for example, to determine if the individual is lying down), to the shoulder, hip, or side (for example, to determine if the individual is resting on his side), to the torso or abdomen (for example, to determine if the individual is lying on his stomach), or the like.

Figure 8:
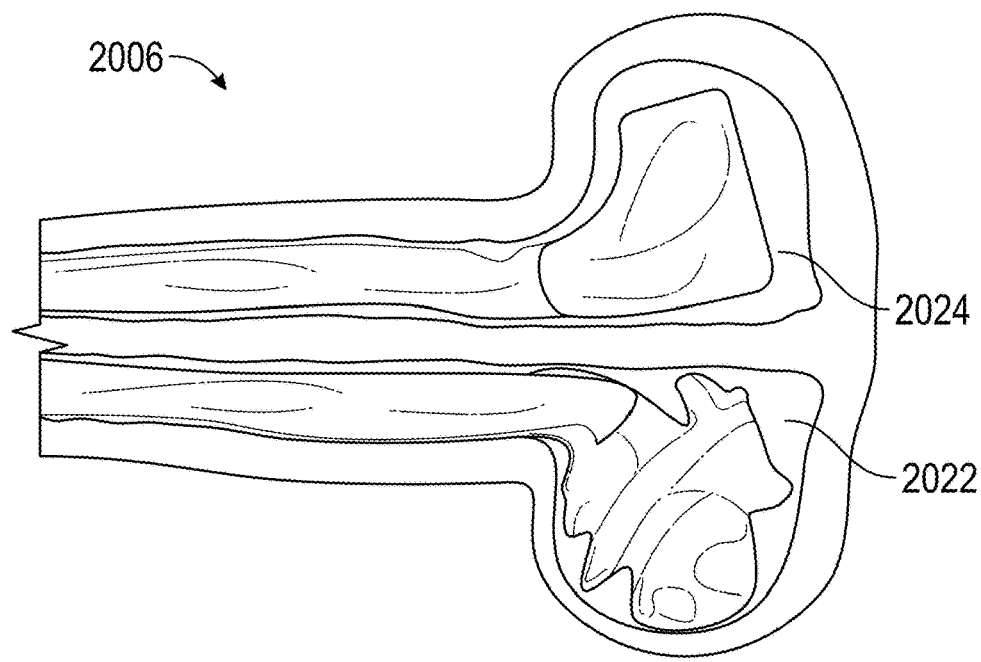
FIG. 8 illustrates an elongate conduit that includes multiple channels according to some embodiments.

FIG. 8 illustrates an embodiment of the elongate conduit 2006 that includes multiple channels, each channel having a channel head (or conduit head). Further, each of the channels can include padding (for example, foam), which may provide increased comfort to an individual when the individual loads a channel.

As illustrated, the elongate conduit 2006 includes two parallel pneumatic pathways (for example, channels 2022, 2024) that each correspond to the elongate conduit 2006 described above with respect to FIG. 5. Accordingly, each channel 2022, 2024 can form a sealed or leaky enclosure configured to confine a gas or liquid, thereby serving as a reservoir for confining gas or liquid within an internal volume. Furthermore, each channel 2022, 2024 can include an enlarged distal head, as described herein.

In various embodiments, the multiple channels 2022, 2024 can be attached to different portions of the individual's body. For example, the first channel 2022 can be mounted to a first part of the foot (such as the ball of the foot) and the second channel head can be mounted to a second part of the foot different from the first part (such as the heel). Furthermore, one or more pressure sensors can measure the pressure in the first channel 2022 separately from the pressure in the second channel 2024.

In some cases, based on the pressure data corresponding one or more of the channels 2022, 2024, the controller 2002 can determine various movement characteristics of the individual. For example, if the channels 2022, 2024 are positioned on different parts of the individual's foot, based on the pressure data, the data processing circuitry can determine or predict the individual's weight distribution. For example, if the channel corresponding to the ball of the individual's foot has a higher pressure or pressure change than the channel corresponding to the heel of the individual's foot, then the controller 2002 can determine that the user's weight distributed unevenly, or can determine that user's weight is distributed more on the individual's toes that his heels. In addition or alternatively, using the pressure data from various channels, the controller 2002 can determine a more accurate prediction of movement (for example, walking, running, standing, etc.).

Figure 9A:
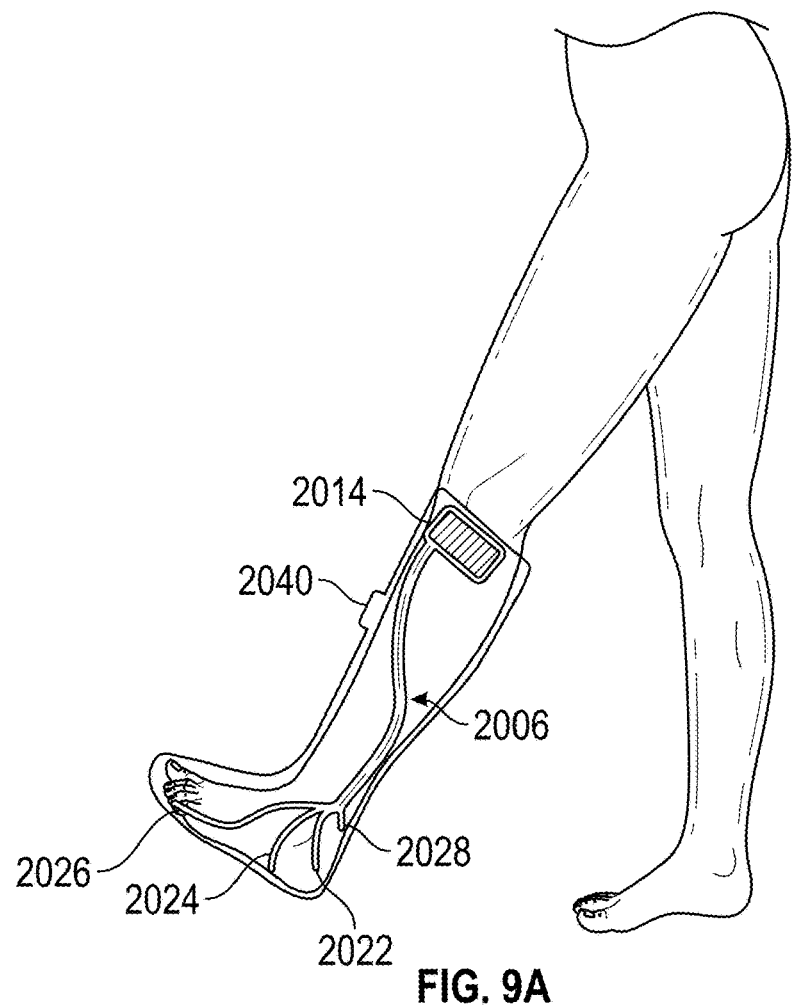
FIGS. 9A and 9B illustrate an elongate conduit that includes multiple channels positioned at different locations on an individual's foot according to some embodiments.
Figure 9B:
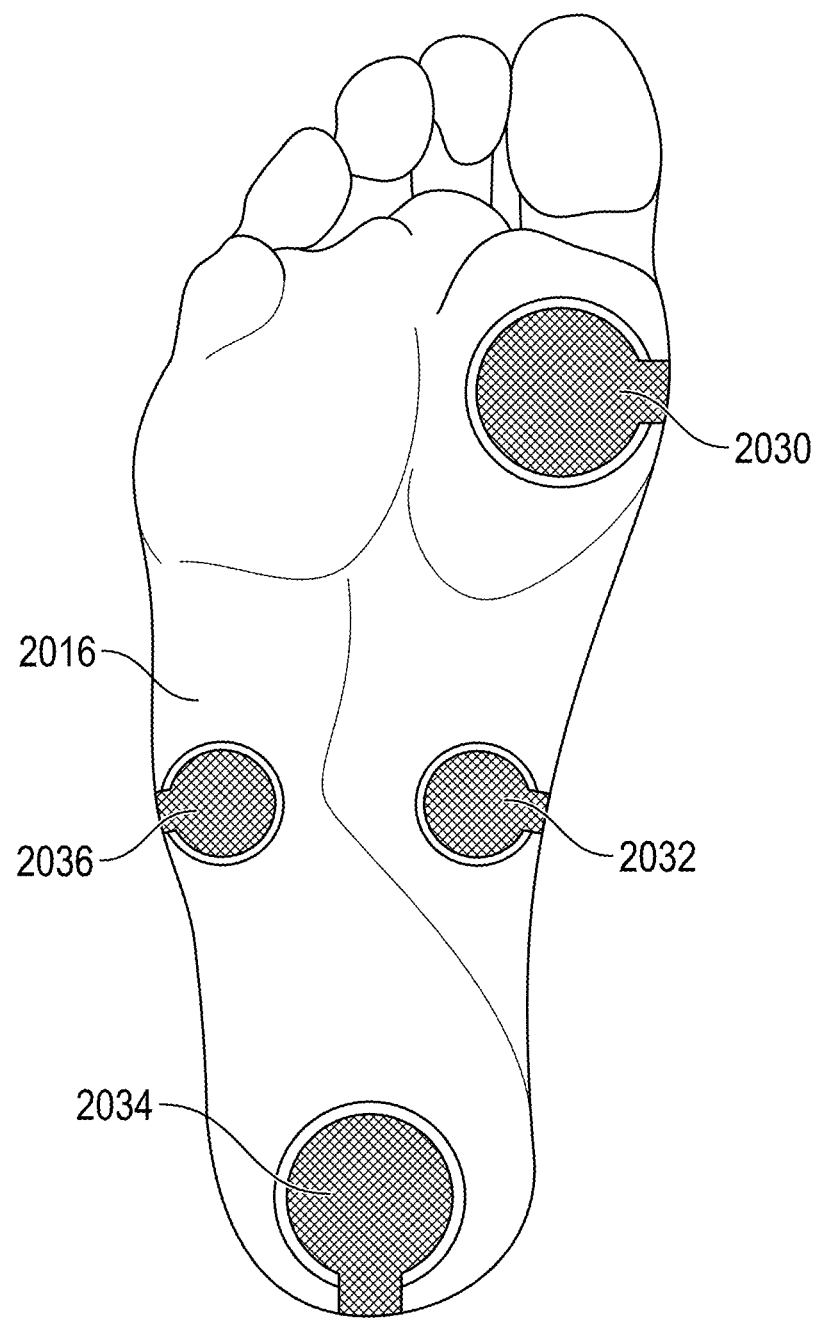

FIGS. 9A and 9B illustrate an embodiment of the elongate conduit 2006 that includes multiple channels positioned at different locations on an individual's foot. Furthermore, FIG. 9B illustrates an embodiment of a load monitoring apparatus that incorporates different sized channel heads (for example, two larger channels heads 2030, 2034 and two smaller channel heads 2032, 2036).

As illustrated in FIGS. 9A and 9B, the elongate conduit 2006 comprises four channels 2022, 2024, 2026, 2028, each channel having a channel head (for example, channel heads 2030, 2032, 2034, 2036), and each channel forming a sealed or leaky enclosure configured to confine a gas or liquid. As described above, the multiple channels 2022, 2024, 2026, 2028 can be attached to different portions of the individual's body. For example, as illustrated, a first channel head 2032 and a second channel head 2036 can be mounted to opposite sides of the middle of the foot, a third channel head 2030 can be mounted to a ball of the foot, and a fourth channel head 2034 can be mounted to a heel of the foot.

As described above, based on the pressure data corresponding one or more of the channels 2022, 2024, 2026, 2028, the controller 2002 can determine various movement characteristics of the individual. For example, the controller 2002 can determine or predict the individual's weight distribution. For example, if the channel corresponding to the ball of the individual's foot has a higher pressure or pressure change than the channel corresponding to the heel of the individual's foot, then the controller 2002 can determine that the user's weight distributed unevenly, or can determine that user's weight is distributed more on the individual's toes that his heels. Similarly, if the channel corresponding to the left side of the individual's foot has a higher pressure or pressure change than the channel corresponding to the right side of the individual's foot, then the controller 2002 can determine that the user's weight distributed unevenly, or can determine that user's weight is distributed more on the individual's left side than right side or front side than back side. In addition or alternatively, using the pressure data from various channels, the controller 2002 can determine a more accurate prediction of movement (for example, walking, running, standing, etc.).

As illustrated in FIG. 9B, in addition to having multiple channels, one or more of the channels or channel heads can be sized differently (for example, have a different diameter) from other channels or channel heads. Because larger channel heads have a greater internal volume (due to their larger size) than smaller channel heads, loading of larger channel heads will result in larger pressure changes than loading of smaller channel heads.

The housing 2014 configured to support the pressure sensor(s) and a controller. The housing 2014 can be sized to conveniently fit on an individual's body, such as at or around the knee or hip region. In addition or alternatively, the housing 2014 can be attached to an external support, such as a cast 2040 worn by the individual. Further, the elongate conduit 2006 can extend around or along a leg of the individual.

Figure 10:
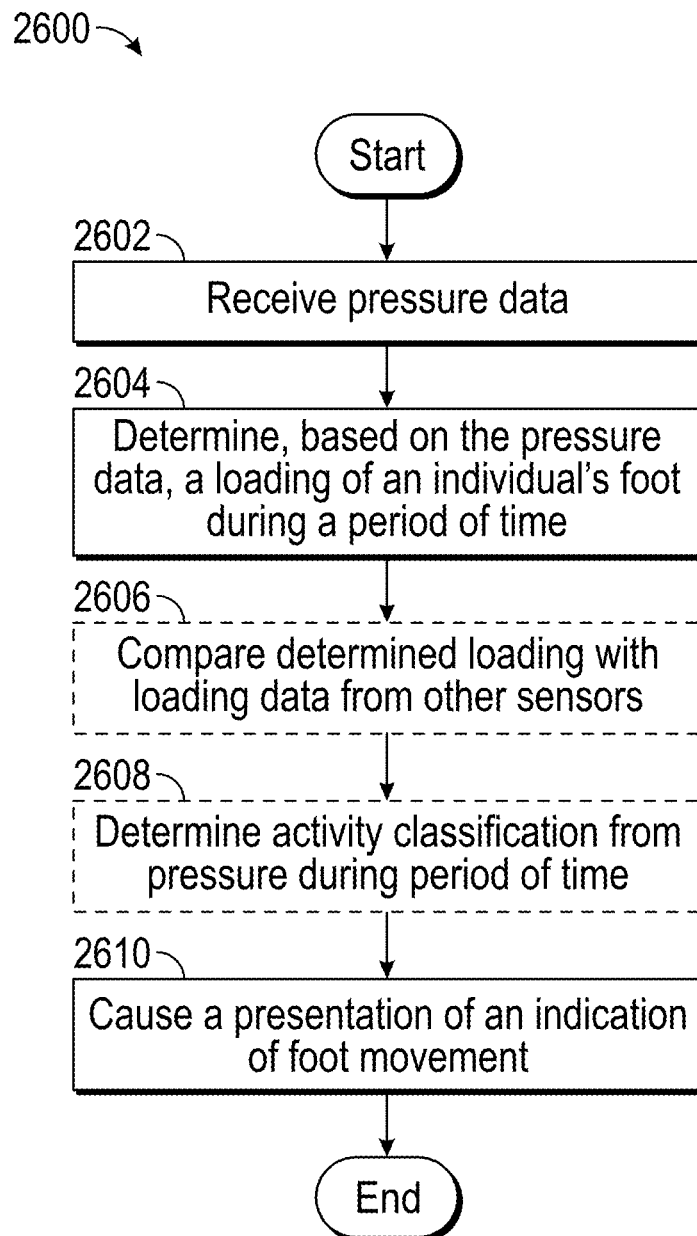
FIG. 10 illustrates a process for monitoring load bearing using a load monitoring apparatus according to some embodiments.

FIG. 10 illustrates a process 2600 for monitoring load bearing performable by a device, such as the load monitoring apparatus 2000 of FIG. 5. In some embodiments, the process 2600 can be implemented by a controller, such as the controller 2002 of FIG. 5. For convenience, the process 2600 is described in the context of the load monitoring apparatus 2000, but may instead be implemented in other systems described herein, or by other computing systems not shown. The process 2600 can advantageously, in certain embodiments, enable the load monitoring apparatus 2000 to monitoring load bearing of an individual over a period of time and output an indication of the load bearing for presentation to the individual or other.

At block 2602, the process 2600 can receive pressure data indicative of a magnitude or frequency of pressure measured within an internal volume of an elongate conduit of the load monitoring apparatus. For example, the process 2600 can receive pressure data indicative of an amplitude, magnitude, frequency, or cumulative sum value of one or more pressure pulses. The elongate conduit, such as an enlarged distal end of the elongate conduit, can be attached to the individual, such as to the bottom of the individual's foot (for example, on the ball, heel, or side of the foot). The pressure can be measured, for instance, by the pressure sensor 2004. The pressure sensor 2004 can communicate information via a wire or wirelessly to the controller 2002. In certain implementations, the pressure sensor 2004 can be positioned at or near an end of the elongate conduit that is opposite the enlarged distal end. In some embodiments, pressure sensor data includes one or more magnitudes of pressure measured over a duration of time, such as 0.1 seconds, 0.5 seconds, 1 second, 3 seconds, or the like.

At block 2604, the process 2600 can determine a loading of the individual's foot from pressure during a period of time using the pressure data. The process 2600 can, for instance, analyze a change in a magnitude of the pressure over time during the time period (such as during the time period of at least 1 second, 2 seconds, 5 seconds, 10 seconds, 30 seconds, or 1 minute).

At block 2606, the process can compare the loading data determined at block 2604 with loading data from other sensors. The load monitoring apparatus can include various other sensors in addition to the pressure sensor to confirm the loading data determined from the pressure data. For example, the load monitoring apparatus can include one or more of a gyroscope or accelerometer to measure orientation or angular velocity of the individual's foot or leg over time. Based on this orientation or velocity data over time, the process 2600 can determine if the individual's leg was moving, which can indicate that the leg was loaded. The process 2600 can compare the results of the loading determining using the pressure sensor with the loading determination using the gyroscope or accelerometer to confirm that the determined load monitoring is accurate.

At block 2608, the process 2600 can further determine an activity classification based on the pressure data. For example, based on the determined loading of the individual's foot, the process 2600 can determine that, over the prior of time, the individual was performing one or more of sitting, laying, walking, standing, of running.

At block 2610, the process 2600 can cause a presentation of an indication of foot movement. The indication can be output, for example, by one or more of: outputting the indication for presentation to a user via a user interface, or storing the indication in association with device usage data of the load monitoring apparatus. In some examples, the outputting of the indication can allow a user to detect when the individual is mobile.

Figure 11:
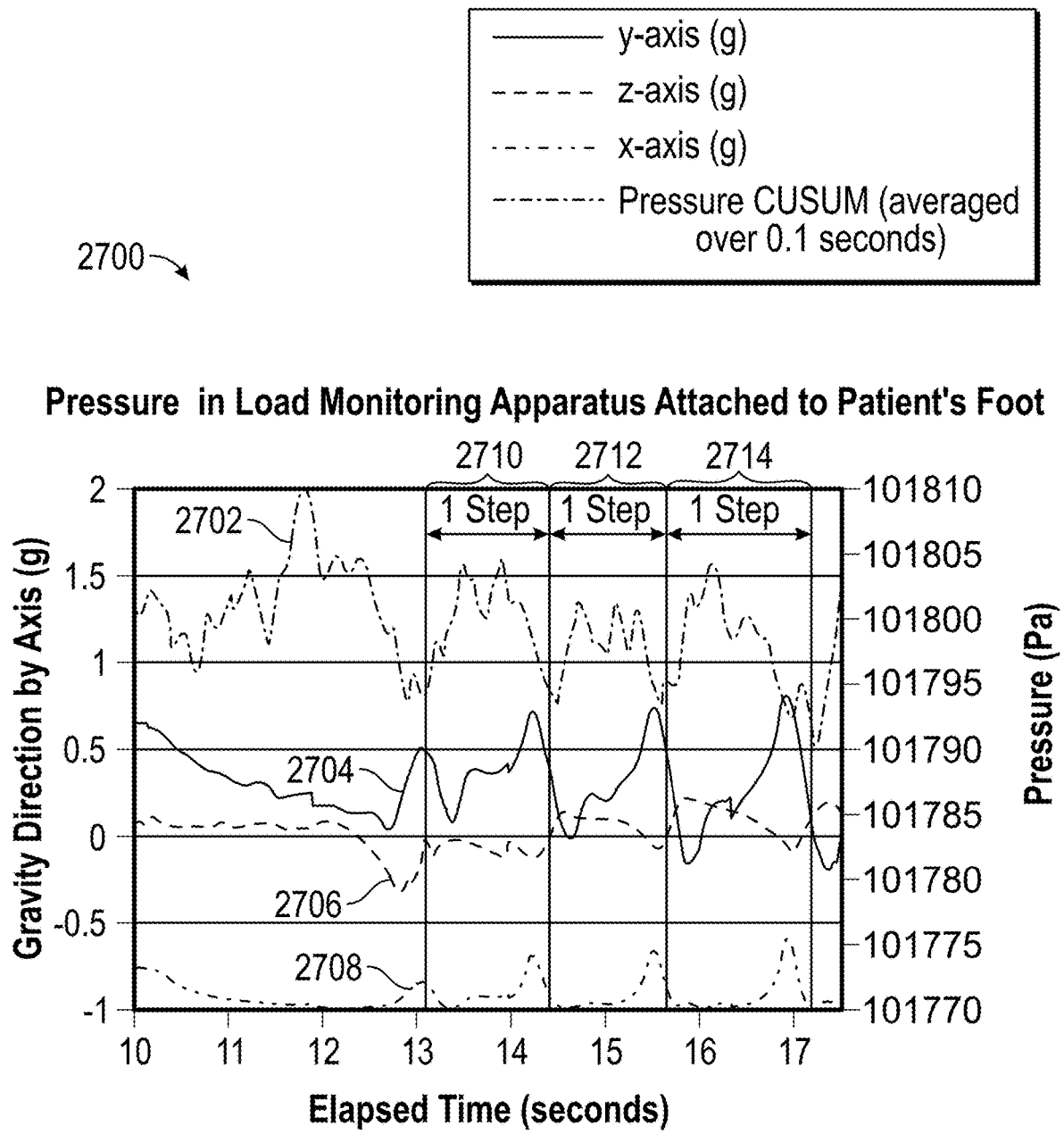
FIG. 11 is a plot of pressure variations over time in a load monitoring apparatus as well as various directions of gravity over time according to some embodiments.

FIG. 11 provides a plot 2700 which illustrates pressure variations over time in a load monitoring apparatus, as well as various directions of gravity (for example, of an x-, y-, and z-axis) over time. In this example, the enlarged head of an elongate conduit (as such elongate conduit 2006 of FIG. 5) was attached to an individual's foot, as was an accelerometer. Because the changes in pressure of data line 2702 corresponds to the changes in direction of gravity of data lines 2704, 2706, and 2708, plot 2700 confirms that pressure changes within the internal volume of a elongate conduit (as such elongate conduit 2006 of FIG. 5) corresponds to certain movement of the individuals foot.

Boxes 2710, 2712, and 2714 each represents a step (from off-ground, through strike, to off-ground again) of the individual as the individual walks. In this example, data line 2704 corresponds to gravity in the y-axis (fore-aft) direction, data line 2706 corresponds to gravity in the z-axis direction (lateral movement), and data line 2708 corresponds to gravity in the x-axis direction (for example, a value of −1 indicates that the leg is vertically downward). Based on each of these data lines 2704, 2706, 2708, it can be seen that the boxes 2710, 2712, and 2714 do in fact each represent a step (from off-ground, through strike, to off-ground again) of the individual as the individual walks.

Data line 2702 illustrates pressure variations over time in a load monitoring apparatus as the individual walks. As can be seen, pressure increases indicate that the foot is being loaded (for example, it is on the walking surface). This is confirmed by data lines 2704, 2706, 2708. Accordingly, pressure changes within the internal volume of an elongate conduit correspond to certain movement of the individual's foot.

For example, in response to the magnitude of pressure rising above a baseline pressure (in this example, about 101,795 Pa), a controller, such as the controller 2002, can determine that the individual is loading the conduit head 2010.

Based at least in part on a length of time that the magnitude pressure remains above the baseline pressure, the processor can determine one or more activity classifications for the individual. For example, in response to the magnitude of pressure rising above the baseline pressure a period of time (for example, 2, 3, 5, 7, 10, or more seconds), the controller can determine that the individual standing. That is because the constant loading of the load monitoring device implies that the individual is loading his foot by standing. Similar determinations can be made for other activity classifications such as running, which the magnitude of pressure will mimic the repetition of walking (as described above), but the frequency may be faster.

Similarly, the controller can determine that individual is not standing (or not loading his foot) if the magnitude of pressure remains around the baseline pressure, or varies a relatively minimal amount over time.

Furthermore, in some embodiments, frequency of the pressure signal can be used for determination of an activity classification. For example, as is shown in FIG. 11, the pressure cycle (for example, the rise of the magnitude of pressure above the baseline pressure and the drop of the magnitude of pressure to about the baseline pressure) has a particular frequency (for example, about 1-2 seconds) as the individual walks. That is because repeated loading and unloading of the load monitoring device (which, in this example is attached to the bottom of the individual's foot) is indicative of someone transferring his or her weight from one foot to the next, which correlates with walking. The frequency will increase as the individual walks faster or begins running, and the frequency will decrease as the individual walks more slowly. Accordingly, based on the frequency of the individual loading and then unloading the conduit head of the elongate conduit, the processor can determine if the individual is walking slowly, walking at a normal pace, or running.

Figure 12:
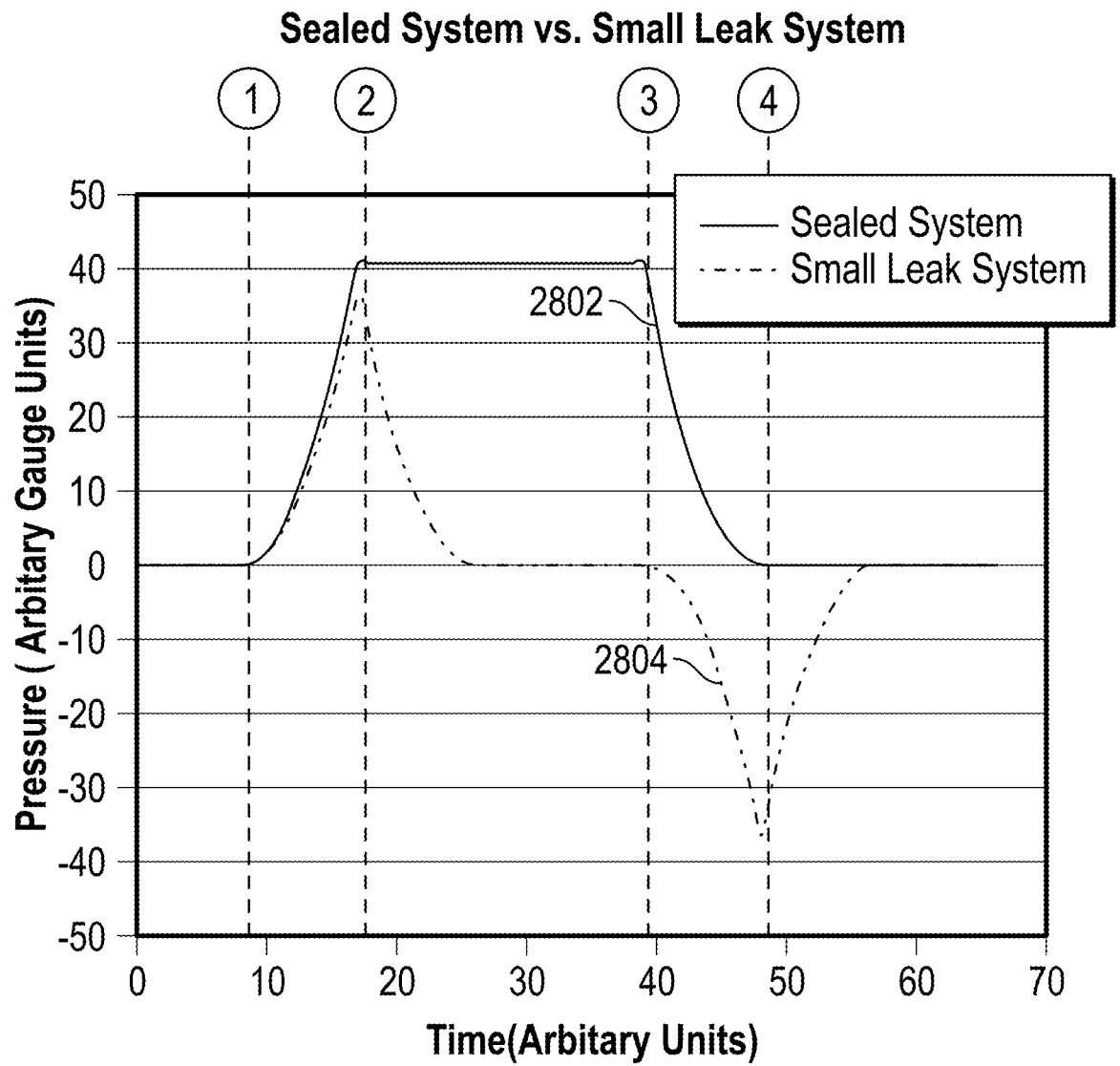
FIG. 12 is a plot of magnitude of pressure in a sealed system versus a leaky system as load is applied and removed according to some embodiments.

FIG. 12 illustrates a plot 2800 of magnitude of pressure in a sealed system (line 2802) versus a leaky system (line 2804) as load is applied and removed. For both the sealed and the leaky system, prior to position (1), the conduit head is not loaded. For example, individual may be laying down, sitting down, or otherwise situated such that the bottom of the individual's foot, and therefore the conduit head, is unloaded. At position (1), the individual applies load to the conduit head. This may include, for example, the individual standing up such that the individual is placing weight upon the foot to which the conduit head is attached. Between positions (2) and (3), the individual continues to apply a static load to the conduit head. For example, the individual could be continuing to stand. At position (3), the individual begins to remove the load. For example the individual can begin to lift his or her foot off the ground, thereby beginning to unload the conduit head. At position (4), the conduit head is completely unloaded. For example, the individual may be laying back down.

As illustrated, the magnitudes of pressure behave different in the sealed system than they do in the leaky system. In the sealed system, prior to position (1), the internal volume of the elongate conduit has an arbitrary pressure of 0. At position (1), as the individual applies load to the conduit head, the pressure begins to increase until it reaches position (2), where the pressure remains constant until position (3). The pressure remains constant because the individual is applying a constant load to the conduit head and the fluid (for example, gas to liquid) is not escaping from the elongate conduit. At position (3), the individual begins to remove the load and the pressure begins to decrease. At position (4), the conduit head is completely unloaded and the pressure immediately returns to the arbitrary pressure of 0.

In contrast to the sealed system, the leaky system may not maintain any pressure other than the arbitrary pressure of 0 (which can be atmospheric pressure). For example, in the leaky system, prior to position (1), the internal volume of the elongate conduit has an arbitrary pressure of 0. At position (1), as the individual applies load to the conduit head, the pressure begins to increase until it reaches position (2). (It should be noted that although, like the sealed system, the leaky system reaches its maximum pressure at position (2), the pressure in the leaky system does reach the max of the closed system because of the pressure leak in the leaky system while the load is being applied.) As position (2), the individual is applying a constant load. However, gas or liquid is leaking out of the elongate conduit and the pressure begins decreases. At position (3), the individual unloads the elongate conduit. However, because the enclosed area has a lower pressure than the area around it, the pressure in the enclosed volume continues to become more negative. At position (4), the conduit head is completely unloaded and the pressure begins to return to the arbitrary pressure of 0.

Figure 13:
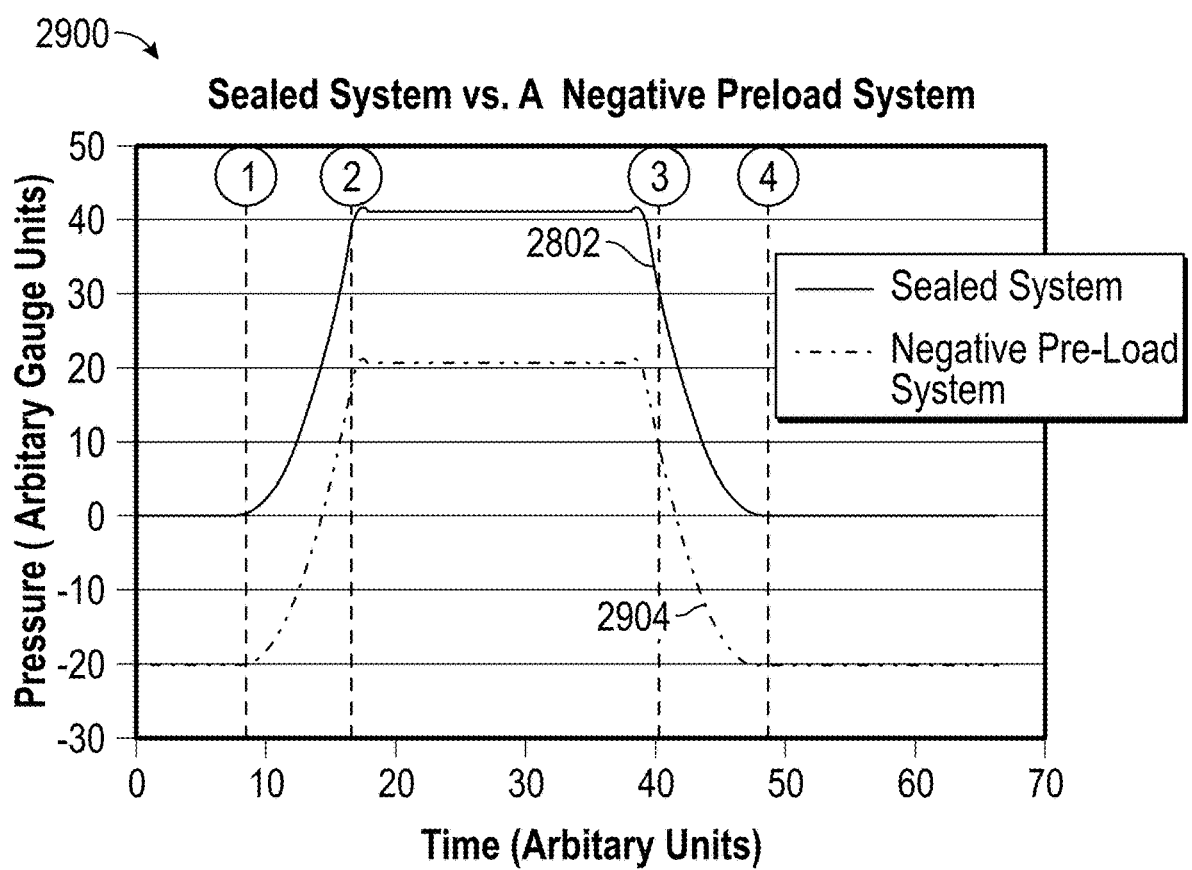
FIG. 13 is a plot of magnitude of pressure in a sealed system versus a sealed negative pre-load system as load is applied and removed.

FIG. 13 illustrates a plot 2900 of magnitude of pressure in a sealed system (line 2802) versus a sealed negative pre-load system (line 2904) as load is applied and removed. For this example, the individual performed the same series of events (for example, position (1) to position (4)) described above with respect to FIG. 12. However, in addition to the magnitude of pressure in the sealed system (line 2802), the plot 2900 also includes data indicative of magnitude of pressure in a sealed negative pre-load system as the load is applied and removed. Negative pre-load indicates that the pressure in the elongate conduit was reduced before it was sealed. As shown, the magnitude of pressure in the sealed negative pre-load system (line 2904) correlates directly with the magnitude of pressure in the sealed system (line 2802).

In some cases, pressure sensors are limited in the range of pressures that they can measure. For example, utilizing a 300 mbar to 1100 mbar abs sensor at atmospheric pressure could limit the ability to measure pressure because the system could only be used for 1000 mbar abs to 1100 mbar. However, by depressurizing the internal volume before it is sealed, the system can utilize an effective portion of the pressure sensor range (for example, by depressurizing the volume to 500 mbar abs prior to sealing).

Motion Detection Load Monitoring

Figure 14:
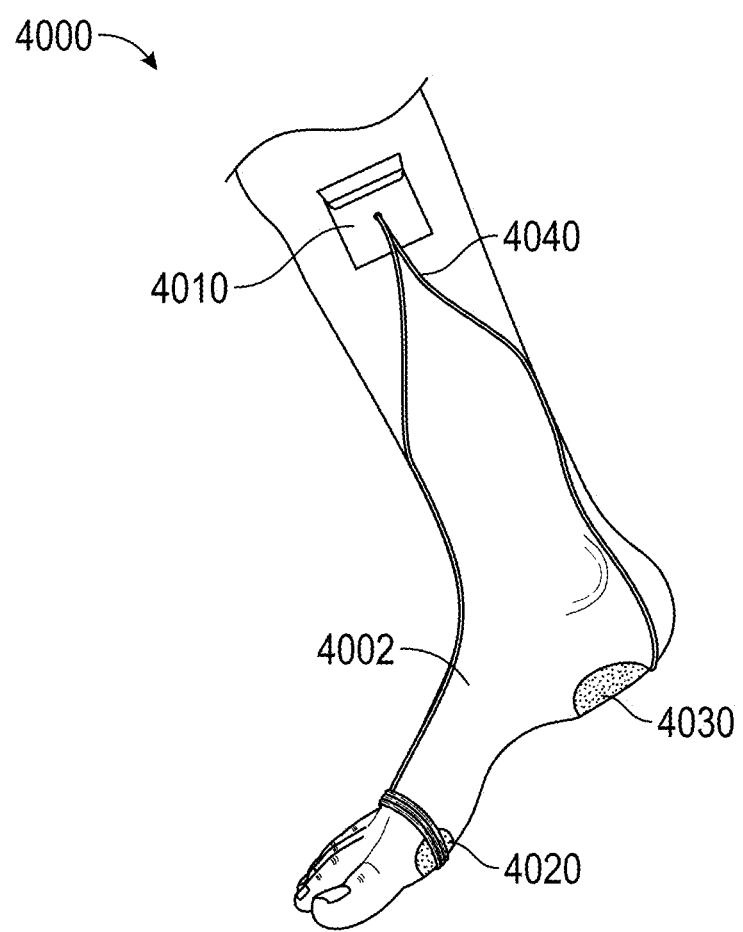
FIG. 14 illustrates a monitoring system that includes a load monitoring apparatus attached to a leg of an individual according to some embodiments.

FIG. 14 illustrates a monitoring system 4000 that includes a load monitoring apparatus 4010 attached to a leg 4002 of an individual. The load monitoring apparatus 4010 can include an accelerometer usable to monitor a motion or position of the leg 4002 and determine one or more activities in which the leg 4002 may be engaged. The load monitoring apparatus 4010 can include a housing that supports one or more components of the load monitoring apparatus 4010 and can be attached and positioned below the individual's knee, such as beneath and proximate to the knee. The load monitoring apparatus 4010 can be an implementation of the load monitoring apparatus 1002 of FIG. 4.

The load monitoring apparatus 4010 can communicate with pressure sensors 4020, 4030 via wires 4040 to obtain pressure data usable to determine one or more activities in which the leg 4002 is engaged. The pressure sensors 4020, 4030, can, for example, attach to a bottom of a foot of the leg 4002, such as to a ball or heel, for detecting loading of the foot. In some embodiments, the load monitoring apparatus 4010, the pressure sensors 4020, 4030, or the wires 4040 can be part of or supported by a textile foot cover that may be worn on the leg 4002.

Figure 15A:
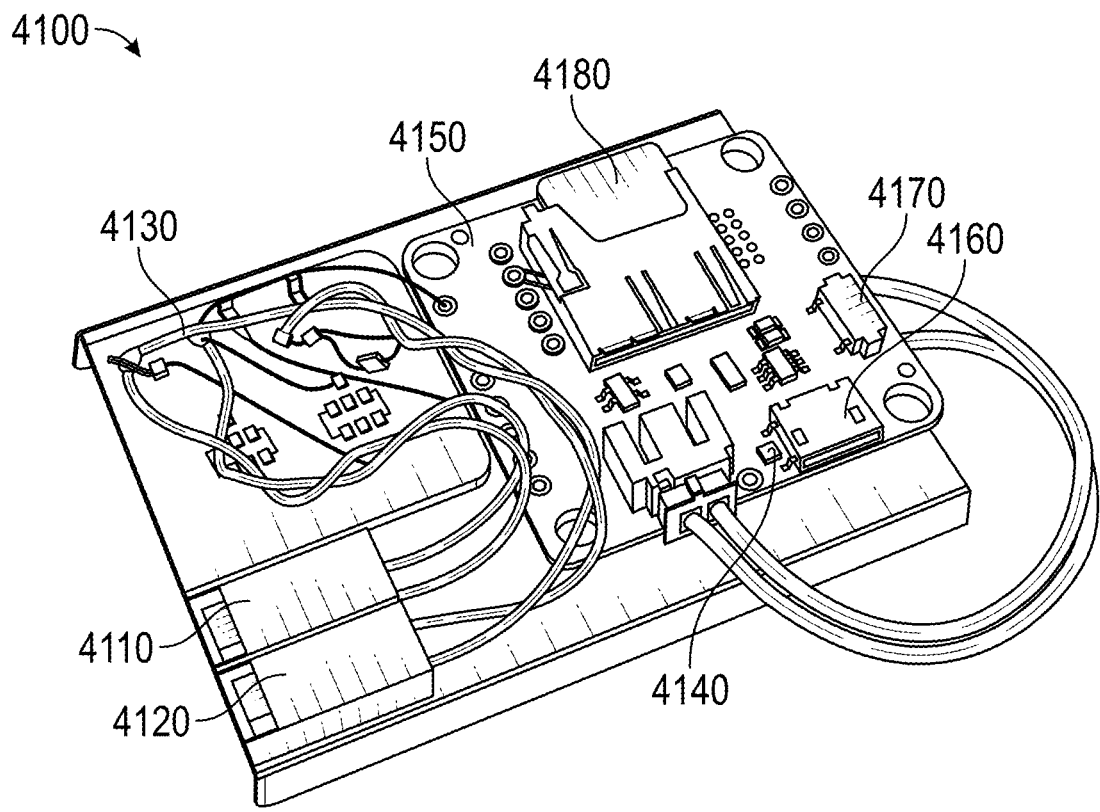
FIG. 15A illustrates a load monitoring apparatus with its housing removed according to some embodiments.

FIG. 15A illustrates a load monitoring apparatus 4100, which can be an example of the load monitoring apparatus 4010 with its housing removed. The load monitoring apparatus 4100 can include pressure inputs 4110, 4120, signal processing circuitry 4130, an accelerometer 4140, a power source 4150, a communication interface 4160, a user interface 4170, and a memory device 4180.

The pressure inputs 4110, 4120 can receive pressure input signals from pressure sensors, such as the pressure sensors 4020, 4030. The signal processing circuitry 4130 can, in turn, process pressure data received from the pressure inputs 4110, 4120.

The power source 4150 can, for example, be a battery, which may be rechargeable. The communication interface 4160 can be used to provide power to the power source 4150, program or adjust settings of the load monitoring apparatus 4010, or output monitored or determined load data to an external device.

The user interface 4170 can be used to activate and deactivate operation of the load monitoring apparatus 4100. For example, the user interface 4170 may be or include a toggle switch configured to control supply power to one or more components of the load monitoring apparatus 4100.

The memory device 4180 can be used store program instructions or gathered or determined data for the load monitoring apparatus 4100. In some implementations, the memory device 4180 may have sufficient capacity to store 70 days of gathered or determined data.

Figure 15B:
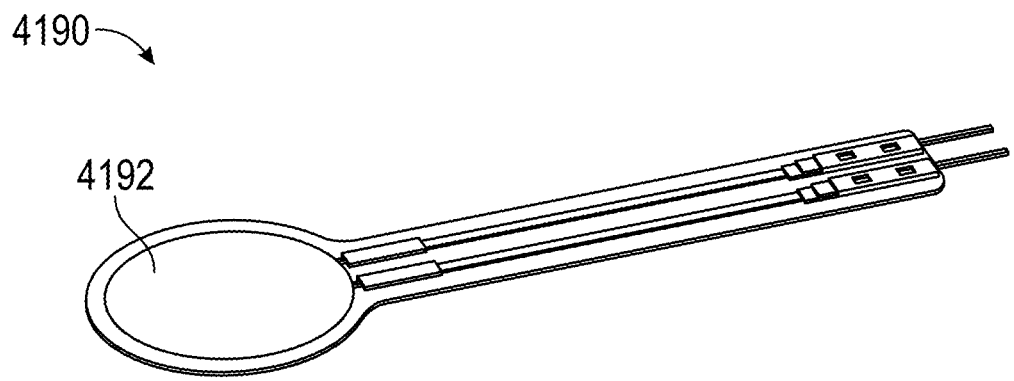
FIG. 15B illustrates a pressure sensor according to some embodiments.

FIG. 15B illustrates a pressure sensor 4190, which can be an example of one of the pressure sensors 4020, 4030. The pressure sensor 4190, for instance, can include a pad 4192 with a capacitive or resistive sensor that adjusts its capacitance or resistance responsive to pressure.

Figure 16:
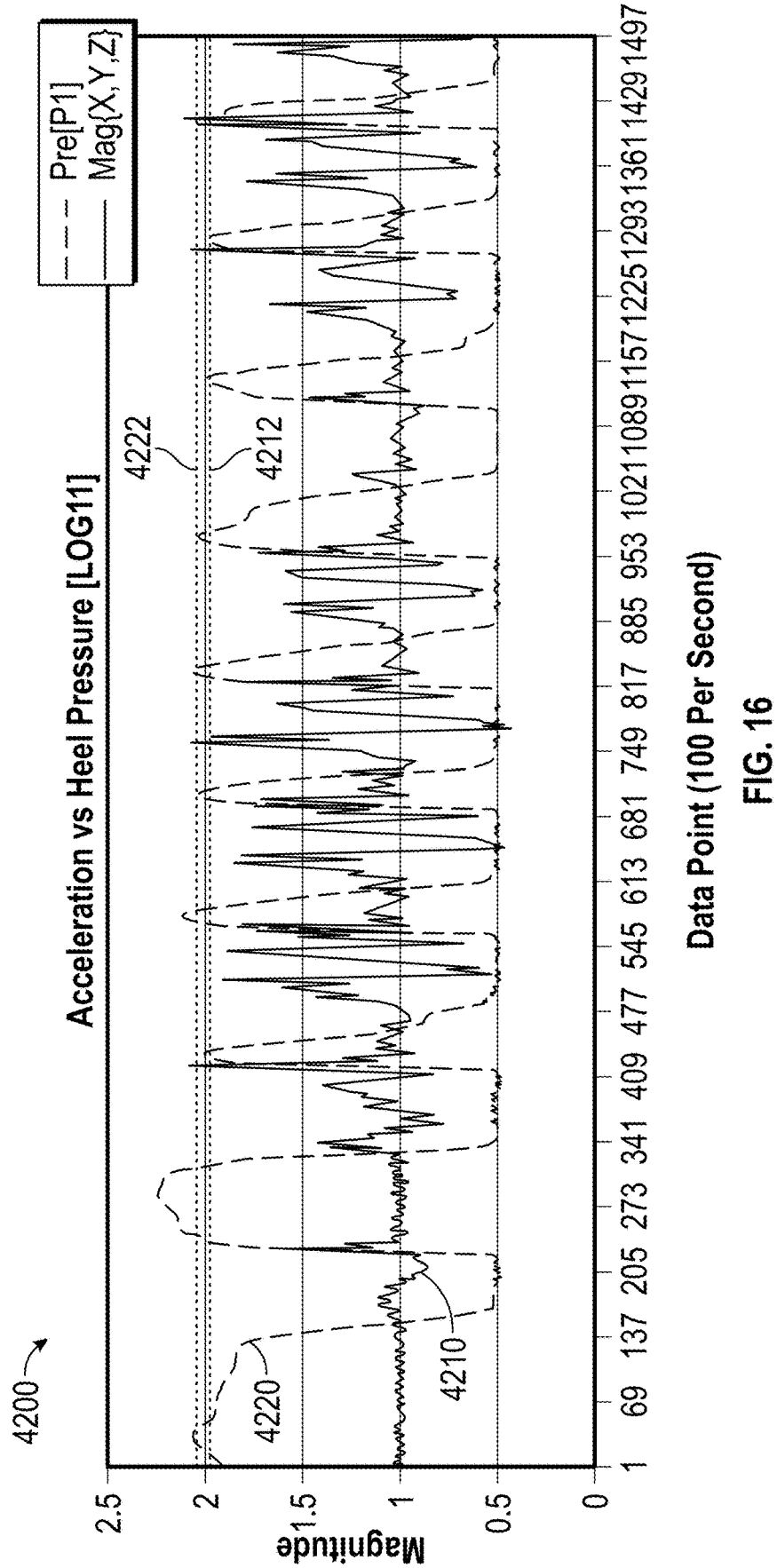
FIG. 16 illustrates a plot of detected magnitudes during operation of the monitoring system of FIG. 14 according to some embodiments.

FIG. 16 illustrates a plot 4200 of detected magnitudes during operation of the monitoring system 4000 of FIG. 14. The plot 4200 includes an acceleration waveform 4210 and a pressure waveform 4220. The acceleration waveform 4210 can be determined from a magnitude of acceleration along three different axes, such as an absolute magnitude in the x-axis, y-axis, and z-axis. The plot 4200 notably highlights that the acceleration waveform 4210 can be used to determine activity of the leg 4002, including loading of the leg 4002 by stepping and over-impacting a pressure ulcer on the foot of the leg 4002.

Spikes in the pressure waveform 4220 can typically indicate that an individual wearing the load monitoring apparatus 4010 has taken a step with the leg 4002. As can be seen from the plot 4200, spikes and changes in the acceleration waveform 4210 have a high degree of correlation to the spikes and changes in the pressure waveform 4220. In particular, the spikes in acceleration waveform 4210 that approximately reach a maximum acceleration magnitude 4212 can tend to occur when the spikes in the pressure waveform 4220 approximately reach a maximum pressure magnitude 4222. Accordingly, the spikes in acceleration waveform 4210 that approximately reach the maximum acceleration magnitude 4212 can, for example, be used to infer that the individual has stepped with the leg 4002.

Further analysis has shown that the acceleration waveform 4210 and the pressure waveform 4220 maintain such a high degree of correlation that acceleration can, for example, be used to predict pressure within ±30% of an actual pressure 95% of the time. In one implementation with use on a particular individual, an absolute magnitude of measured acceleration in in the x-axis, y-axis, and z-axis was determined to differ from measured pressure by a multiplier of 1.14 and with a standard deviation of 0.18. This multiplier can moreover be understood as a constant that depends on one or more patient-specific characteristics, such as patient weight or heal surface area, which can be known prior to monitoring an individual.

The acceleration waveform 4210 can be used to detect loading of the leg 4002 by analyzing magnitude variations indicative of a swing of the leg 4002, such a foot swing from stepping forwards. The data points around data point 1379 in the plot 4200 can, for instance, be indicative of a foot swing.

Figure 17A:
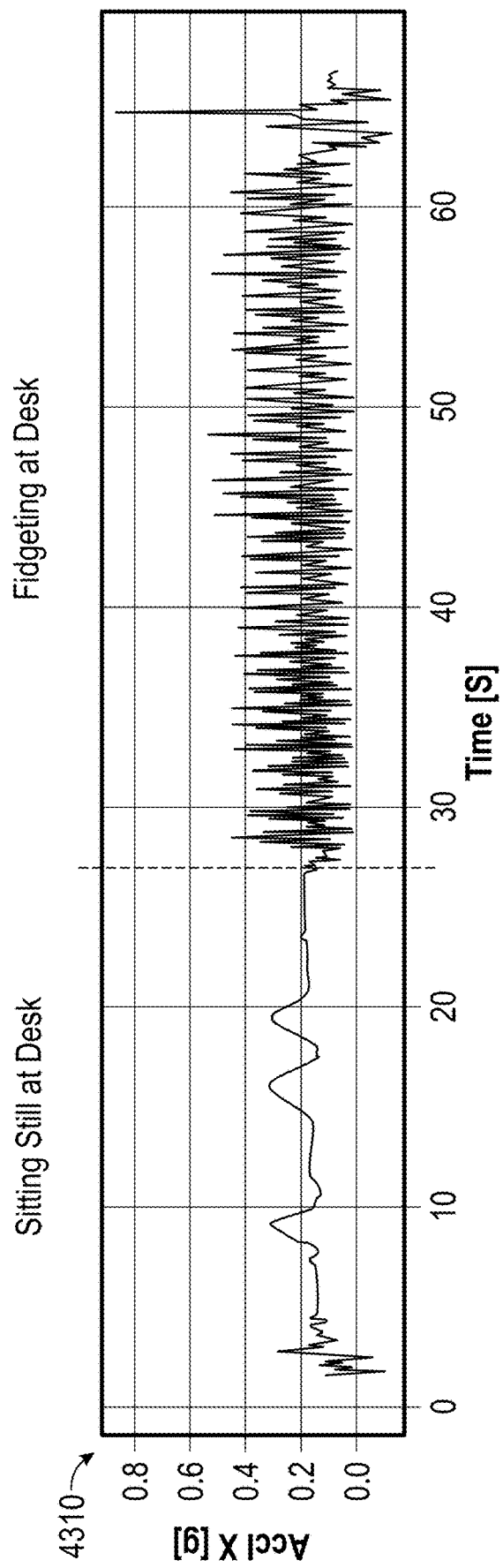
FIGS. 17A, 17B, and 17C illustrate plots of acceleration magnitudes in multiple axes during operation of the monitoring system of FIG. 14 according to some embodiments.
Figure 17B:
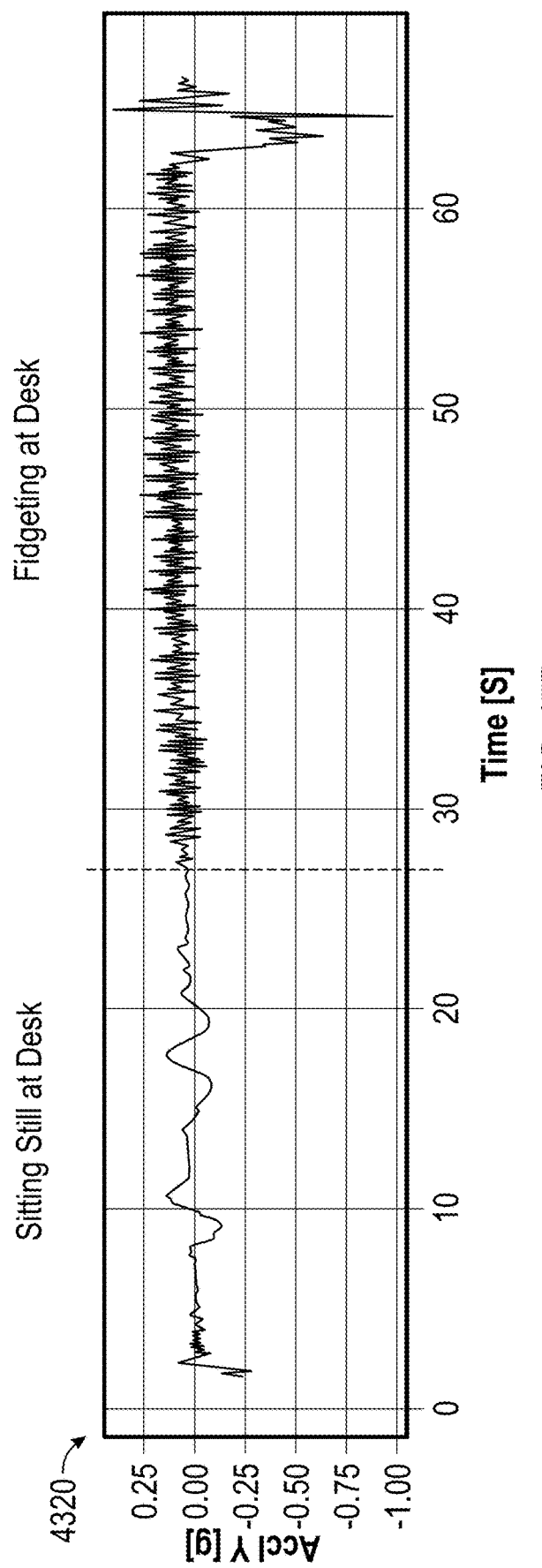
Figure 17C:
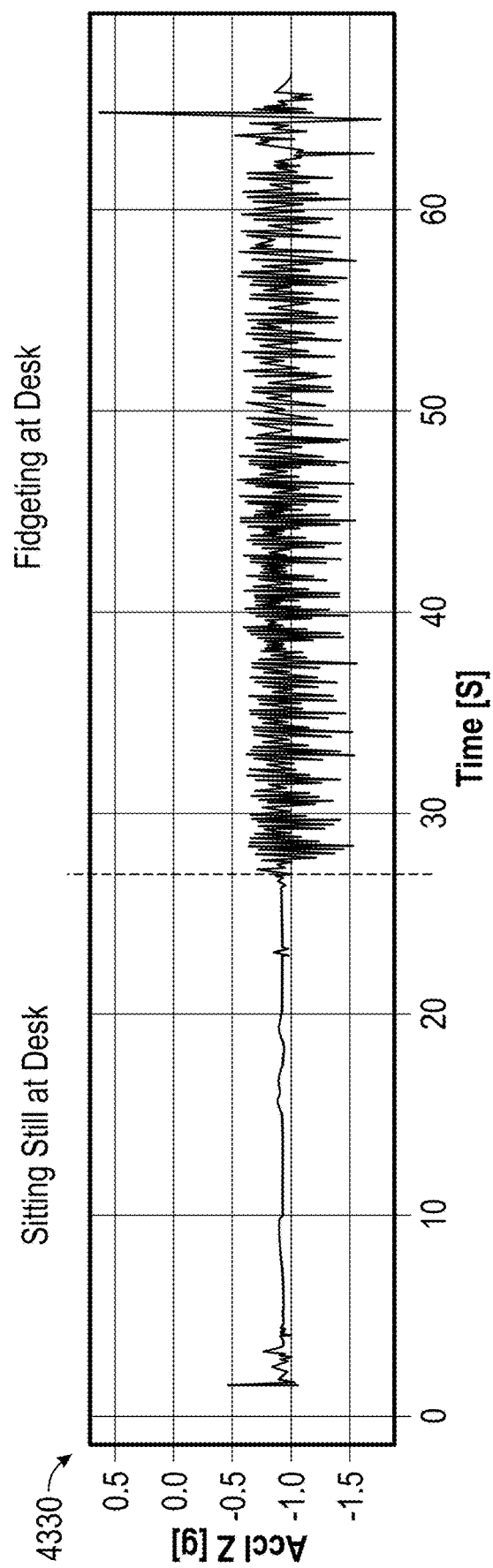

FIGS. 17A, 17B, and 17C illustrates plots 4310, 4320, 4330 of acceleration magnitudes in multiple axes during operation of the monitoring system 4000 of FIG. 14. The plots 4310, 4320, 4330 can include a time period expanding from 0 to 27 seconds in which the leg 4002 was remaining still while sitting at a desk. In addition, the plots 4310, 4320, 4330 can include a time period expanding from 27 to 67 seconds in which the leg 4002 was fidgeting while at the desk. The plots 4310, 4320, 4330 notably show greater signal variation when fidgeting than when sitting still.

Figure 17D:
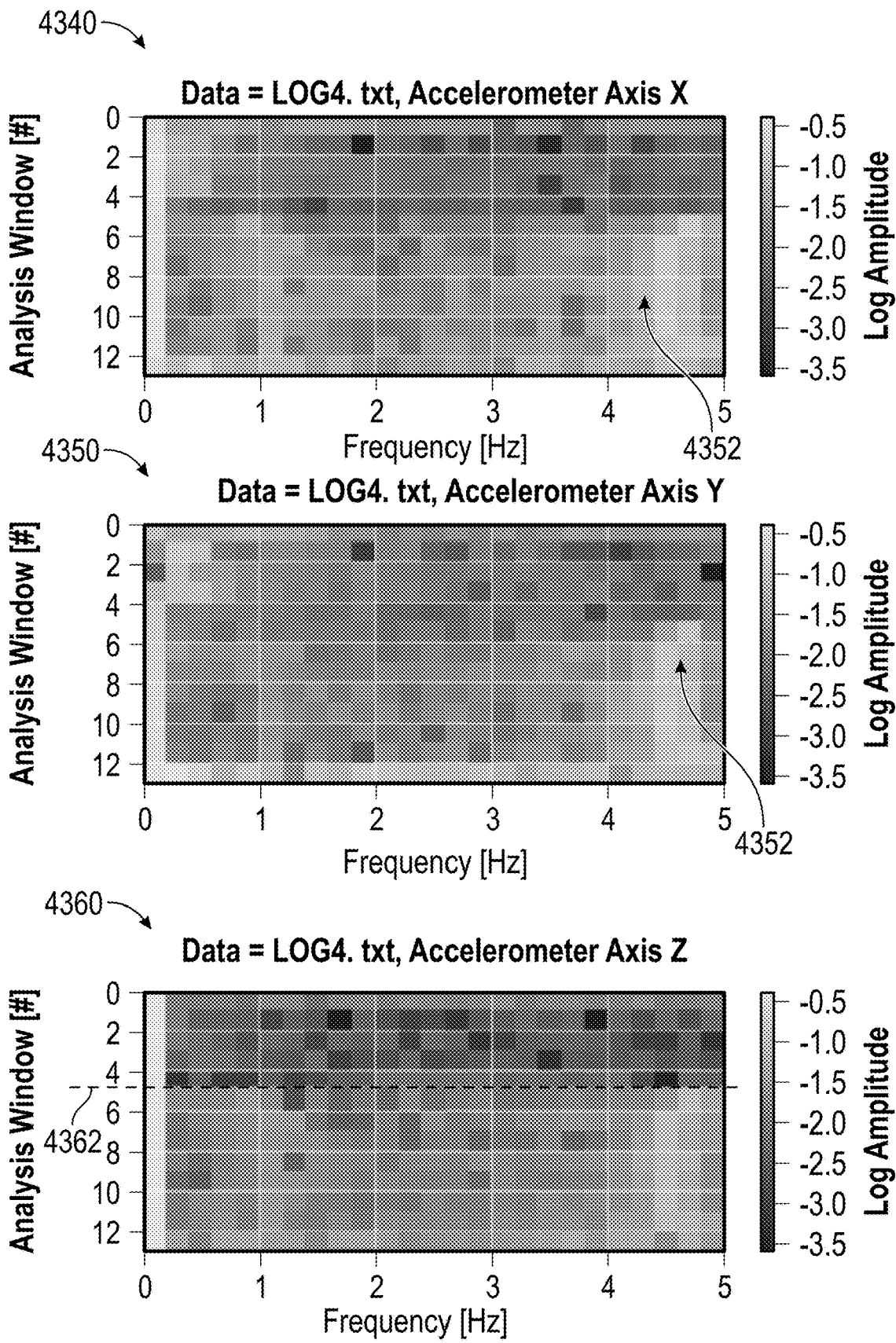
FIG. 17D illustrates plots of spectral distributions of the plots of FIGS. 17A, 17B, and 17C according to some embodiments.

FIG. 17D illustrates plots 4340, 4350, 4360 of spectral distributions of the plots 4310, 4320, 4330. The plots 4340, 4350, 4360 can, for example, be determined from taking frequency transforms, such as fast Fourier transforms (FFTs), of the plots 4310, 4320, 4330. The values from 0 to 5 in y-axis of the plots 4340, 4350, 4360 can provide data corresponding to sitting still, and the values from 5 to 13 in y-axis of the plots 4340, 4350, 4360 can provide data corresponding to fidgeting. A transition line 4362 depicts a timing of transitioning from sitting still to fidgeting for the z-axis.

As can be seen from the plots 4340, 4350, 4360, the plots 4340, 4350, 4360 can show a greater magnitude signal around 4 Hz during fidgeting than sitting still. An indicator 4352 identifies a region around 4 Hz in which the plots 4340, 4350, 4360 show the relatively higher magnitude signal.

Figure 18A:
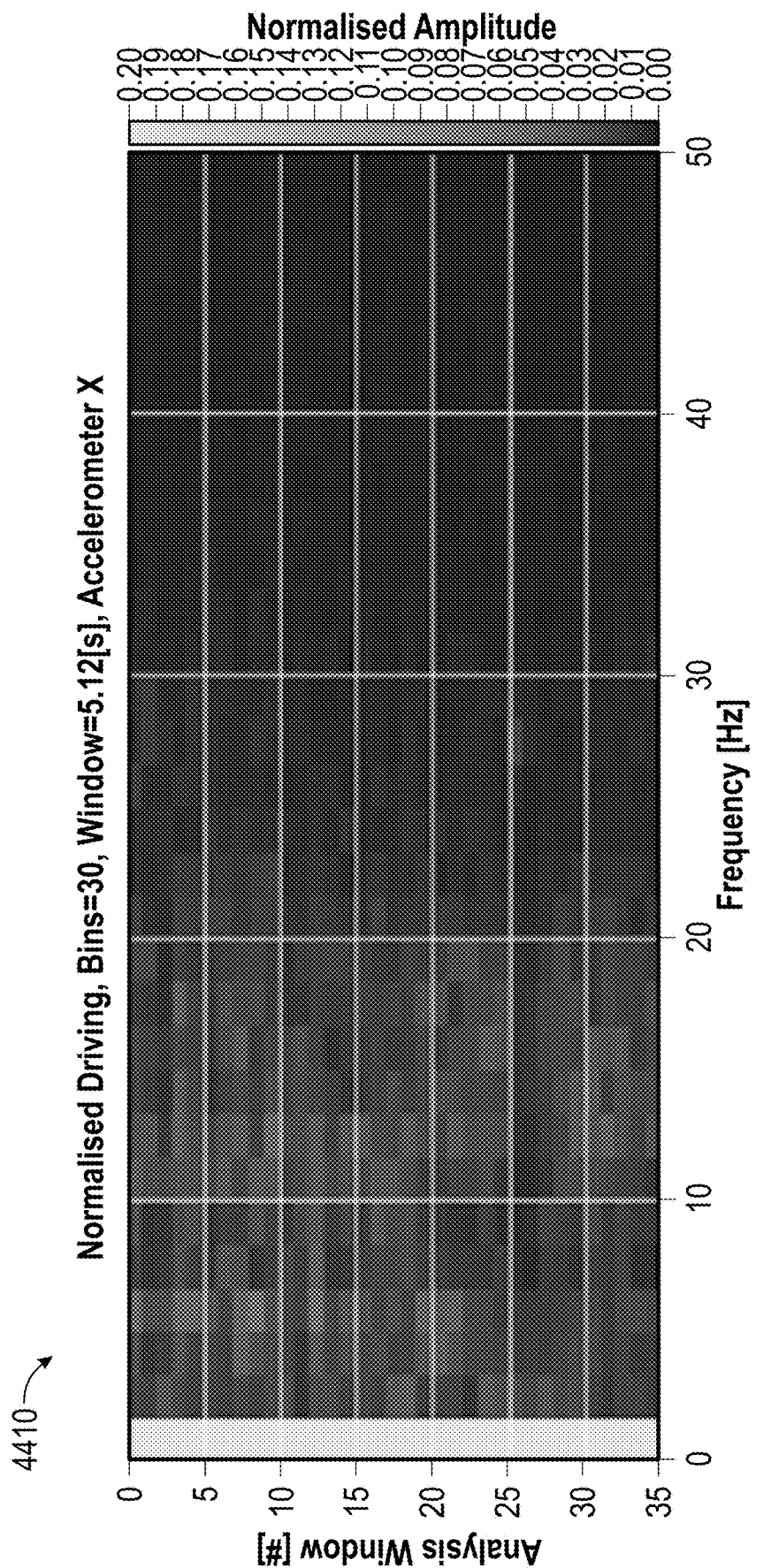
FIGS. 18A, 18B, and 18C illustrate plots of spectral distributions for acceleration magnitudes in multiple axes during operation of the monitoring system of FIG. 14 according to some embodiments.
Figure 18B:
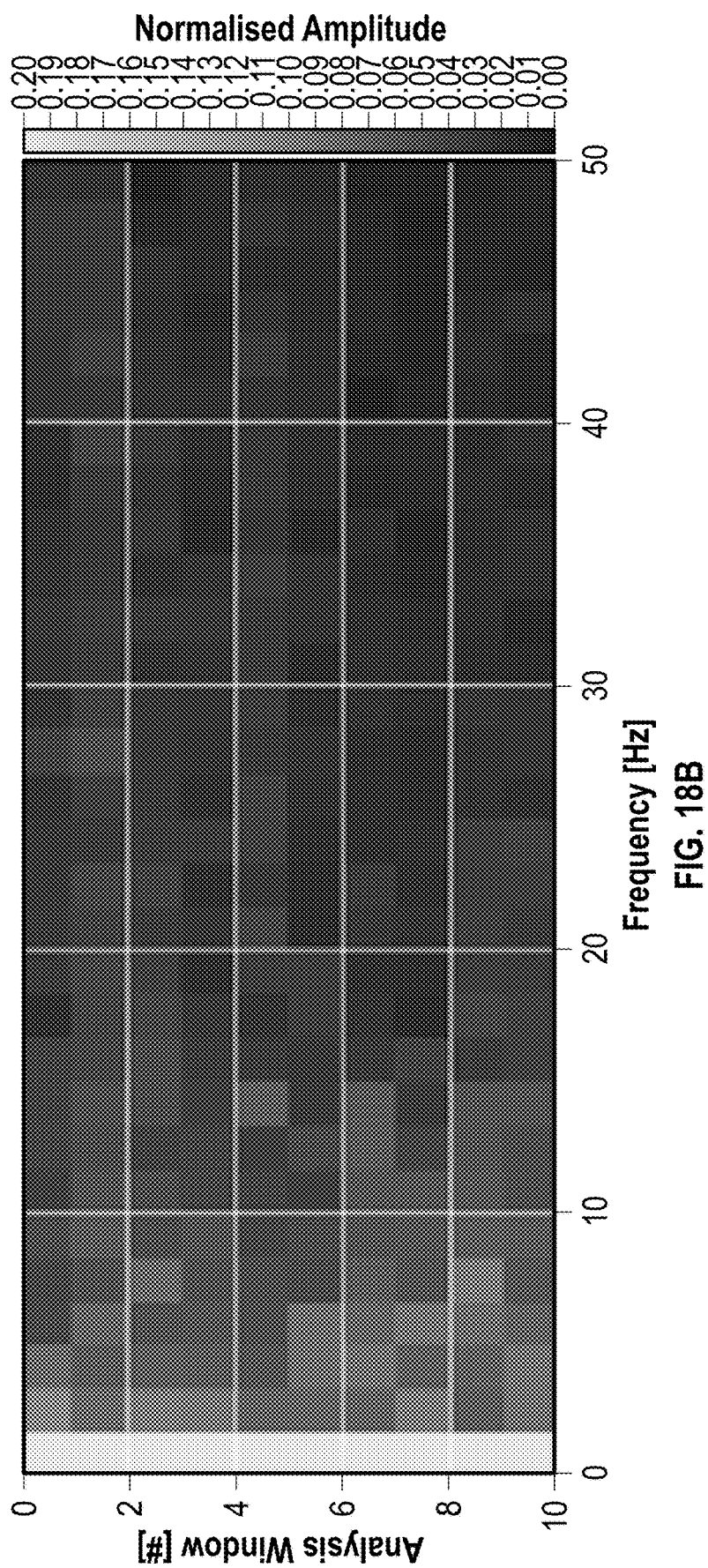
Figure 18C:
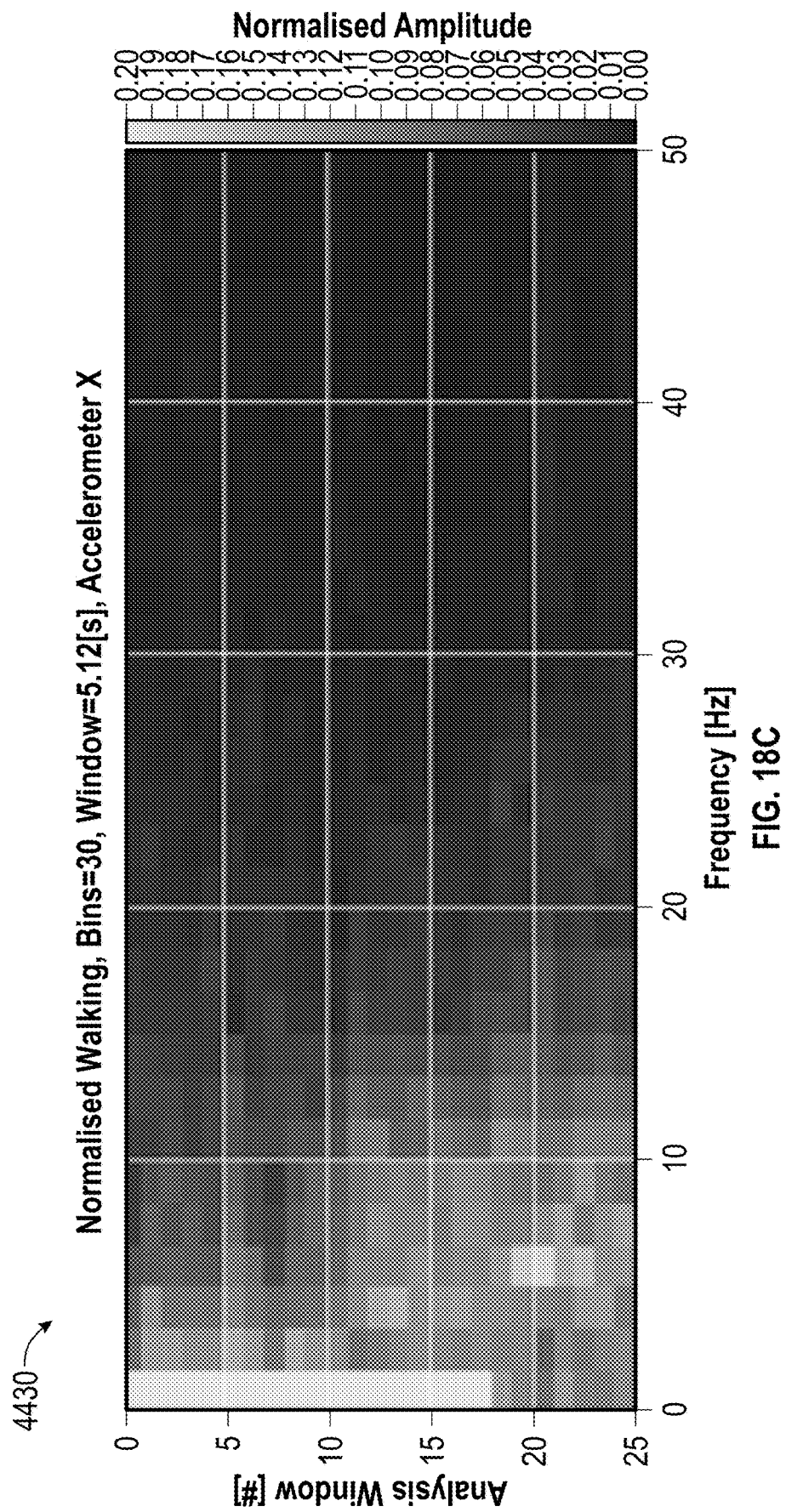

FIGS. 18A, 18B, and 18C illustrates plots 4410, 4420, 4430 of spectral distributions for acceleration magnitudes in multiple axes during operation of the monitoring system 4000 of FIG. 14. The plot 4410 depicts normalized acceleration during driving. The plot 4420 depicts normalized acceleration during sitting. The plot 4430 depicts normalized acceleration during walking. As can be seen from the plots 4410, 4420, 4430, frequencies in the range of 0 Hz to 15 Hz may include features that distinguish driving, sitting, and walking from one another. Such information advantageously, in certain embodiments, can be used to determine an offloading compliance by the leg 4002 and enable the load monitoring apparatus 4010 to discourage or change behaviors which may increase risk of injury or reduce time to heal.

An activity classification can be determined from the spectral distribution of one or more of the plots 4410, 4420, 4430. The activity classification can be indicative of a type of activity engaged in by the leg 4002 while wearing the load monitoring apparatus 4010. The activity classification can, for example, be one of driving, sitting, or walking, among other possible activities.

The activity classification can, in some implementations, be determined by a comparison, such as a ratio, of an amplitude of the spectral distribution over a first frequency range and an amplitude of the spectral distribution over a second frequency range. In one example, the first frequency range can be 0 Hz to 1.67 Hz in the second frequency range can be 1.67 Hz to 3.33 Hz. In this example and with the spectral distribution of the plots 4410, 4420, 4430, the ratios for driving, sitting, and walking can respectively be 33.4, 7.2, and 3.2. The ratios accordingly can be compared to one another or one or more thresholds associated with driving, sitting, or walking to infer an activity engaged in by the leg 4002. In yet other examples, other frequency ranges for the first and second frequency ranges may be used.

Additionally or alternatively, the activity classification can be determined from angular response or total magnitude of vibration associated with the leg 4002.

Figure 19:
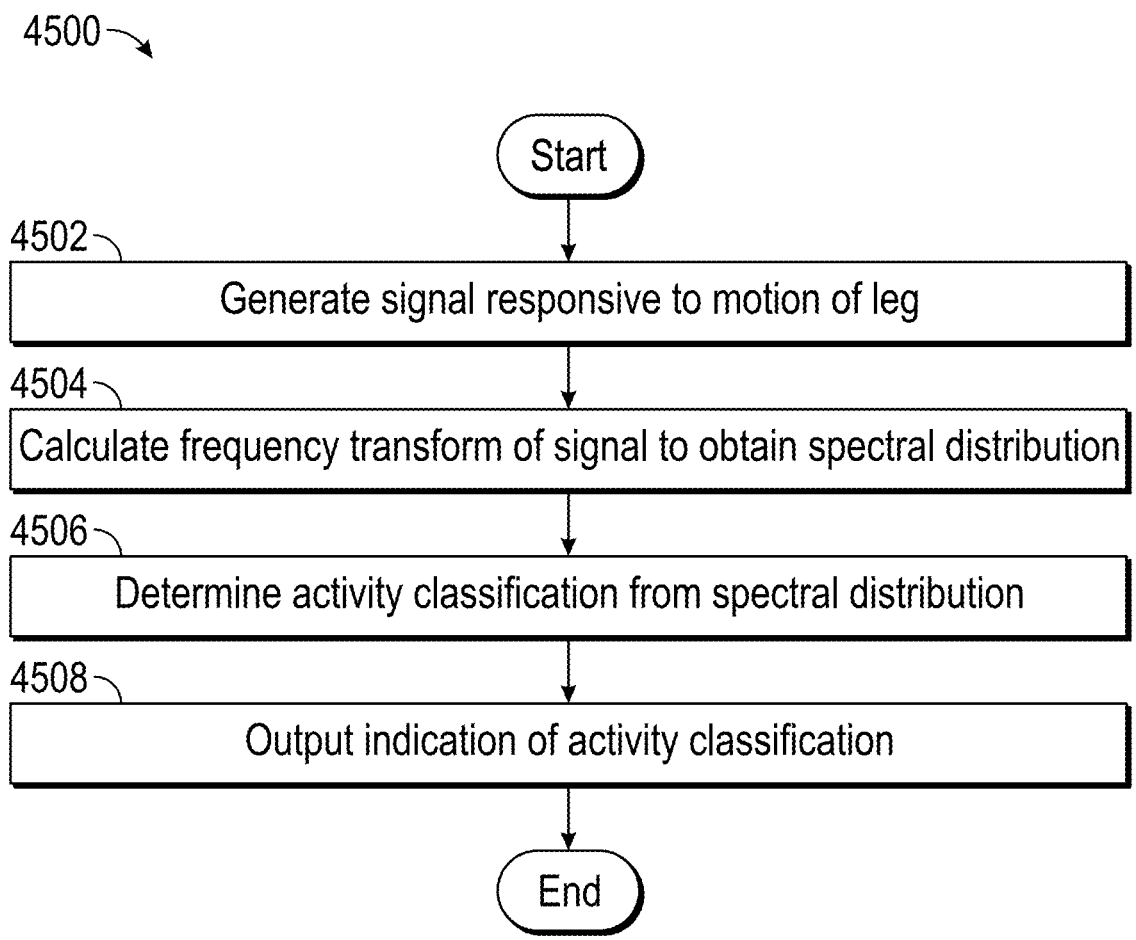
FIG. 19 illustrates a process for monitoring loadbearing according to some embodiments.

FIG. 19 illustrates a process 4500 for monitoring load-bearing performable by a device, such as the load monitoring apparatus 1002 of FIG. 4. For convenience, the process 4600 is described in the context of the load monitoring apparatus 1002, but may instead be implemented in other systems described herein, or by other computing systems not shown. The process 4500 can advantageously, in certain embodiments, enabled the load monitoring apparatus 1002 determine an activity classification for a user of the load monitoring apparatus 1002.

At block 4502, the process 4500 can generate a signal responsive to motion of the leg. The load monitoring apparatus 1002 can, for example, be attached to a leg of the individual, and the sensor(s) 1020 can include an accelerometer that generate a signal, such as one or more of x-axis, y-axis, and z-axis waveforms, responsive to leg motion.

At block 4504, the process 4500 can calculate a frequency transform of the signal to obtain a spectral distribution for the signal. The controller 1010 can, for example, calculate a FFT for each axis of the signal.

At block 4506, the process 4500 can determine an activity classification from the spectral distribution. The controller 1010 can, for instance, determine a type of activity engaged in by the individual while wearing the accelerometer. The activity classification can, in some instances, one of driving, sitting, or walking, among other types of activities.

In some embodiments, the process 4500 can additionally or alternatively determine (i) the activity classification from a time domain representation of the signal like a magnitude of the signal, (ii) the activity classification from a position of the body part 1006 over time, such as a distance traversed in along an x-axis, y-axis, and z-axis, like from double-integrating or cumulative summing the signal, (iii) the activity classification from one or more additional sensors, such as a pressure sensor, a gyroscope, a magnetometer, or an optical sensor, or (iv) a pressure or load on the body part 1006, such as by calculating pressure from providing the signal as an input to a function that calculates pressure as a function of acceleration. When the process 4500 determines the activity classification from the pressure sensor, the pressure can, in one example, be an absolute pressure sensor and used to monitor small changes in altitude (such as with a resolution of around 5 cm, for example) to detect raising and lowering of the absolute pressure sensor that may be respectively indicative of unloading or loading of the leg.

At block 4508, the process 4500 can output an indication of the activity classification. The user interface 1060 can, for example, visually or audibly present the indication.

In some embodiments, a system for monitoring loadbearing is disclosed. The system can include a housing that attaches to a leg of an individual below a knee of the individual. The housing can support an accelerometer that generate a signal responsive to motion of the leg during a first time period and a second time period. in addition, the system can include a controller configured to: determine that the leg is supporting a weight during the first time period based at least on motion during the first time period reflecting a muscle tremor by the leg that occurs when the leg is not supporting at least a baseline amount of weight, determine that the leg is not supporting the weight during the second time period based at least on motion during the second time period not reflecting the muscle tremor by the leg that occurs when the leg is not supporting at least the baseline amount of weight, and responsive to determining that the leg is not supporting the weight during the second time period, output for presentation an indication denoting to move the foot.

The system of the preceding paragraph can include one or more the following features: The controller can, prior to determining that the leg is supporting the weight during the first time period and not supporting the weight during the second time period, profile the muscle tremor by the leg that occurs when the leg is not supporting at least the baseline amount of weight. The controller can determine a degree to which motion during the first time period reflects the muscle tremor by the leg that occurs when the leg is not supporting at least the baseline amount of weight. The controller can determine a value from the degree, the value being indicative of a magnitude of the weight supported by the leg during the first time period. The controller can output the value for presentation, such as on a user interface. The controller can filter a vehicle motion from the signal. The vehicle motion can be a car motion, a lorry motion, an airplane motion, or a train motion.

Load Monitoring with Negative Pressure Wound Therapy

As described herein, monitoring loading of a body part can be performed in a negative pressure environment. For example, monitoring loading of the body part can be performed in conjunction with provision of negative pressure wound therapy.

In some embodiments, a load monitoring apparatus, such as the load monitoring apparatus 1002 of FIG. 4, includes a negative pressure source, such as the negative pressure source 1014. The body part, such as a foot, can be dressed with a dressing configured to create and maintain a substantially fluid tight seal so that negative pressure can be maintained under the dressing. The dressing can be any of negative pressure wound dressings described herein. The negative pressure source can be configured to draw down pressure under a dressing to a target negative pressure setpoint and maintain the pressure under the dressing to substantially match the setpoint. As described herein, the negative pressure source can be operated by a controller, such as the controller 1010.

Figure 20A:
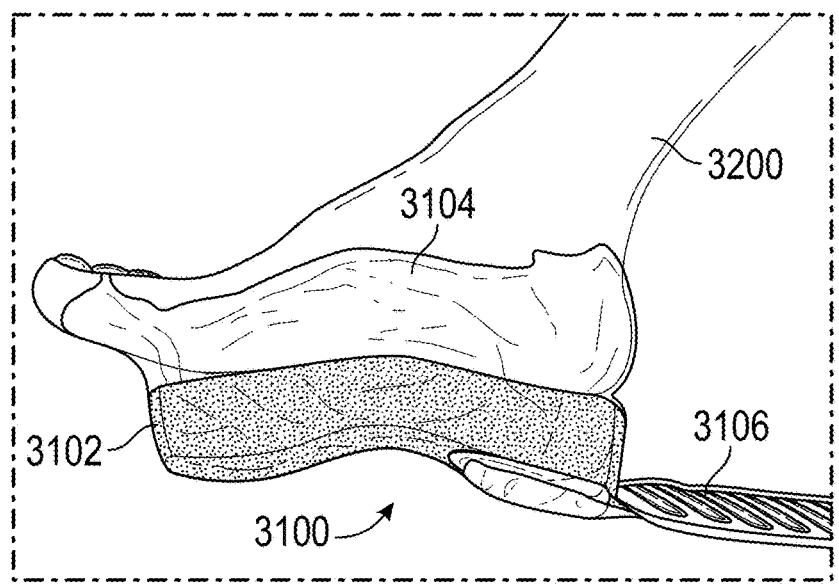
FIGS. 20A and 20B illustrate a load monitoring apparatus used with negative pressure wound therapy according to some embodiments.
Figure 20B:
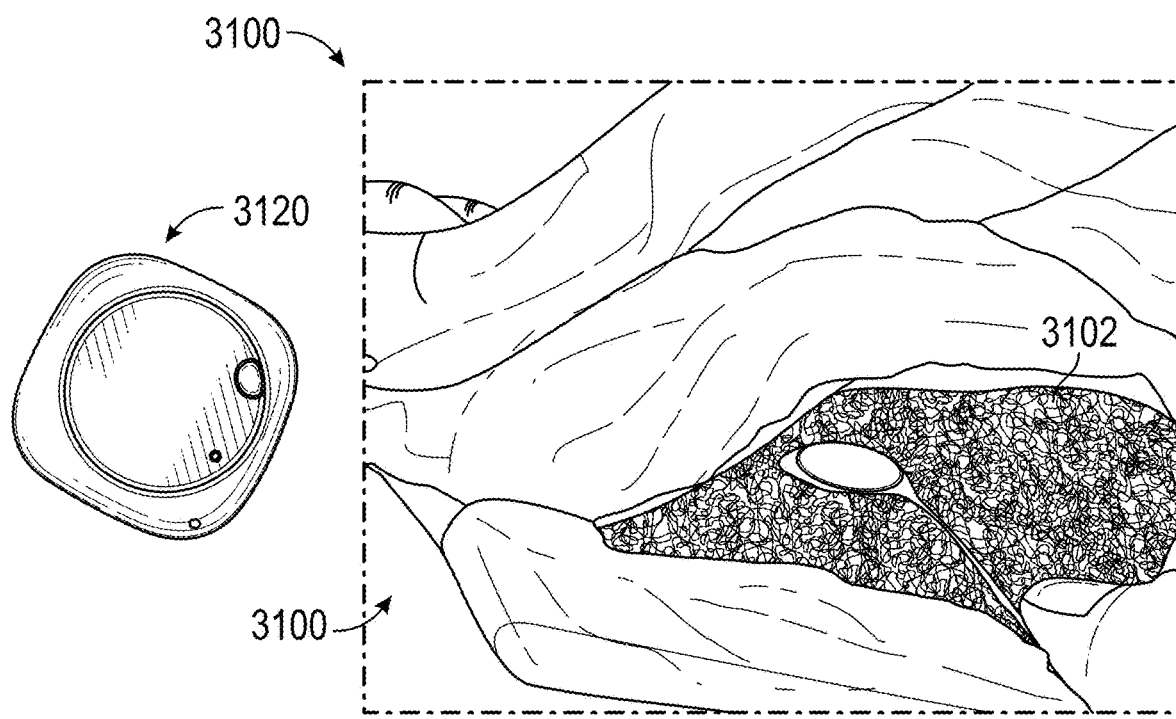

FIGS. 20A and 20B illustrate a load monitoring apparatus 3100 used with negative pressure wound therapy according to some embodiments. As is illustrated, the load monitoring apparatus 3100 is applied to a foot 3200 and can be used to measure loading of the foot 3200. The load monitoring apparatus 3100 includes a foam dressing 3102 positioned over a part of the sole of the foot. The foam dressing 3102 is sealed with drape 3104. Port 3106, which is illustrated as SOFT PORT as described herein, connects the foam dressing 3102 to a negative pressure source (not shown). With reference to FIG. 20B, a sensor 3120 is positioned in a cutout in the foam dressing 3102. The sensor 3120 can measure one or more of pressure in a fluid flow path (which includes volume under the foam dressing 3102) connecting the negative pressure source to the foam dressing 3102 or motion data associated with movement of the foot 3200. In some implementations, the sensor 3120 can measure motion data and pressure can be measured by a pressure sensor associated with the negative pressure source as described herein. The load monitoring apparatus 3100 can include a controller as described herein. The sensor 3120 can communicate with the controller wirelessly or via one or more wires.

For brevity, the foregoing and following description of the load monitoring apparatus 3100 and its operation relates to positioning on the sole of the foot and measuring loading of the foot, in some implementations the apparatus can be positioned on any part of the foot or any other body part as described herein. The foregoing and following description is applicable to determining loading or unloading of any body part. Although foam dressing sealed by drape and connected to the negative pressure source by SOFT PORT connector are illustrated, any dressings or ports described herein can be alternatively or additionally used. The pressure sensor can be positioned anywhere in the fluid flow path, including under the dressing as illustrated in FIG. 20B or outside the volume enclosed by the dressing. For example, the pressure sensor can be positioned at or near inlet of the negative pressure source. The motion sensor can be positioned anywhere on the body part, such as the foot. For example, the motion sensor can be positioned under the dressing as illustrated in FIG. 20B or outside the volume enclosed by the dressing.

In some implementations, the target negative pressure setpoint can provide a baseline pressure under the dressing (or in the fluid flow path) for detecting or monitoring loading of the body part. In case of a foot, for example, loading the foot dressed with a dressing that creates a sealed environment under the dressing can cause pressure under the dressing to rise above the target negative pressure setpoint (toward or above atmospheric pressure) in response to the loading, which can cause dressing to compress. Negative pressure source can be controlled to counteract this rise in pressure by being activated to substantially restore the pressure under the dressing to substantially match the target negative pressure setpoint. Accordingly, loading of the foot can be detected by sensing the rise (due to the loading) in pressure under the dressing. Additionally or alternatively, loading of the foot can be detected by sensing subsequent return of the pressure under the dressing to the baseline pressure associated with the target negative pressure setpoint. Subsequent unloading of the foot, which can cause the dressing to decompress, can cause the pressure under the dressing to fall below the target negative pressure setpoint, and can be similarly detected.

Figure 21:
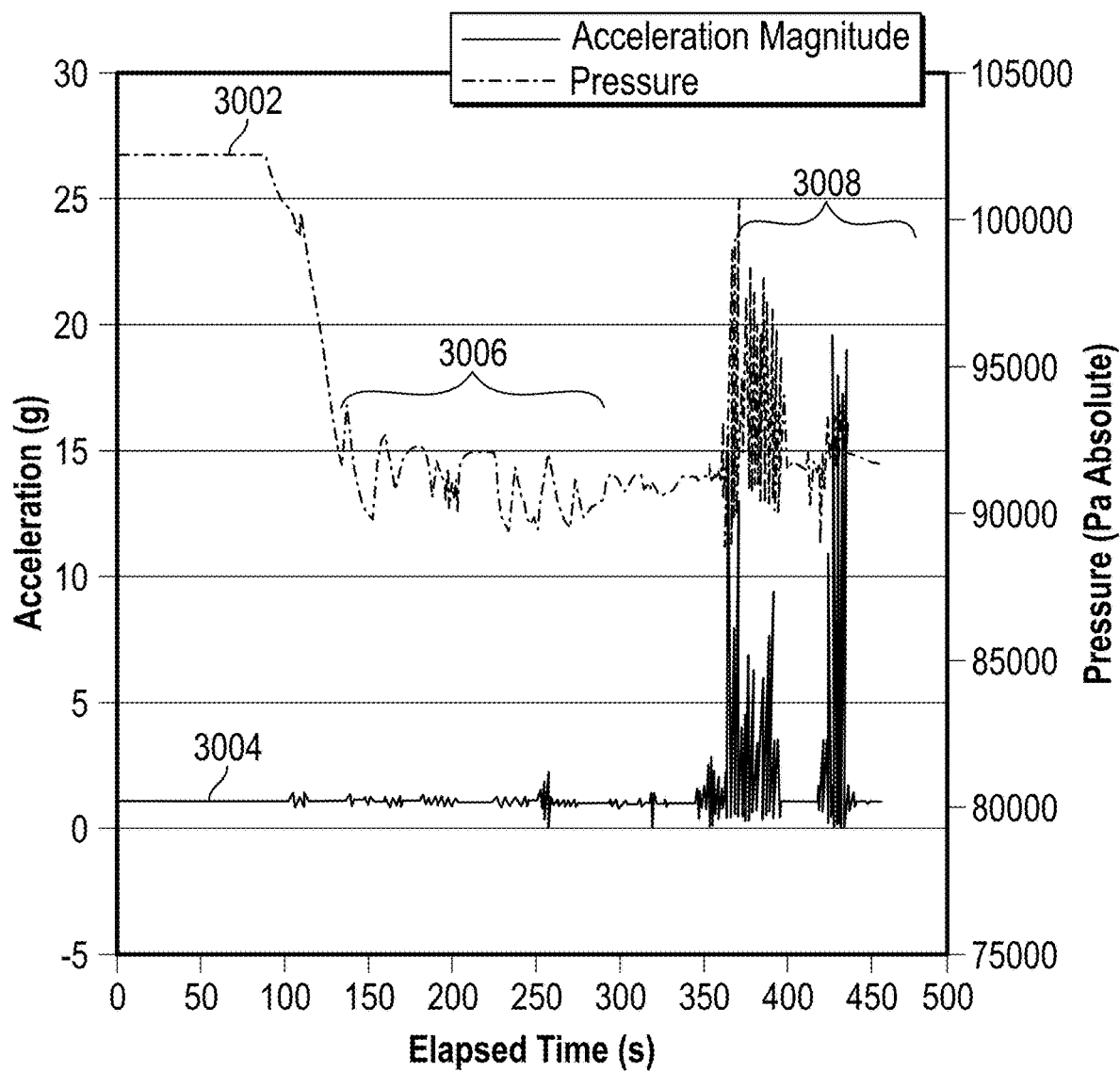
FIGS. 21 and 22 illustrates plots of pressure and movement for monitoring loadbearing in presence of negative pressure according to some embodiments.
Figure 22:
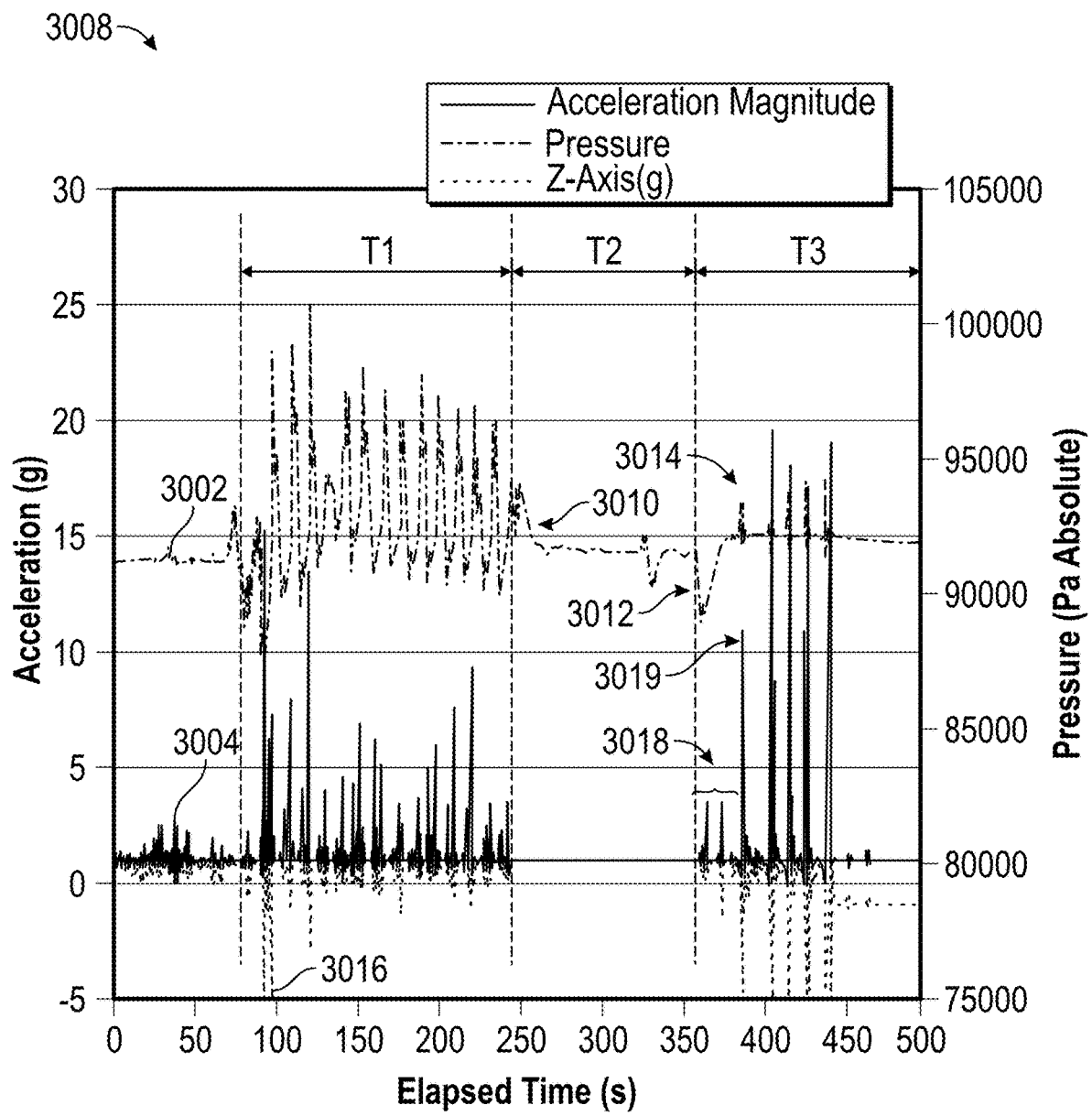

Detection of loading or unloading by the load monitoring apparatus 3100, such as by the controller, is shown in FIGS. 21 and 22 according to some embodiments. FIG. 21 illustrates measurement of pressure (plot 3002) in the fluid flow path connecting the source of negative pressure to the dressing. X-axis illustrates elapsed time, and Y-axis illustrates magnitude of pressure. At approximately 90 seconds, the negative pressure source is activated and the pressure under the dressing is reduced to substantially match a target negative pressure setpoint. During time period 3006, the dressing compresses as gas is removed from a volume under the dressing. Peaks and troughs in the pressure measurement can be due to presence of one or more leaks in the fluid flow path.

Segment 3008 depicts various types of loading of the foot. FIG. 22 illustrates the enlarged version of the segment 3008. Time period T1 illustrates changes due to walking, time period T2 illustrates changes due to standing still, and time period T3 illustrates changes due to a free-fall drop and impact of the artificial foot, which can be indicative of climbing the stairs (for example, going down the stairs) or jumping.

As is illustrated by plot 3002, during time period T1 negative pressure under the dressing decreases (or rises toward atmospheric pressure) when the foot is loaded. For example, decreases in the negative pressure can be associated with a patient placing weight on the foot when walking. The negative pressure source can be controlled to counteract such decreases in the negative pressure by being activated to substantially restore the target negative pressure setpoint. This is why pressure spikes can be observed during time period T1. One or more of such pressure spikes (decreases or increases) can be indicative of loading the foot, which can be detected by the controller. Alternatively or additionally, detection of such pressure spikes repeating at a certain frequency (or frequencies) can be indicative of walking, running, or the like, which can be detected by the controller.

Time period T2 illustrates changes due to standing still. At or near the beginning of time period T2, the negative pressure source can be controlled to counteract the decrease in negative pressure from loading of the foot by being activated and attempting to substantially restore the target negative pressure setpoint. This is illustrated by the spike 3010 followed by gradual increase in negative pressure. Such spike in pressure associated with loading of the foot followed by gradual increase in negative pressure can be indicative of standing still, which can be detected by the controller.

Time period T3 illustrates changes due to offloading the foot at 3012 followed by simulated going down the stairs or jumping at 3014. As is illustrated, when the load is removed at 3012, the negative pressure under the dressing increases below the target negative pressure setpoint. As explained herein, this can occur due to decompression of the dressing when the load is removed. This can be followed by reducing operation of the negative pressure source to achieve substantially the target negative pressure setpoint. Such spike in pressure associated with unloading of the foot followed by gradual decrease in negative pressure can be indicative of unloading, which can be detected by the controller.

At 3014 (and repeated four more times), going down the stairs or jumping is simulated and can cause a decrease in the negative pressure under the dressing. As is shown, the target negative pressure setpoint can be substantially restored under the dressing via operation of the negative pressure source. Spike 3014 can have shorter duration than the spikes during time period T1 (walking), spike 3010 during time period T2 (standing), or spike 3012 (unloading). Such spike in pressure associated with going down the stairs or jumping followed by rapid increase in negative pressure can be indicative of going down the stairs or jumping.

Alternatively or additionally to detecting or classifying a particular activity that loads the foot, such as walking, running, standing, climbing the stairs, jumping, or the like, duration of time over which the foot is loaded or duration of the activity can also be detected by the controller.

In some embodiments, monitoring motion of the foot can additionally or alternatively be used to determine foot loading or unloading, classify activity, determine duration, or the like. As described herein, motion can be measured by one or more motion sensors, such as one or more of an accelerometer, gyroscope, magnetometer, or the like. Such one or more motion sensors can be positioned on foot, such as under the dressing as illustrated in FIGS. 20A and 20B or near the foot. In some embodiments, the motion sensor can include a 3-axis accelerometer, 3-axis gyroscope, and 3-axis magnetometer. The accelerometer can be used to track the acceleration of the foot along x-axis, y-axis, or z-axis. The gyroscope can be used to track the orientation of the foot, such as raising or lowering the foot. The magnetometer can be used to determine the proximity of the foot to an orthopedic device as described herein.

With reference to FIGS. 21 and 22, plot 3004 illustrates acceleration magnitude obtained from a motion sensor. Plot 3016 in FIG. 22 illustrates acceleration along the z-axis, which is associated with up or down movement. Acceleration along x-axis and y-axis is not shown.

As is shown in FIG. 21, during time period 3006 when the negative pressure source operates to reach substantially the target negative pressure setpoint under the dressing, plot 3004 illustrates little or no movement. During time period of the segment 3008 (illustrated in greater detail in FIG. 22), plot 3004 illustrates movement of the foot associated with walking during time period T1, standing during time period T2, offloading and going down the stairs or jumping during time period T3. Based on motion data, the controller can distinguish pressure spikes or changes due to one or more leaks (time period 3006) from pressure spikes or changes due to movement (for example, during time period T1).

During time period T1, plot 3004 illustrates changes in the acceleration of the foot beginning during walking. The peaks in the acceleration magnitude can coincide with raising or lowering the foot during walking. The magnitude or cyclical nature of the peaks in the acceleration magnitude can alternatively or additionally provide indication that the patient is walking. The controller can analyze motion data to classify the activity as walking.

During time period T2, which is associated with standing, plot 3004 illustrates no changes in the acceleration magnitude. While plot 3002 illustrates that pressure under the wound dressing reaches substantially the target negative pressure setpoint, pressure data alone may not provide enough information to distinguish between standing and unloading of the foot as both activities may trigger similar changes in pressure. Because plot 3004 illustrates no changes in the acceleration magnitude, the controller can classify the activity as standing. If the foot was unloaded during time period T2 changes in acceleration due to unloading (for example, raising the foot) would have been detected. This is illustrated the beginning of time period T3, when the foot is unloaded. Unloading the foot is associated with changes 3018 in the acceleration magnitude During time period T3 going down the stairs or jumping is simulated, as is evidenced by the z-axis plot 3016 going toward zero. As is illustrated, spikes in acceleration magnitude, such as the spike 3019, are observed. The magnitude of the spikes associated with going down the stairs or jumping can be higher than the magnitude of the spikes associated with walking during time period T1. Frequency of the spikes associated with going down the stairs or jumping can be lower than the frequency of the spikes associated with walking. The controller can analyze motion data to distinguish walking from jumping or going down the stairs. The controller can further distinguish jumping from going down the stairs as the magnitude of acceleration spokes associated with jumping can be higher than that associated with going down the stairs.

Detection of the pressure or motion spikes, increases in pressure or motion, or decreases in pressure or motion described herein can be performed by comparing one or more of pressure or motion magnitude, frequency, or the like to a corresponding threshold (or thresholds). Suitable filtering techniques can be used prior to or during detection, including low-pass, band-pass, or the like.

Figure 23:
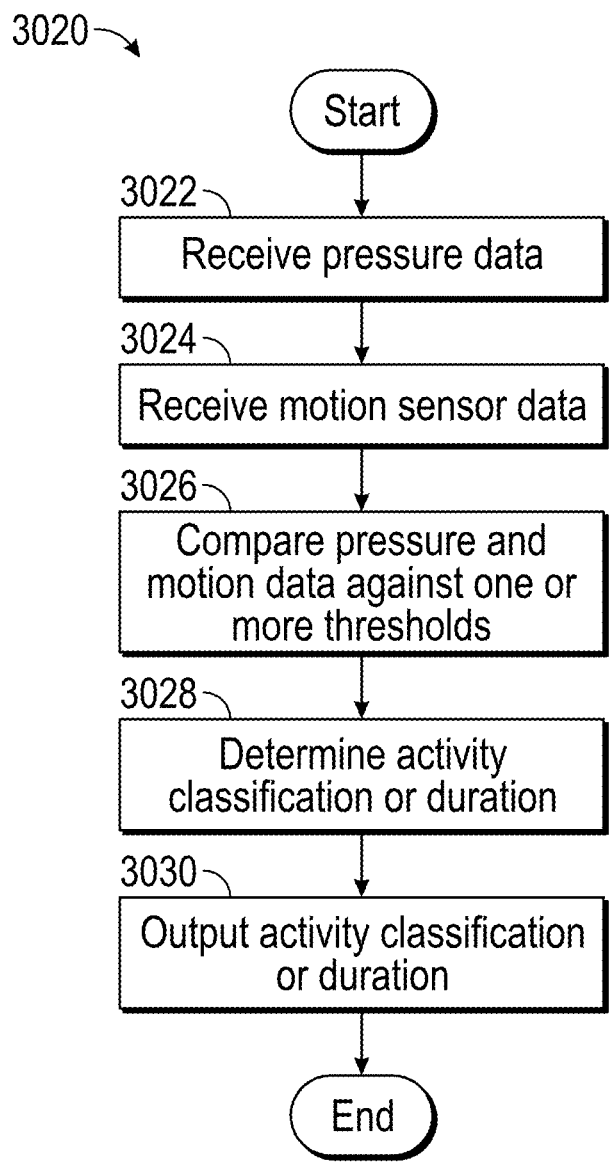
FIG. 23 illustrates a process for monitoring loadbearing according to some embodiments.

FIG. 23 illustrates a process 3020 for load monitoring according to some embodiments. The process 3020 can be executed by any one or more of the load monitoring systems or apparatuses described herein. For example, the process 3020 can be executed by a controller of any of the one or more load monitoring The process 3020 can determine loading or unloading of a body part, classify activity, determine activity duration, or the like. The process 3020 can output any of these values or indications for presentation to a user. For example, the process 3020 can output activity classification or duration to a clinician, thereby allowing the clinician to gain better understanding of the patient's lifestyle in order to prescribe or modify treatment regimen of a pressure ulcer. In some examples, determining activity classification or duration can facilitate determination of when and for how long a patient is mobile. As another example, the process 3020 can classify activity or duration to alert the patient to take action, such as unload the foot. The process 3020 can output data for presentation wirelessly or using one or more wired connections.

In block 3022, the process 3020 can receive pressure data indicative of pressure magnitude, frequency, or the like. In some embodiments, pressure is measured in a fluid flow path coupling a negative pressure source to a dressing as described herein. In some implementations, pressure is measured in a sealed environment that does not include negative pressure. As described herein, a pressure sensor can communicate measured pressure wirelessly or over a wired interface.

In block 3024, the process 3020 can receive motion data associated with the monitored body part. As described herein, one or more motion sensors can collect motion data. The one or more motion sensors can communicate motion data wirelessly or over a wired interface In block 3026, pressure data received at block 3022 and motion data received at block 324 can be compared with one or more corresponding thresholds. The process 3020 can identify instances where pressure or motion thresholds have been met or exceeded, which can correlate to certain activities as described herein. In addition or alternatively, the process 3020 can evaluate the peak-to-peak or peak-to-trough measurements to determine frequency of pressure or motion changes.

In block 3028, the process 3020 determines activity classification or duration using comparisons performed in block 3026. The process 3020 can, for instance, analyze a change in a magnitude of the pressure during the time period (such as during the time period of at least 1 second, 10 seconds, 30 seconds, 1 minute, 5 minutes, or the like). The activity classification can include one or more of sitting, walking, standing, running, jumping, climbing or traversing stairs, extending or bending the leg, performing squats, or the like.

In some example implementations, the process 3020 can compare the magnitude or frequency of pressure or motion over time to one or more pressure or motion patterns or other measures of variation to determine the appropriate activity classification from the pressure during the time period. The process 3020 can identify the duration of the activity by identifying start and end of the activity.

In some embodiments, the process 3020 can analyze data continuously as it is transmitted from the sensors. This can refer to real-time processing. In some embodiments, the data is not analyzed continuously, but rather is stored in memory and analyzed at predetermined times or upon request.

In block 3028, the process 3020 can utilize various thresholds. For instance, if the patient's foot experiences acceleration above a threshold and immediately thereafter pressure increases (or decreases in a negative pressure environment) above a threshold, the process 3020 can determine that a step was taken. Likewise, if motion data indicates acceleration of the foot, but no change in pressure is being recorded, the process 3020 can determine that the foot is being moved without loading the foot, such as for example by swinging the foot. The process 3020 can additionally or alternatively analyze data received from a gyroscope or magnetometer to determine activity classification or duration.

In block 3030, the process 3020 can output activity classification or duration determined in block 3028. Output can include one or more of: outputting for storage in memory, transmitting to one or more remote devices, outputting for presentation to a user, or the like.

The process 3020 can additionally control operation of the load monitoring system or apparatus. For example, the process 3020 can enable or disable provision of negative pressure.

In some embodiments, if the duration of the activity is approaching or exceeding a threshold, the process 3020 can provide a notification to the patient. The notification can be visual, audible, cognitive, haptic, or the like. The notification can be transmitted to a remote device.

The output of activity classification or load duration can be configured to alert the patient when certain conditions are met. For instance, a patient may be instructed to stand for no longer than 3 minutes at a time. The process 3020 can notify the patient that allowed standing time has been reached or exceeded. As another example, for venous leg ulcers or other low extremity wounds, walking, elevation, or the like can be tracked by the process 3020. The process 3020 can notify the patient to elevate the leg of a period of time to improve blood flow.

Orthopedic Device Use Monitoring

The use of an orthopedic device (such as a contact cast or walking boot) that offloads weight from a body part can be important for healing injury (such as a broken bone or orthopaedic trauma,) or preventing injury (such as a pressure ulcer) to the body part. The orthopedic device may be provided by caregiver to a patient with particular instructions to use the orthopedic device in a manner to heal or prevent injury. Unfortunately, in some instances, the patient may fail to utilize the orthopedic device as instructed by the caregiver, and a desired healing or injury prevention may not be fully realized or may be realized less quickly than is possible.

To help increase use or compliant use of an orthopedic device, a monitoring system like the monitoring system 1000 of FIG. 4 can automatically monitor utilization or compliant use of the orthopedic device. The load monitoring apparatus 1002 can, for example, detect when the orthopedic device is present or monitor one or more signals responsive to use of the orthopedic device for features indicative of compliant use.

Figure 24:
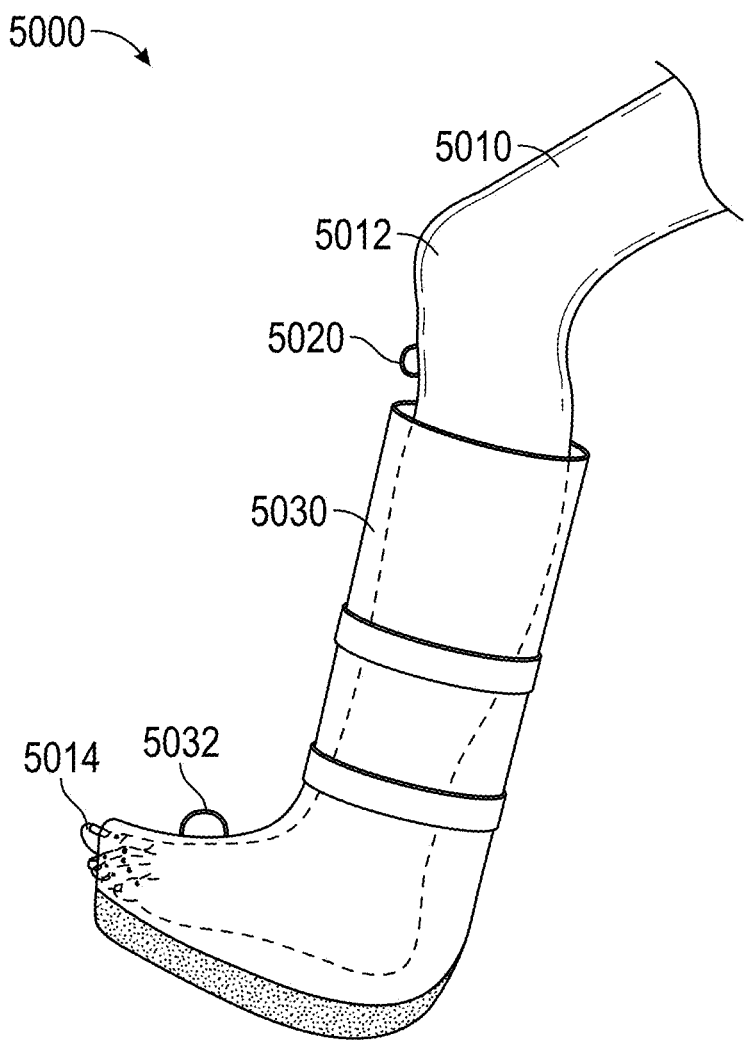
FIG. 24 illustrates a monitoring system that includes a load monitoring apparatus and an orthopedic device according to some embodiments.

FIG. 24 illustrates a monitoring system 5000 that includes a load monitoring apparatus 5020 and an orthopedic device 5030. The load monitoring apparatus 5020 and the orthopedic device 5030 are shown as separately attached to a leg 5010. The load monitoring apparatus 5020 can be below and proximate to a knee 5012, and the orthopedic device 5030 can cover part of a foot 5014 and a lower portion of the leg 5010 (such as to up to an ankle, a mid-shin area, or the knee 5010).

The load monitoring apparatus 5020 can, for example, be the same as or similar to the load monitoring apparatus 1002. The orthopedic device 5030 can be a foot cover and include a compliance device 5032 that transmits or receives a signal usable to monitor use or compliance of use of the orthopedic device 5030. The compliance device 5032 may transmit the signal to the load monitoring apparatus 5020 or receive the signal from the load monitoring apparatus 5020. The signal can then be used to monitor a distance, position, or orientation of the orthopedic device 5030 with respect to the leg 5010.

The load monitoring apparatus 5020 and the compliance device 5032 can together include one or more signal transmitter or detector pairs that monitor the distance or orientation of the orthopedic device 5030 with respect to the leg 5010. In one example, the compliance device 5032 can include a magnet, such as a permanent magnet like a rare-earth magnet that includes samarium-cobalt or neodymium-iron-boron (NIB). The load monitoring apparatus 5020 can include a magnetometer that generates a signal responsive to a magnetic field of the magnet of the compliance device 5032. A signal strength of, perturbations in, or a directionality of the detected magnetic field can be monitored by the load monitoring apparatus 5020 and used to identify a proximity, orientation, and fit of the orthopedic device 5030. In a further example, the load monitoring device 5020 can include a magnet, and the compliance device 5032 can include a magnetometer that detects a signal strength of, perturbations in, or a directionality of the detected magnetic field and be used to identify a proximity, orientation, and fit of the orthopedic device 5030. In another example, the load monitoring apparatus 5020 and the compliance device 5032 can include one or more electromagnetic wave transmitter and detector pairs (for example, communicating using a low power wireless transmission protocol like iBeacon), and signal strengths of detected electromagnetic waves can be used to determine a distance between (such as with a precision of 1 cm), position with respect to, or orientation between the one or more electromagnetic wave transmitter and detector pairs and thus the load monitoring apparatus 5020 and the compliance device 5032. In yet another example, a radio frequency ID (RFID) tag in the orthopedic device 5030 can be in communication with the load monitoring apparatus 5020, and the RFID can be used as a strain gauge to determine when the orthopedic device 5030 may be in use if the aerial is allowed to deform due to weight being placed on the leg 5010.

Additionally or alternatively, the load monitoring apparatus 5020 and the compliance device 5032 can each include a sensor that detects a common force or energy, and outputs of the sensors can be compared to infer common use and compliance. In one example, the load monitoring apparatus 5020 and the compliance device 5032 can each include a motion sensor like an accelerometer that monitors movement, and differences in movement between the load monitoring apparatus 5020 and the compliance device 5032 can be treated as indicative of nonuse or noncompliant use of the orthopedic device 5030 or an improper fit of the orthopedic device 5030. In yet another example, the load monitoring apparatus 5020 and the compliance device 5032 can each include a gyroscope, and differences in outputs of the gyroscopes at common times can be indicative of nonuse or noncompliant use of the orthopedic device 5030 or an improper fit of the orthopedic device 5030.

Although FIG. 24 shows the load monitoring apparatus 5020 positioned below and proximate to the knee 5012, the load monitoring apparatus 5020 may instead be positioned at another location like underneath the orthopedic device 5030, above the knee 5010, on a thigh of the leg 5010, in a user's pocket, or as part of a user's clothing or jewelry (such as a shirt, a wrist watch, a bracelet, or a necklace).

Figure 25A:
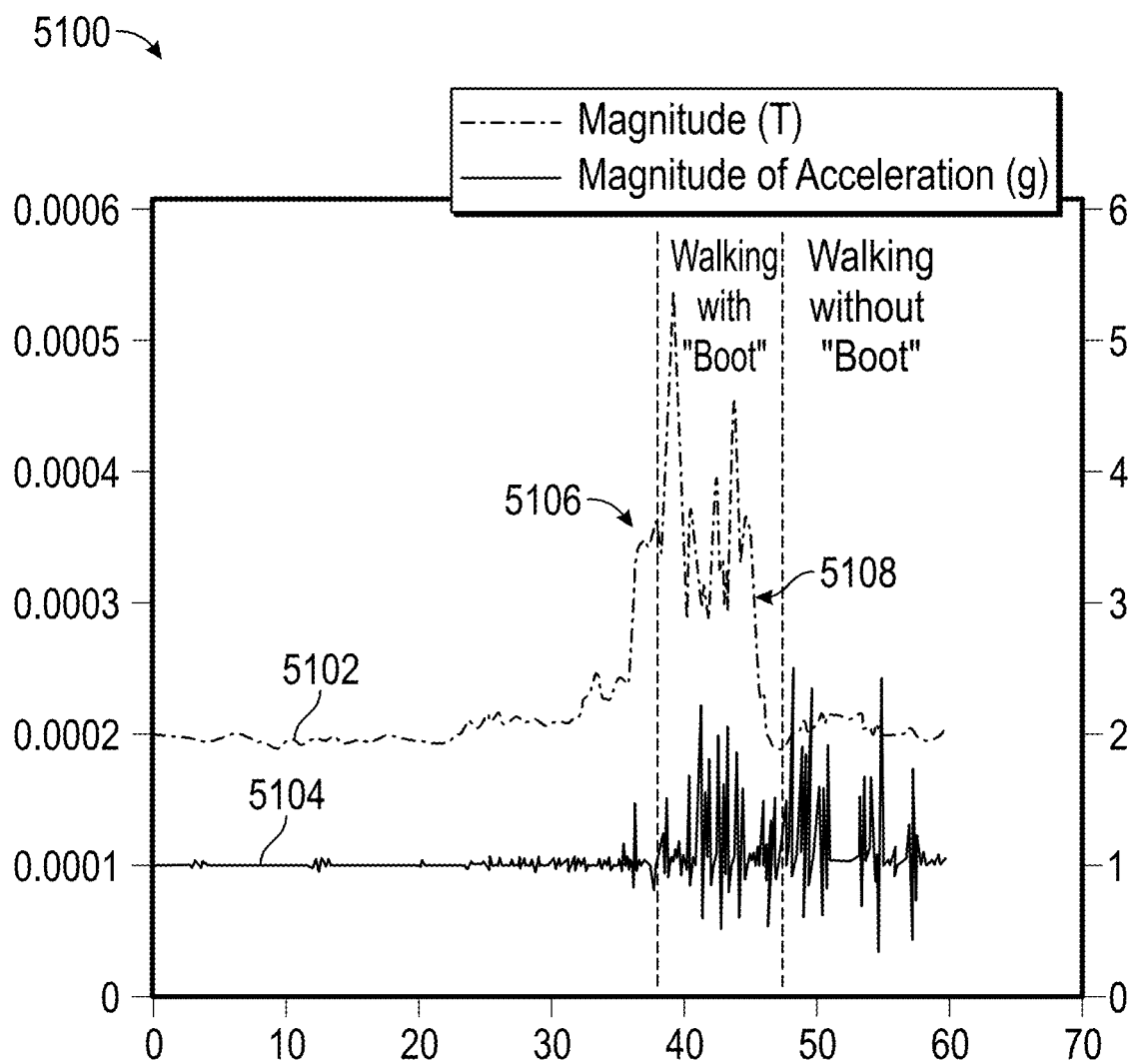
FIGS. 25A and 25B illustrate plots of magnitudes of magnetic field and acceleration during operation of a load monitoring apparatus and an orthopedic device according to some embodiments.

FIG. 25A illustrates a plot 5100 of magnitudes of magnetic field and acceleration during operation of the load monitoring apparatus 5020 and the orthopedic device 5030, where the orthopedic device 5030 includes a magnet detected as a magnetic field by a magnetometer of the load monitoring apparatus 502. A magnetic field waveform 5102 of the plot 5100 can be the output of the magnetometer. The load monitoring apparatus 5020 can further include an accelerometer that outputs a signal responsive to movement, where a magnitude of the signal may be an acceleration waveform 5104 of the plot 5100. A first arrow 5106 designates a time when the orthopedic device 5030 is first attached to the leg 5010, and the second arrow 5108 designates a time when the orthopedic device 5030 is subsequently detached from the leg 5010.

As can be seen from the plot 5100, the magnetometer of the load monitoring apparatus 5020 can first detect a magnetic field from the magnet of the orthopedic device 5030 at the first arrow 5106. The presence of the magnetic field can mean that the orthopedic device 5030 is positioned in the proximity of the load monitoring apparatus 5020 and may be in use on the leg 5010. Perturbations in magnetic field after the first arrow 5106, such as periodic variations, can indicate how the orthopedic device 5030 is being used, such as in use during walking. The reduction in the magnetic field at the second arrow 5108 to a lower field level (for example, which may due to the Earth's magnetic field or another magnetic field in the environment) can indicate that the orthopedic device 5030 is no longer positioned in the proximity of the load monitoring apparatus 5020 and no longer in use on the leg 5010.

The acceleration waveform 5104 after the first arrow 5106 shows variations in magnitude that are indicative of walking. The magnetic field waveform 5102 notably further indicates when and whether the walking was performed with or without the orthopedic device 5030. In situations where walking without the orthopedic device 5030 may generate or aggravate a pressure ulcer, the acceleration waveform 5104 can be used to identify a benefit for the orthopedic device 5030 while the magnetic field waveform 5102 can be used to monitor compliant use of the orthopedic device 5030.

Figure 25B:
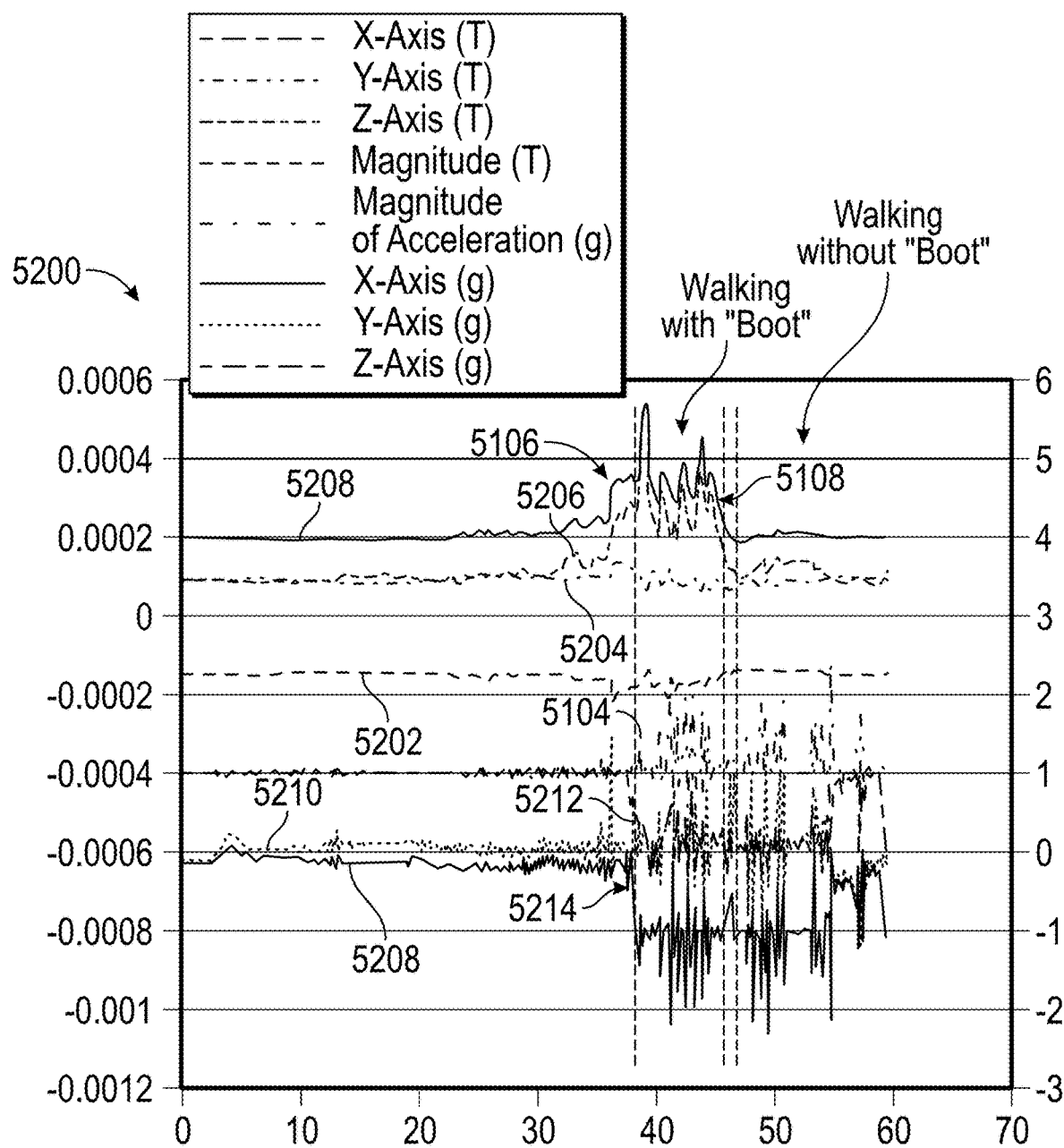

FIG. 25B illustrates a plot 5200 of magnitudes of magnetic field and acceleration during operation of the load monitoring apparatus 5020 and the orthopedic device 5030. The plot 5200 can be a more detailed version of the plot 5100 and illustrate x-axis, y-axis, and z-axis components of the magnetic field waveform 5102 and the acceleration waveform 5104. The magnetic field waveform 5102 may be determined from an x-axis magnetic field waveform 5202, a y-axis magnetic field waveform 5204, and a z-axis magnetic field waveform 5206. The acceleration waveform 5104 may be determined from an x-axis acceleration waveform 5208, a y-axis acceleration waveform 5210, and a z-axis acceleration waveform 5212. A third arrow 5214 designates a time when the leg 5010 may be first placed on a floor.

Figure 26:
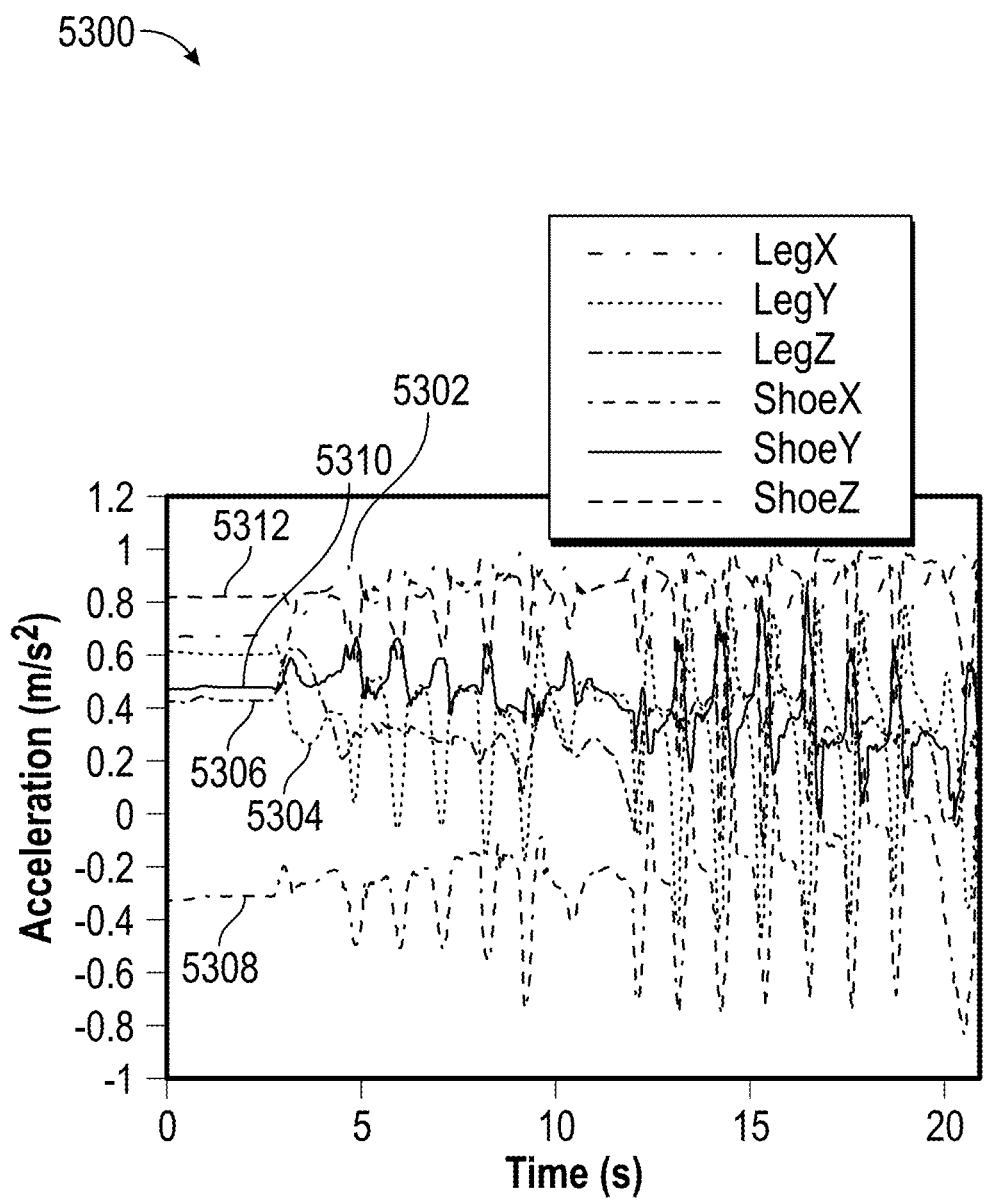
FIG. 26 illustrates a plot of magnitudes of acceleration during operation of a load monitoring apparatus and an orthopedic device 5030 according to some embodiments.

FIG. 26 illustrates a plot 5300 of magnitudes of acceleration during operation of the load monitoring apparatus 5020 and the orthopedic device 5030, where the load monitoring apparatus 5020 and the orthopedic device 5030 both include accelerometers. An x-axis leg acceleration waveform 5302, a y-axis leg acceleration waveform 5304, and a z-axis leg acceleration waveform 5306 are shown and may be output by the accelerometer of the load monitoring apparatus 5020. An x-axis shoe acceleration waveform 5308, a y-axis shoe acceleration waveform 5310, and a z-axis shoe acceleration waveform 5312 are shown and may be output by the accelerometer of the orthopedic device 5030.

A comparison of the waveforms of the plot 5300, such as the x-axis leg acceleration waveform 5302 and the x-axis shoe acceleration waveform 5308, at common times can be used to detect similar motion by the load monitoring apparatus 5020 and the orthopedic device 5030. The similar motion can be indicative of the use of the orthopedic device 5030. In addition, a similar motion but with clipping or a single-sided profile in one of more of the x-axis shoe acceleration waveform 5308, the y-axis shoe acceleration waveform 5310, and the z-axis shoe acceleration waveform 5312 can, for instance, indicate use of the orthopedic device 5030 but an improper fit (for example, a loose fitting) or non-compliant use. Moreover, the various waveforms of the plot 5300 can also provide an orientation of the load monitoring apparatus 5020 and the orthopedic device 5030 with respect to gravity.

Figure 27:
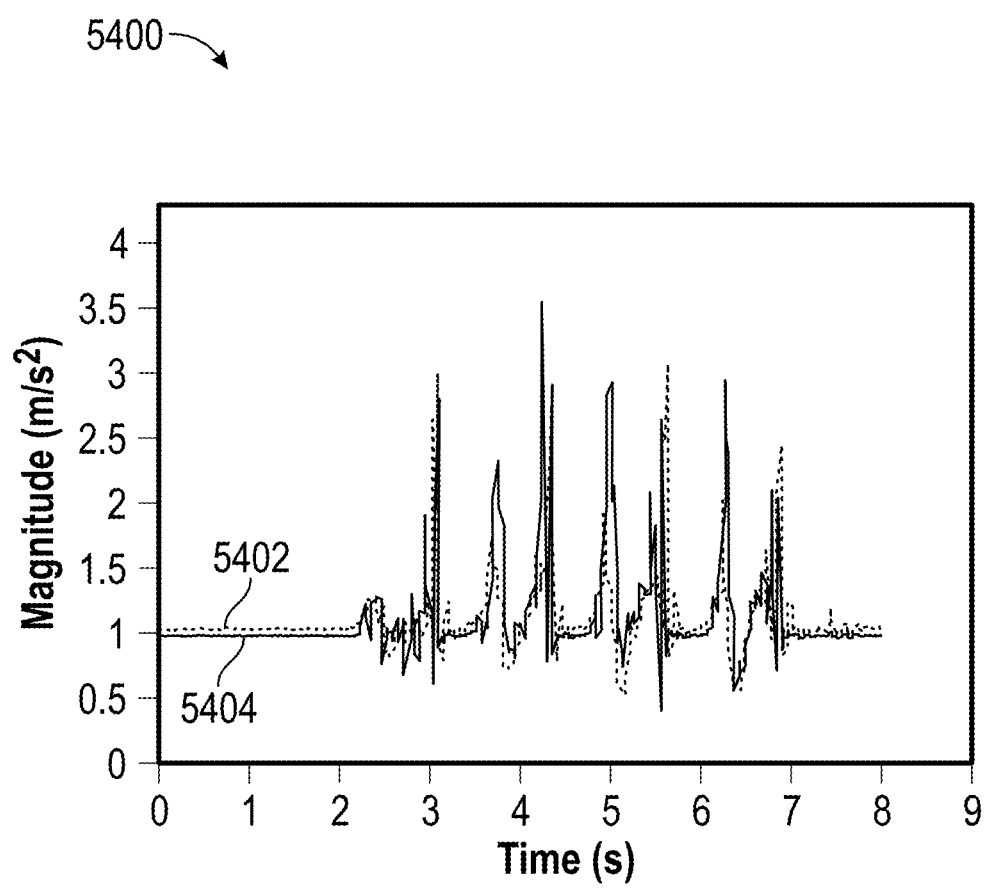
FIG. 27 illustrates a plot of magnitudes of acceleration during operation of a load monitoring apparatus and an orthopedic device according to some embodiments.

FIG. 27 illustrates a plot 5400 of magnitudes of acceleration during operation of the load monitoring apparatus 5020 and the orthopedic device 5030, where the load monitoring apparatus 5020 and the orthopedic device 5030 both include accelerometers. An orthopedic device acceleration waveform 5402 is shown and may be output by the accelerometer of the orthopedic device 5030. A leg acceleration waveform 5404 is shown and may be output by the accelerometer of the load monitoring apparatus 5020.

As can be seen from the plot 5400, the orthopedic device acceleration waveform 5402 and the leg acceleration waveform 5404 closely following other and thus can suggest compliant use of the orthopedic device 5030.

Figure 28:
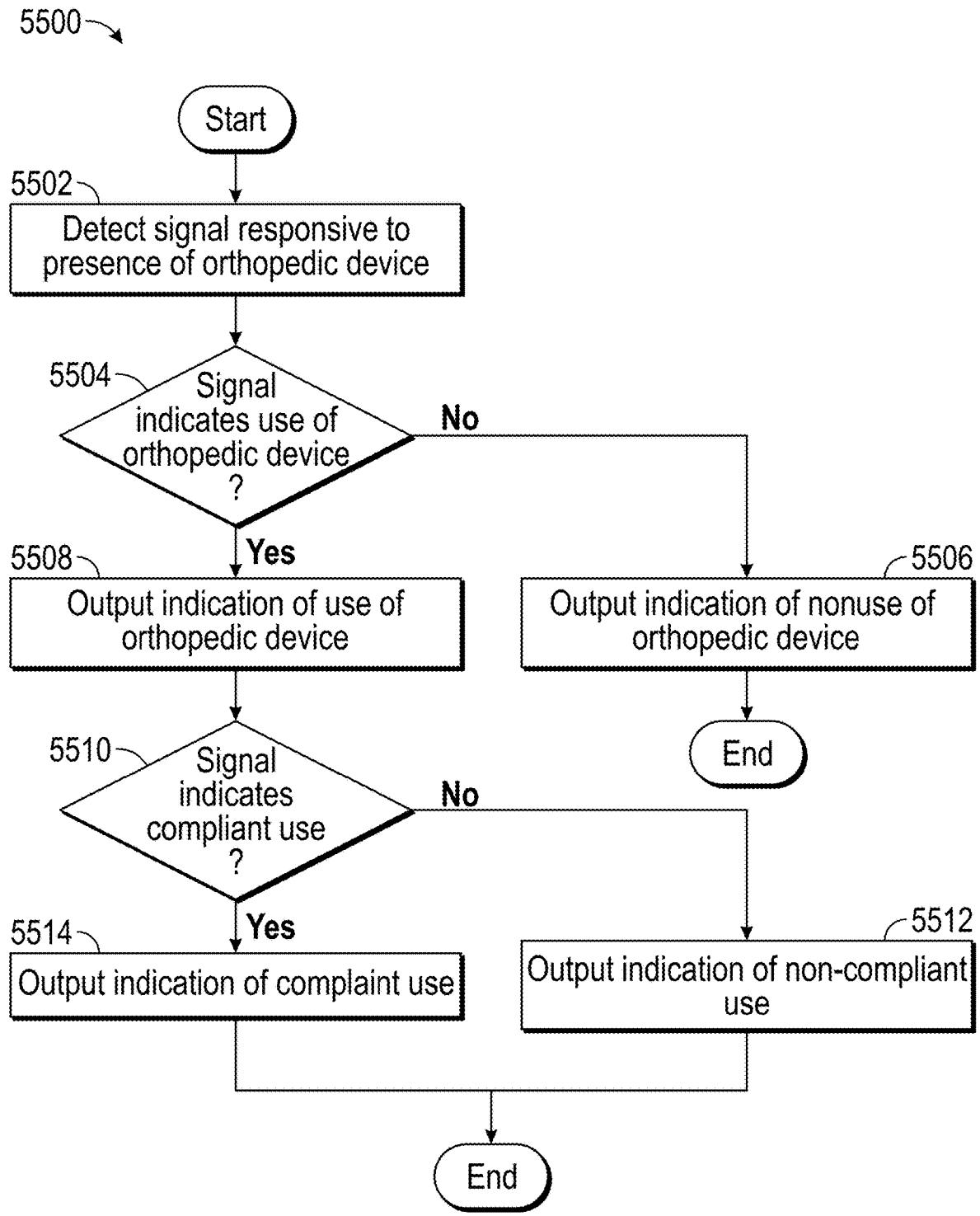
FIG. 28 illustrates a process for monitoring use and compliant use of an orthopedic device with a load monitoring apparatus according to some embodiments.

FIG. 28 illustrates a process 5500 for monitoring use and compliant use of an orthopedic device, such as the orthopedic device 5030 of FIG. 24, with a load monitoring apparatus. For convenience, the process 4600 is described in the context of the monitoring system 5000, but may instead be implemented in other systems described herein, or by other computing systems not shown. The process 5500 can advantageously, in certain embodiments, enable the load monitoring apparatus 5020 to monitor characteristics of use of the orthopedic device 5030.

At block 5502, the process 5500 can generate a signal responsive to presence of an orthopedic device used to offload weight for a body part. A magnetometer of the load monitoring apparatus 5020 can, for example, detect a magnetic field generated by a magnet of the compliance device 5032 and generate a signal responsive to the magnetic field. The magnetic field of the magnet can have a field strength greater than 100 µT at a distance of 10 cm, 20 cm, 30 cm, 50 cm, or 100 cm or when detected at the magnetometer if the orthopedic device 5030 is properly worn on the leg 5010. The magnetometer may also be used to detect an orientation of the orthopedic device 5030 with respect to a magnetic north of Earth, and the magnet of the compliance device 5032 can be selected to generate a magnetic field at the magnetometer that is stronger than the magnetic field of the magnetic north of Earth.

At block 5504, the process 5500 can determine whether the signal indicates use of the orthopedic device. For instance, a controller of the load monitoring apparatus 5020 can process the signal for one or more characteristics indicative of use of the orthopedic device 5030. The one or more characteristics can include a magnitude or derivative of the signal satisfying a use-associated threshold, a pattern of the signal sufficiently matching a pattern indicative of use of the orthopedic device 5030, or a directionality associated with the signal such as a north or south direction field indicative of proper alignment or fit, among other possibilities.

If the process 5500 determines that the signal does not indicate use of the orthopedic device, at block 5506, the process 5500 can output an indication of nonuse of the orthopedic device. The controller of the load monitoring apparatus 5020 can, for example, output the indication of nonuse for presentation on a display or for storage in a memory device.

If the process 5500 determines that the signal indicates use of the orthopedic device, at block 5508, the process 5500 can output an indication of use of the orthopedic device. The controller of the load monitoring apparatus 5020 can, for example, output the indication of use for presentation on a display or for storage in a memory device.

After block 5508, the process 5500 can transition to block 5510 and determine whether the signal indicates compliant use of the orthopedic device. For example, the controller of the load monitoring apparatus 5020 can process the signal for one or more characteristics indicative of compliant use of the orthopedic device 5030. The one or more characteristics can include a magnitude or derivative of the signal satisfying a compliant use-associated threshold, a pattern of the signal sufficiently matching a pattern indicative of compliant use of the orthopedic device 5030, or a directionality associated with the signal such as a north or south direction field indicative of compliant alignment or fit over time, among other possibilities. Moreover, the controller of the load monitoring apparatus 5020 can determine what activities are engaged in from the signal (as described elsewhere herein, for instance) and determine whether the activities and thus corresponding use of the orthopedic device 5030 match permitted activity information stored in a memory device.

If the process 5500 determines that the signal does not indicate compliant use of the orthopedic device, at block 5512, the process 5500 can output an indication of non-compliant use of the orthopedic device. The controller of the load monitoring apparatus 5020 can, for example, output the indication of non-compliant use for presentation on a display or for storage in a memory device.

If the process 5500 determines that the signal indicates compliant use of the orthopedic device, at block 5514, the process 5500 can output an indication of compliant use of the orthopedic device. The controller of the load monitoring apparatus 5020 can, for example, output the indication of compliant use for presentation on a display or for storage in a memory device.

OTHER VARIATIONS

Any value of a threshold, limit, duration, etc. provided herein is not intended to be absolute and, thereby, can be approximate. In addition, any threshold, limit, duration, etc. provided herein can be fixed or varied either automatically or by a user. Furthermore, as is used herein relative terminology such as exceeds, greater than, less than, etc. in relation to a reference value is intended to also encompass being equal to the reference value. For example, exceeding a reference value that is positive can encompass being equal to or greater than the reference value. In addition, as is used herein relative terminology such as exceeds, greater than, less than, etc. in relation to a reference value is intended to also encompass an inverse of the disclosed relationship, such as below, less than, greater than, etc. in relations to the reference value. Moreover, although blocks of the various processes may be described in terms of determining whether a value meets or does not meet a particular threshold, the blocks can be similarly understood, for example, in terms of a value (i) being below or above a threshold or (ii) satisfying or not satisfying a threshold.

Features, materials, characteristics, or groups described in conjunction with a particular aspect, embodiment, or example are to be understood to be applicable to any other aspect, embodiment or example described herein unless incompatible therewith. All of the features disclosed in this specification (including any accompanying claims, abstract and drawings), or all of the steps of any method or process so disclosed, may be combined in any combination, except combinations where at least some of such features or steps are mutually exclusive. The protection is not restricted to the details of any foregoing embodiments. The protection extends to any novel one, or any novel combination, of the features disclosed in this specification (including any accompanying claims, abstract and drawings), or to any novel one, or any novel combination, of the steps of any method or process so disclosed.

While certain embodiments have been described, these embodiments have been presented by way of example only, and are not intended to limit the scope of protection. Indeed, the novel methods and systems described herein may be embodied in a variety of other forms. Furthermore, various omissions, substitutions and changes in the form of the methods and systems described herein may be made. Those skilled in the art will appreciate that in some embodiments, the actual steps taken in the processes illustrated or disclosed may differ from those shown in the figures. Depending on the embodiment, certain of the steps described above may be removed, others may be added. For example, the actual steps or order of steps taken in the disclosed processes may differ from those shown in the figure. Depending on the embodiment, certain of the steps described above may be removed, others may be added. For instance, the various components illustrated in the figures may be implemented as software or firmware on a processor, controller, ASIC, FPGA, or dedicated hardware. Hardware components, such as controllers, processors, ASICs, FPGAs, and the like, can include logic circuitry. Furthermore, the features and attributes of the specific embodiments disclosed above may be combined in different ways to form additional embodiments, all of which fall within the scope of the present disclosure.

Although the present disclosure includes certain embodiments, examples and applications, it will be understood by those skilled in the art that the present disclosure extends beyond the specifically disclosed embodiments to other alternative embodiments or uses and obvious modifications and equivalents thereof, including embodiments which do not provide all of the features and advantages set forth herein. Accordingly, the scope of the present disclosure is not intended to be limited by the specific disclosures of preferred embodiments herein, and may be defined by claims as presented herein or as presented in the future.

Conditional language, such as "can," "could," "might," or "may," unless specifically stated otherwise, or otherwise understood within the context as used, is generally intended to convey that certain embodiments include, while other embodiments do not include, certain features, elements, or steps. Thus, such conditional language is not generally intended to imply that features, elements, or steps are in any way required for one or more embodiments or that one or more embodiments necessarily include logic for deciding, with or without user input or prompting, whether these features, elements, or steps are included or are to be performed in any particular embodiment. The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list. Further, the term "each," as used herein, in addition to having its ordinary meaning, can mean any subset of a set of elements to which the term "each" is applied.

Conjunctive language such as the phrase "at least one of X, Y, and Z," unless specifically stated otherwise, is otherwise understood with the context as used in general to convey that an item, term, etc. may be either X, Y, or Z. Thus, such conjunctive language is not generally intended to imply that certain embodiments require the presence of at least one of X, at least one of Y, and at least one of Z.

Language of degree used herein, such as the terms "approximately," "about," "generally," and "substantially" as used herein represent a value, amount, or characteristic close to the stated value, amount, or characteristic that still performs a desired function or achieves a desired result. For example, the terms "approximately", "about", "generally," and "substantially" may refer to an amount that is within less than 10% of, within less than 5% of, within less than 1% of, within less than 0.1% of, and within less than 0.01% of the stated amount. As another example, in certain embodiments, the terms "generally parallel" and "substantially parallel" refer to a value, amount, or characteristic that departs from exactly parallel by less than or equal to 15 degrees, 10 degrees, 5 degrees, 3 degrees, 1 degree, or 0.1 degree.

The scope of the present disclosure is not intended to be limited by the specific disclosures of preferred embodiments in this section or elsewhere in this specification, and may be defined by claims as presented in this section or elsewhere in this specification or as presented in the future. The language of the claims is to be interpreted broadly based on the language employed in the claims and not limited to the examples described in the present specification or during the prosecution of the application, which examples are to be construed as non-exclusive.

What is claimed is:

1. A system for monitoring load bearing, the system comprising:
   a pressure source configured to provide pressure via a fluid flow path under a dressing, the dressing being configured to be positioned over at least a portion of a foot;
   a pressure sensor configured to monitor a pressure in the fluid flow path;
   a motion sensor configured to monitor a motion of the foot; and
   a controller configured to:
      determine, from (i) a change in the pressure in the fluid flow path and (ii) a change in the motion, a duration of time over which the foot has been loaded to support a threshold weight; and
      output the duration of time for presentation.

2. The system of claim 1, wherein:
   the pressure source is configured to substantially maintain a target pressure under the dressing; and
   the controller is configured to determine, from the target pressure being substantially reestablished under the dressing, that the foot has been loaded to support the threshold weight.

3. The system of claim 2, wherein a loading of the foot causes a decrease in pressure under the dressing, and the pressure source is configured to counteract the decrease in pressure under the dressing from the loading of the foot by substantially reestablishing the target pressure under the dressing.

4. The system of claim 1, wherein the controller is configured to determine, from the change in the pressure in the fluid flow path, that the foot has been loaded to support the threshold weight, and determine, from another change in the pressure in the fluid flow path, that the foot has been unloaded.

5. The system of claim 1, wherein the controller is configured to:
   classify, from the change in the motion, an activity of the foot as an activity classification; and
   output the activity classification for presentation.

6. The system of claim 5, wherein the activity classification comprises one or more of standing, walking, jumping, running, or climbing stairs.

7. The system of claim 6, wherein the controller is configured to classify the activity as standing responsive to the change in the motion substantially indicating no changes in a position of the foot.

8. The system of claim 7, wherein the controller is configured to classify the activity as walking, jumping, running, or climbing stairs responsive to the change in the motion satisfying a walking motion threshold, a jumping motion threshold, a running motion threshold, or a climbing stairs motion threshold.

9. The system of claim 8, wherein the controller is configured to classify the activity as walking, jumping, running, or climbing stairs further from the pressure in the fluid flow path during the duration of time satisfying a walking pressure threshold, a jumping pressure threshold, a running pressure threshold, or a climbing stairs pressure threshold.

10. The system of claim 1, wherein the pressure sensor is configured to be positioned in the fluid flow path proximate to the foot.

11. The system of claim 1, wherein the pressure sensor is configured to be positioned under the dressing.

12. The system of claim 1, wherein the motion sensor is configured to be positioned proximate to the foot.

13. The system of claim 1, wherein the motion sensor is positioned under the dressing.

14. The system of claim 1, wherein the motion sensor comprises an accelerometer.

15. The system of claim 1, wherein the controller is configured to distinguish (i) a decrease in pressure under the dressing associated with a loading of the foot from (ii) a decrease in pressure under the dressing associated with a leak in the fluid flow path.

16. The system of claim 1, wherein the change in the motion is caused by a loading of the foot.

17. A method for monitoring load bearing, the method comprising:
   providing, by a pressure source, pressure via a fluid flow path under a dressing positioned over at least a portion of a foot;
   monitoring, by a pressure sensor, a pressure in the fluid flow path;
   monitoring, by a motion sensor, a motion of the foot; and at a first time:
by a controller, determining, from (i) a change in the pressure in the fluid flow path and (ii) a change in the motion, a duration of time over which a foot has been loaded to support a threshold weight; and
outputting the duration of time for presentation.

18. The method of claim 17, further comprising:
at a second time:
by the controller, determining, from a target pressure being substantially reestablished under the dressing, that the foot has been loaded to support the threshold weight; and
substantially maintaining, by the pressure source, the target pressure under the dressing.

19. The method of claim 17, further comprising:
at a second time:
by the controller, determining, from the change in the pressure in the fluid flow path, that the foot has been loaded to support the threshold weight; and
at a third time:
by the controller, determining, from another change in the pressure in the fluid flow path, that the foot has been unloaded.

20. A system for monitoring load bearing, the system comprising:
a pressure source configured to provide pressure via a fluid flow path under a dressing, the dressing being configured to be positioned over at least a portion of a limb;
a pressure sensor configured to monitor a pressure in the fluid flow path;
a motion sensor configured to monitor a motion of the limb; and
a controller configured to:
determine, from (i) a change in the pressure in the fluid flow path and (ii) a change in the motion, a duration of time over which the limb has been loaded to support a threshold weight; and
output the duration of time for presentation.

* * * * *